US005773423A

United States Patent [19]
Jacobson et al.

[11] Patent Number: 5,773,423
[45] Date of Patent: Jun. 30, 1998

[54] A3 ADENOSINE RECEPTOR AGONISTS

[75] Inventors: Kenneth A. Jacobson, Silver Spring, Md.; Carola Gallo-Rodriguez, Buenos Aires, Argentina; Philip J. M. van Galen, Oss, Netherlands; Dag K. J. E. von Lubitz, Alexandria, Va.; Heaok Kim Jeong, Rockville, Md.

[73] Assignee: The United States of America as represented by the Department of Health and Human Services, Washington, D.C.

[21] Appl. No.: 274,628

[22] Filed: Jul. 13, 1994

Related U.S. Application Data

[63] Continuation-in-part of Ser. No. 163,324, Dec. 6, 1993, abandoned, which is a continuation-in-part of Ser. No. 91,109, Jul. 13, 1993, abandoned.

[51] Int. Cl.[6] .................................................. A61K 31/70
[52] U.S. Cl. ........................... 514/45; 514/46; 536/27.22; 536/27.6; 536/27.63
[58] Field of Search .............................. 536/27.22, 27.6, 536/27.63; 514/45, 46

[56] References Cited

U.S. PATENT DOCUMENTS

| | | | |
|---|---|---|---|
| 3,551,409 | 12/1970 | Kampe et al. | 536/27.63 |
| 5,140,015 | 8/1992 | Olsson et al. | 514/45 |
| 5,310,731 | 5/1994 | Olsson et al. | 514/45 |
| 5,443,836 | 8/1995 | Downey et al. | |

FOREIGN PATENT DOCUMENTS

| | | |
|---|---|---|
| 2524284 | 10/1976 | Germany. |
| WO 86/00310 | 1/1986 | WIPO. |

OTHER PUBLICATIONS

Journal of Medicinal Chemistry, vol, 35, No. 22, pp. 4143–4149, (1992).
Molecular Pharmacology, vol. 29, pp. 331–346 (1986).
Fozard et al., *Br. J. Pharmacol.*, 109, 3–5 (1993).
Jacobson et al., *J. Med. Chem.*, 35, 407–422 (1992).
Kampe et al., *Chem. Abstr.*, 70, 88212z (1969).
Koch et al., *Chem. Abstr.*, 72, 21921c (1970).
Kusachi et al., *J. Med. Chem.*, 29, 989–996 (1986).
Mosselhi, *Nucleos. Nucleot.*, 12, 431–439 (1993).
van Galen et al., *Nucleos. Nucleot.*, 10, 1191–1193 (1991).
Ali et al., *J. Biol. Chem.*, 265, 745–753 (1990).
Beaven et al., *Trends Pharm. Sci.*, 15, 13–14 (1994).
Borea et al., *Int. J. Purine and Pyrimidine Res.*, 3, 65 (1992).
Borea et al., *Eur. J. Pharmacol.* (Mol. Pharm. Section), 267, 55–61.
Brackett et al., *Biochem. Pharmacol.*, 47, 801–814 (1994).
Fozard et al., *Br. J. Pharmacol.*, 109, 3–5 (1993).
Gallo–Rodriguez et al., *J. Med. Chem.*, 37, 636–646 (1994).
Hide et al., *Mol. Pharmacol.*, 41, 352–359 (1992).
Jacobson et al., *FEBS Letters*, 323, 141–144 (1993).
Jacobson et al., *FEBS Letters*, 336, 57–60 (1993).
Jarvis et al., *J. Pharmacol. Exp. Therap.*, 251, 888–893 (1989).
Jasper et al., *Biochem. Pharmacol.*, 43, 119–130 (1992).
Linden et al., *Mol. Pharmacol.*, 44, 524–532 (1993).
Olah et al., *Mol. Pharmacol.*, 45, 978–982 (1994).
Salvatore et al., *Proc. Natl. Acad. Sci. U.S.A.*, 90, 10365–10369 (1993).
Schwabe et al., *Naunyn–Schmiedeberg's Arch. Pharmacol.*, 313, 179–187 (1980).
van Galen et al., *Mol. Pharmacol.*, 45, 1101–1111 (1994).
van der Wenden et al., *Drug Devel. Res.*, 31, 314 (Abstract 1190) (1994).
von Lubitz et al., *Drug Devel. Res.*, 31, 332 (Abstract 1224) (1994).
von Lubitz et al., *Neurosci. Abstr.*, (1994).

*Primary Examiner*—James O. Wilson
*Attorney, Agent, or Firm*—Leydig, Voit & Mayer, Ltd.

[57] ABSTRACT

The present invention provides $N^6$-benzyladenosine-5'-N-uronamide and related substituted compounds, particularly those containing substituents on the benzyl and/or uronamide groups, and modified xanthine ribosides, as well as pharmaceutical compositions containing such compounds. The present invention also provides a method of selectively activating an $A_3$ adenosine receptor in a mammal, which method comprises acutely or chronically administering to a mammal in need of selective activation of its $A_3$ adenosine receptor a therapeutically effective amount of a compound which binds with the $A_3$ receptor so as to stimulate an $A_3$ receptor-dependent response.

50 Claims, 8 Drawing Sheets

A3 ADENOSINE RECEPTOR AGONISTS

This application is a continuation-in-part of U.S. patent application Ser. No. 08/163,324, filed on Dec. 6, 1993, which is now abandoned, which is a continuation-in-part of U.S. patent application Ser. No. 08/091,109, filed on Jul. 13, 1993, which is now abandoned.

TECHNICAL FIELD OF THE INVENTION

The present invention relates to $A_3$ adenosine receptor agonists and methods of selectively activating an $A_3$ adenosine receptor in a mammal. The present invention also relates to methods of treating various medical disorders with $A_3$ adenosine receptor agonists.

BACKGROUND OF THE INVENTION

Adenosine receptors, belonging to the superfamily of the G protein-coupled receptors, are generally divided into two major subclasses, $A_1$ and $A_2$, on the basis of the differential affinities of a number of adenosine receptor agonists and antagonists for the receptors, their primary structures, and the secondary messenger systems to which they couple. Thus, $A_2$ receptors, which can be further subdivided into $A_{2a}$ and $A_{2b}$, stimulate adenylate cyclase, whereas $A_1$ receptors may couple to a variety of secondary messenger systems, including those involved in the inhibition of adenylate cyclase, the inhibition or stimulation of phosphoinositol turnover, the activation of guanylate cyclase, the activation of potassium influx, and the inhibition of calcium influx (van Galen et al., *Med. Res. Rev.*, 12, 423–471 (1992), and Jacobson et al., *J. Med. Chem.*, 35, 407–422 (1992)).

Recently, a novel adenosine receptor was identified 35 on the basis of its primary structure and cloned from rat brain (Zhou et al., *Proc. Natl. Acad. Sci. U.S.A.*, 89, 7432–7436 (1992)) and rat testis (Meyerhof et al., *FEBS Lett.*, 284, 155–160 (1991)). The putative transmembrane domains of the novel adenosine receptor, which has been designated the $A_3$ receptor, show 58% identity with the canine $A_1$ receptor and 57% with the canine $A_{2a}$ receptor. Like the $A_1$ receptor, the $A_3$ receptor is negatively coupled to adenylate cyclase (Zhou et al., supra).

The potential utility of $A_1$- and $A_2$-selective agents in therapeutic applications has been limited by accompanying side effects, given the ubiquitous nature of the $A_1$ and $A_2$ receptors. The distribution of the $A_3$ receptor, by contrast, is fairly limited, being found primarily in the central nervous system (CNS) (Zhou et al., supra), brain, testes (Meyerhof et al., supra), and immune system, where it appears to be involved in the modulation of release from mast cells of mediators of the immediate hypersensitivity reaction (Ramkumar et al., *J. Biol. Chem.*, 268, 16887–16890 (1993)). The limited distribution of the $A_3$ receptor provides a basis for predicting that $A_3$-selective compounds may be more useful than $A_1$- and $A_2$-selective compounds as potential therapeutic agents. It is believed that $A_3$-selective compounds will have utility in the therapeutic and/or prophylactic treatment of cardiac disease, infertility, kidney disease, and CNS disorders.

Few ligands for this novel receptor have been reported. Some non-selective $N^6$-substituted adenosine derivatives have been described as agonists for the $A_3$ receptor, including APNEA ($N^6$-2-(4-aminophenyl)ethyladenosine), which has been used successfully as a radioligand in its iodinated form (Zhou et al., supra). Typical xanthine and nonxanthine $A_1$ and $A_2$ receptor antagonists, however, do not appear to bind to this receptor (Zhou et al., supra).

Thus, there remains a need for $A_3$-selective agonists. The present invention seeks to provide such compounds, as well as methods of using these compounds to selectively activate the $A_3$ receptor in mammals, and pharmaceutical compositions comprising such compounds. These and other objects and advantages of the present invention, as well as additional inventive features, will be apparent from the description of the invention provided herein.

BRIEF SUMMARY OF THE INVENTION

The present invention provides $A_3$ selective agonists, particularly $N^6$-benzyladenosine-5'-uronamide and related substituted compounds, particularly those containing substituents on the benzyl and/or uronamide groups, and xanthine riboside derivatives, as well as pharmaceutical compositions containing such compounds. The present invention also provides a method of selectively activating an $A_3$ adenosine receptor in a mammal, which method comprises acutely or chronically administering to a mammal in need of selective activation of its $A_3$ adenosine receptor a therapeutically or prophylactically effective amount of a compound which binds with the $A_3$ receptor so as to stimulate an $A_3$ receptor-dependent response.

DESCRIPTION OF THE PREFERRED EMBODIMENTS

Figure 1:
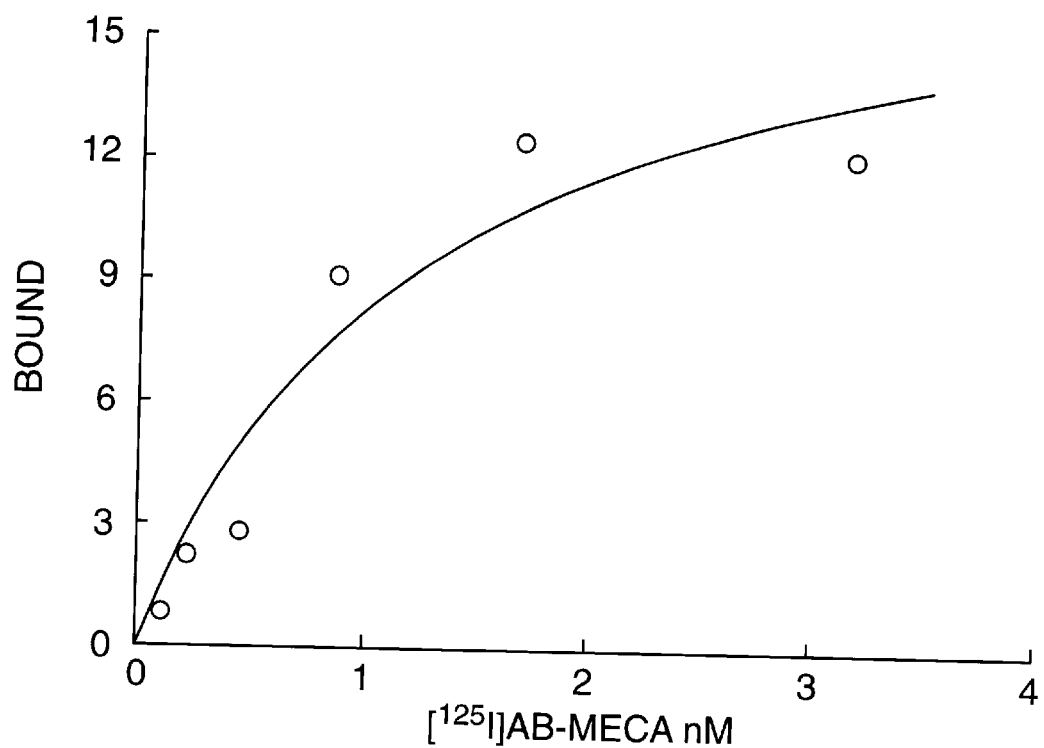
FIG. 1 is a graph of $A_3$ adenosine receptor binding versus concentration of $[^{125}I]$AB-MECA (nM).

The present invention provides for compounds which have been found to be selective $A_3$ adenosine receptor agonists, pharmaceutical compositions containing such compounds, and related treatment methods and assay methods.

The modification of adenosine at the 5'-position and/or at the $N^6$-position with groups that enhance $A_3$ potency has been found to result in moderate $A_3$ selectivity. In particular, the 5'-methyluronamide modification of adenosine and the $N^6$-benzyl group, either alone or in combination, increases affinity in binding to $A_3$ receptors relative to $A_1$ and $A_{2a}$ receptors. Optimization of substituent groups has led to the development of the highly potent $A_3$ agonist $N^6$-(3-iodobenzyl)-adenosine-5'-N-methyluronamide (IB-MECA) which is 50-fold selective for $A_3$ vs. either $A_1$ or $A_2$ receptors. A closely related, but less selective radioligand, [$^{125}$I]AB-MECA, has been developed for characterization of $A_3$ receptors and has been found to have a $K_d$ value of 3.6 nM in binding to rat $A_3$ receptors in the RBL-2H3 mast cell line. While derivatives such as $N^6$-benzyladenosine-5'-N-ethyluronamide have been found to be full agonists in inhibiting adenylate cyclase via rat $A_3$ receptors, such derivatives, while useful, are only one order of magnitude selective for rat $A_3$ receptors vs. either $A_1$ or $A_{2a}$ receptors in binding assays.

Triple substitution of adenosine results in the further enhancement of the degree of $A_3$ selectivity, such that an improvement in selectivity in binding assays of three orders of magnitude or more can be achieved. By combining the two modifications at 5'- and $N^6$-positions, which result in moderate selectivity, with a third site of modification, particularly the 2-position, selectivity can be dramatically increased. For example, 2-chloro-$N^6$-(3-iodobenzyl)-adenosine-5'-N-methyluronamide has been found to be the most potent and selective agent in binding assays and has been shown to be a full agonist in the inhibition of adenylate cyclase. The agonist potency was also greater than that of other agonists, indicating a parallel between binding affinities and relative potencies in this functional assay. Such agonist properties are similarly expected in another relevant functional assay, stimulation of $A_3$-mediated phosphoinositide metabolism.

The novel $A_3$ adenosine receptor is believed to be important in the regulation of CNS, cardiac, inflammatory, and reproductive functions. Activation of $A_3$ receptors enhances the release of inflammatory mediators from mast cells (Ramkumar et al., *J. Biol. Chem.*, 268, 16887–16890 (1993); Ali et al., *J. Biol. Chem.*, 265, 745–753 (1990)), lowers blood pressure (Fozard et al., *Br. J. Pharmacol.*, 109, 3–5 (1993)), and depresses locomotor activity (Jacobson et al., *FEBS Letters*, 336, 57–60 (1993)). Selective agonists are believed to have therapeutic potential as cerebroprotective agents (von Lubitz et al., *Drug Devel. Res.*, 31, 332 (Abstract 1224) (1994), and the activation of $A_3$ receptors is thought to be related to the cardioprotective preconditioning response following exposure to adenosine agonists. It has been discovered that the chronic administration of an $A_3$ agonist provides a cerebroprotective effect. For example, the cerebroprotective effects of IB-MECA have been discovered using an ischemic model in gerbils and NMDA-induced seizures in mice (von Lubitz et al., *Neurosci Abstr.* (1994)). Moreover, the cardioprotective potential of $A_3$ receptor activation, based on use of APNEA coadministered with a xanthine antagonist that does not act at $A_3$ receptors, has been demonstrated. APNEA has been found to be 8-fold $A_1$ selective, and its pharmacological use is limited to such combination with antagonists of both $A_1$ and $A_{2a}$ receptors. Clearly, the availablility of ligands such as those described herein, particularly 2-chloro-$N^6$-(3-iodobenzyl)-9-[5-(methylamido)-β-D-ribofuranosyl]-adenine, could be critical in pharmacological studies of $A_3$ receptors. A highly selective $A_3$ ligand is expected to be especially useful as a radioligand, since the currently used high affinity ligand [$^{125}$I]AB-MECA, is not sufficiently selective for general application in tissue (Olah et al., *Mol. Pharmacol.*, 45, 978–982 (1994).

Although the selectivities of these novel $A_3$ agonists may vary somewhat in different species, due to the unusually large species dependence in ligand affinity at this subtype, such differences appear to be more pronounced for antagonists than for agonists (Linden et al., *Mol. Pharmacol.*, 44, 524–532 (1993); Salvatore et al., *Proc. Natl. Acad. Sci. U.S.A.*, 90, 10365–10369 (1993); Brackett et al., *Biochem. Pharmacol.*, 47, 801–814 (1994)). Thus, it should be noted that 2-chloroadenosine is 17-fold less potent than NECA at rat $A_3$ receptors, whereas at sheep $A_3$ receptors 2-chloroadenosine is 1.7-fold less potent than NECA. Thus, since the most selective compound in the present series, 2-chloro-$N^6$-(3-iodobenzyl)-9-[5-(methylamido)-β-D-ribofuranosyl]-adenine, contains the 2-chloro substitution, it is likely that the selectivity will not be substantially diminished in other species, such as sheep and human. A high degree of correlation in the relative affinities of adenosine derivatives at rat vs. human $A_3$ receptors has been shown.

A high degree of selectivity exists for doubly-substituted derivatives, such as $N^6$-(3-iodobenzyl)-adenosine-5'-N-methyluronamide (IB-MECA), and triply-substituted adenosine derivatives for $A_3$ receptors vs. the NBTI-sensitive adenosine uptake site. 2-substitution is well-tolerated at $A_3$ receptors, whether it be with a small group (e.g., 2-chloro-$N^6$-(3-iodobenzyl)-adenosine) or a large group (e.g., APEC). The potency enhancing effects of 2-substituents appeared to follow the order: chloro>thioether>amine. The effects of 2-substitution to enhance $A_3$ affinity are also additive with effects of uronamides at the 5'-position and a 3-iodobenzyl group at the $N^6$-position, although the $A_3$ affinity-enhancing effect of a 2-chloro group do not appear to be additive with an $N^6$-cyclopentyl group. The combination of most favorable modifications at three positions has led to very potent and highly selective agonist ligands, particularly 2-chloro-$N^6$-(3-iodobenzyl)-9-[5-(methylamido)-β-D-ribofuranosyl]-adenine, $N^6$-(3-iodobenzyl)-2-methylamino-9-[5-(methylamido)-β-D-ribofuranosyl]-adenine, and $N^6$-(3-iodobenzyl)-2-methylthio-9-[5-(methylamido)-β-D-ribofuranosyl]-adenine.

A general parallel has also been found between the structure activity relationships for adenosine $A_3$ agonists and xanthine ribosides, particularly in the ribose moiety. The substituent effects at the 5'-position, i.e., for uronamide derivatives, are nearly identical. This parallel in SAR is supportive of the $A_3$ receptor model which features the ribose moiety of the ligand, either adenosine or xanthine ribosides, coordinated by hydrogen bonding to the same amino acid residue, His of the seventh transmembrane helix.

While the 7-ribosides have affinity for the receptor, the 9-ribosides do not bind. For purposes of comparing SAR, consideration may be given to the case in which the purine rings overlap in a "flipped" orientation, i.e., the xanthine N-7 occupies the same position as the adenosine N-9, xanthine N-3 corresponds rougly to C-6 of adenosine, etc. Thus, the position corresponding to the critical $N^6$-substituent on adenosine analogues would correspond approximately to the xanthine 3-substituent in the xanthine-7-ribosides, minus the α-carbon which might occupy the space of the $N^6$-NH. A 3-benzyl group, as in 3-benzyl-1-butylxanthine-7-β-D-ribofuranoside, somewhat enhanced affinity at $A_1$ receptors, in parallel to the modest enhancement of affinity at $A_1$ receptors of $N^6$-phenyladenosine derivatives. Thus, at least some of the results set forth herein to describe the present invention are compatible with the hypothesis of a "flipped" overlap of purines.

However, there are possible differences between the two classes of nucleosides in structural determinants of affinity on the purine ring. At the purine 8-position, substitution is tolerated in $A_3$ receptor binding (8-methoxy) for xanthine ribosides but not for adenosine derivatives, as in 8-bromoadenosine. Similarly, it was recently reported that 8-alkylamino substitution of theophylline-7-riboside is tolerated at $A_1$ receptors (van der Wenden et al., *Drug Devel. Res.*, 31, 314 (1994)).

Also, implications for syn vs. anti modes of binding at $A_1$ and $A_2$ receptors have been derived from the affinity of the xanthine-7-ribosides, since the xanthine ribosides have a much stronger energetic preference for the anti-conformation than do adenosine derivatives. Thus, based on the absence of affinity of 8-bromoadenosine it is likely that the glycosidic conformation of adenosine binding at $A_3$ receptors is similar to that at $A_1$ receptors, i.e., in a non-syn-conformation. It is also possible that the orientation is not purely anti, since certain 8-substitution of the xanthine ribosides is tolerated.

Xanthine-7-ribosides were initially described as antagonists (van Galen et al., *Nucleosides & Nucleotides*, 10, 1191–1193 (1991)), but there have been some suggestions that theophylline-7-riboside is a partial agonist at $A_1$ receptors (Borea et al., *Int. J. Purine and Pyrimidine Res.*, 3, 65 (1992)), based on diminished shifts in binding in the presence of guanine nucleotides. It has also been noted that many adenosine derivatives display a correlation between lower affinity and partial agonism (Borea et al., *Eur. J. Pharmacol.* (Mol. Pharm. Section) (1994)). It is unknown whether the interconnection between intrinsic activity and affinity exists for this series of xanthine ribosides. 1,3-Dibutylxanthine-7-riboside has been found to be a partial agonist in the inhibition of adenylate cyclase via $A_3$ adenosine receptors, and a partial agonist may have therapeutic applications, based on the case of glycine receptors (von Lubitz et al., *Eur. J. Pharmacol.*, 219, 153 (1992)). Also, the exploration of partial agonists may lead to the development of antagonists (Jasper et al., *Biochem. Pharmacol.*, 43, 119–130 (1992)), which are lacking for $A_3$ receptors.

There are also common features between the structure activity relationships for dialkylxanthines binding to $A_3$ receptors and xanthine-7-ribosides. The 1,3-dibutyl analogues in both cases are the optimal chain length (for neutral molecules). A major difference is that for the xanthines, selectivity at the rat $A_3$ receptor was not achieved. At $A_1$ receptors, the xanthines are generally more potent than the xanthine-7-ribosides, while at rat $A_3$ receptors the converse is true. At other species, however, notably sheep and human $A_3$ receptors, certain xanthines, particularly those bearing negative charges, bind with high affinity.

For example, N-methyl 1,3-di-n-butylxanthine-7-β-D-ribofuronamide has been identified as a very selective ligand for $A_3$ receptors. Although it is not as potent as the adenosine derivative, IB-MECA (5'-N-methyl-$N^6$-(3-iodobenzyl) adenosine), it adds to the useful tools available for studying this newly cloned subtype. The indication that it is a partial agonist may be useful in studying receptor regulation, which is mainly unexplored for the $A_3$ receptor, and indicates that it may be useful in a therapeutic capacity as, for example, a neuroprotective agent (von Lubitz et al., *Neurosci. Abstr.* (1994)) and as an antiinflammatory agent (Beaven et al., *Trends Pharm. Sci.*, 15, 13–14 (1994)).

Compounds

The present invention provides a compound having the formula

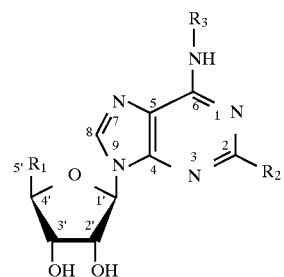

wherein $R_1$ is $R^aR^bNC(=O)$ or $HOR^c$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, $R_2$ is selected from the group consisting of hydrogen, halo, $C_1$–$C_{10}$ alkoxy, amino, $C_1$–$C_{10}$ alkylamino, $C_2$–$C_{10}$ alkenyl, $C_2$–$C_{10}$ alkynyl, thio, and $C_1$–$C_{10}$ alkylthio, and $R_3$ is selected from the group consisting of R- and S-1-phenylethyl, an unsubstituted benzyl group, and a phenylethyl or benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo. When $R_3$ is a substituted phenylethyl or benzyl group and there is more than one substituent on the phenylethyl or benzyl group, the substituents may be the same or different. Moreover, these compounds may be in the form of a suitable salt. For example, the sulfo-substituted derivative may be a salt, such as a triethylammonium salt.

These compounds are generally referred to as $N^6$-benzyladenosine-5'-N-uronamides and derivatives thereof and have been found to be $A_3$-selective adenosine receptor agonists. Preferred compounds include those of the above formula wherein $R_1$ is $R^aR^bNC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ is selected from the group consisting of hydrogen, halo, $C_1$–$C_{10}$ alkyoxy, amino, $C_2$–$C_{10}$ alkenyl, and $C_2$–$C_{10}$ alkynyl, and $R_3$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo. More preferred compounds include those of the above formula wherein $R^a$ and $R^b$ may be the same or different and are selected from the group consisting of hydrogen and $C_1$–$C_{10}$ alkyl, particularly when $R_2$ is hydrogen or halo, especially hydrogen. Additional preferred compounds are those compounds wherein $R^a$ is hydrogen and $R_2$ is hydrogen, particularly when $R_3$ is unsubstituted benzyl. More preferred compounds are such compounds wherein $R^b$ is a $C_1$–$C_{10}$ alkyl or $C_3$–$C_{10}$ cycloalkyl, particularly a $C_1$–$C_{10}$ alkyl, and more particularly methyl. Especially preferred are those compounds where $R^a$ is hydrogen, $R^b$ is $C_1$–$C_{10}$ alkyl or $C_3$–$C_{10}$ cycloalkyl, and $R_3$ is R- or S-1-phenylethyl or a benzyl substituted in one or more positions with a substituent selected from the group consisting of halo, amino, acetamido, $C_1$–$C_{10}$ haloalkyl, and sulfo, where the sulfo derivative is a salt, such as a triethylammonium salt. An example of an especially preferred compound is IB-MECA (as defined in Table 1 infra). In addition, those compounds in which $R_2$ is a $C_2$–$C_{10}$ alkyne of the formula R'—C≡C— where R' is a $C_1$–$C_8$ alkyl are particularly preferred. Also preferred are those compounds wherein $R_2$ is other than hydrogen, particularly those wherein $R_2$ is halo, $C_1$–$C_{10}$ alkylamino, or $C_1$–$C_{10}$ alkylthio, and, more preferably, when additionally $R^a$ is hydrogen, $R^b$ is a $C_1$–$C_{10}$ alkyl, and/or $R_3$ is a substituted benzyl. Such preferred compounds include 2-chloro-$N^6$-(3-iodobenzyl)-9-[5-(methylamido)-β-D-ribofuranosyl]-adenine, $N^6$-(3-iodobenzyl)-2-methylamino-9-[5-(methylamido)-β-D-ribofuranosyl]-adenine, and $N^6$-(3-iodobenzyl)-2-methylthio-9-[5-(methylamido)-β-D-ribofuranosyl]-adenine.

Compounds similar to those above, but which contain substituents in other positions, e.g., other than on the benzyl and/or uronamide groups, or in addition thereto, have also been found to be $A_3$-selective adenosine receptor agonists. Such compounds include those of the group consisting of $N^6$-benzyladenosine-5'-N-alkyluronamide-$N^1$-oxide and $N^6$-benzyladenosine-5'-N-dialkyluronamide-$N^1$-oxide. 2-purine substitutions, such as $C_1$–$C_{10}$ alkyloxy, amino, $C_2$–$C_{10}$ alkenyl, $C_2$–$C_{10}$ alkynyl, and especially halo, e.g., chloro, do not adversely affect the activity of these compounds.

The present invention further provides a modified xanthine-7-riboside, particularly a compound having the formula

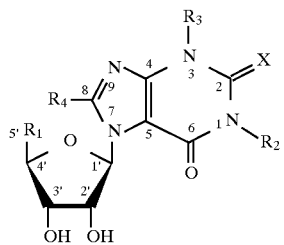

wherein X is O or S, $R_1$ is $R^a R^b NC(=O)$ or $HOR^c$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, $R_2$ and $R_3$ may be the same or different and are selected from the group consisting of $C_1$–$C_{10}$ alkyl, R- and S-1-phenylethyl, an unsubstituted benzyl group, and a phenylether or benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo, and $R_4$ is selected from the group consisting of halo, benzyl, phenyl, $C_3$–$C_{10}$ cycloalkyl, and $C_1$–$C_{10}$ alkoxy, with the proviso that if X=O, $R_1$ is $HOCH_2$, and $R_4$=H, then $R_2$ and $R_3$ are not $C_1$–$C_4$ alkyl, preferably not $C_1$–$C_{10}$ alkyl (although the compounds covered by the proviso are useful in the present inventive method described herein). Particularly preferred are those compounds wherein X is O, $R_1$ is $R^a R^b NC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ and $R_3$ may be the same or different and are selected from the group consisting of $C_1$–$C_{10}$ alkyl, R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo, and $R_4$ is selected from the group consisting of halo, benzyl, phenyl, and $C_3$–$C_{10}$ cycloalkyl.

The compounds of the present invention may be used as is or in the form of their pharmaceutically acceptable salts and derivatives, and can be used alone or in appropriate combination with one or more other compounds/derivatives of the present invention or other active compounds. It should be understood, however, that the salt or derivative should not be one that renders the compound unstable or insoluble in water or toxic at contemplated doses. The potency of the present compounds as adenosine receptor antagonists can be determined by standard screening procedures (Bruns et al., *PNAS USA,* 77(9), 5547–5551 (September 1980)).

Abbreviations

The following abbreviations are used herein in the course of further describing the present invention:

AB-MECA $N^6$-(4-amino-3-iodobenzyl)adenosine-5'-N-methyluronamide
ADAC $N^6$-[4-[[[4-[[[(2-aminoethyl)amino]carbonyl]methyl]anilino]carbonyl]methyl]phenyl]adenosine
AMP adenosine-5'-monophosphate
APNEA $N^6$-2-(4-aminophenyl)ethyladenosine
CPX 8-cyclopentyl-1,3-dipropylxanthine
CGS 15943 9-chloro-2-(2-furyl) [1,2,4]triazolo[1,5-c]quinazolin-5-amine
CGS 21680 2-[4-(2-carboxyethyl)phenyl]ethylamino 5'-N-ethylcarboxamidoadenosine
CHA $N^6$-cyclohexyladenosine
CP66713 4-amino-8-chloro-1-phenyl[1,2,4]-triazolo [4,3-a]quinoxaline
CPA $N^6$-cyclopentyladenosine
CSC 8-(3-chlorostyryl)caffeine
CV-1808 2-(phenylamino)adenosine
DBXR 1,3-dibutylxanthine-7-riboside
DCCA 1-deaza-2-chloro-$N^6$-cyclopentyladenosine
DMAP 4-(N,N-dimethylamino)pyridine
DMF N,N-dimethylformamide
DMSO dimethylsulfoxide
DPMA $N^6$-[2-(3,5-dimethoxyphenyl)-2-(2-methylphenyl)ethyl]adenosine
EDAC 1-(3-dimethylaminopropyl)-3-ethylcarbodiimide hydrochloride
EHNA erythro-9-(2-hydroxy-3-nonyl)adenine
HMDS 1,1,1,3,3,3-hexamethyldisilazane
IB-MECA $N^6$ (3-iodobenzyl)adenosine-5'-N-methyluronamide
IBMX 3-isobutyl-1-methylxanthine
IQA imidazo[4,5-c]quinolin-4-amine
NBTI $N^6$-(4-nitrobenzyl)thioinosine
NECA 5'-N-ethylcarboxamidoadenosine
NMCA 5'-N-methylcarboxamidoadenosine
NMCI 5'-N-methylcarboxamidoinosine
NECI 5'-N-ethylcarboxamidoinosine
PIA R-$N^6$-phenylisopropyladenosine
R/S-PIA $N^6$-[(R/S)-1-methyl-2-phenylethyl]adenosine
SPA $N^6$-(p-sulfophenyl)adenosine
TBAF tetrabutylammonium fluoride
THF tetrahydrofuran
TMSOTf trimethylsilyl trifluoromethanesulfonate
Tris tris(hydroxymethyl)aminomethane
XAC 8-{4-[({[(2-aminoethyl)amino]carbonyl}methyl)oxy]phenyl}-1,3-dipropylxanthine Compound Synthesis The compounds of the present invention, including those useful in the present inventive compositions and methods, may be synthesized by any suitable means. The compounds of the present invention are preferably synthesized by the following Reaction Scheme A.
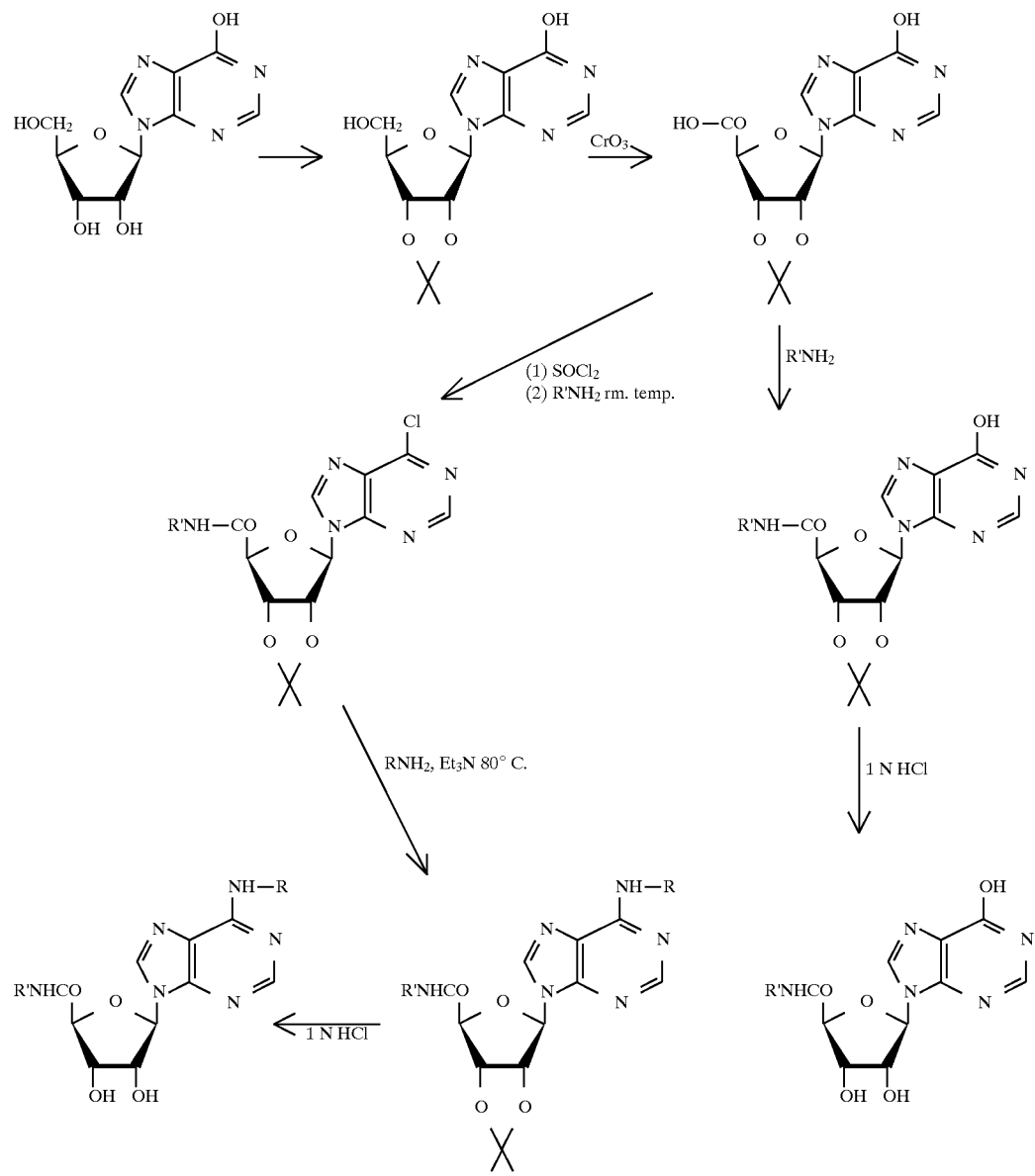
The compounds of the present invention may also be synthesized by a Dimroth rearrangement as set forth in the following Reaction Scheme B.
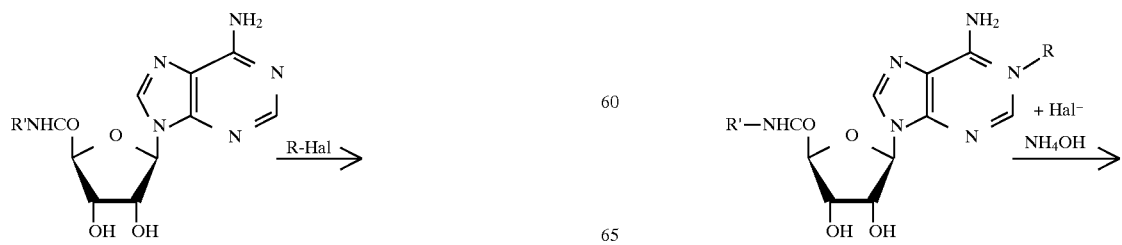

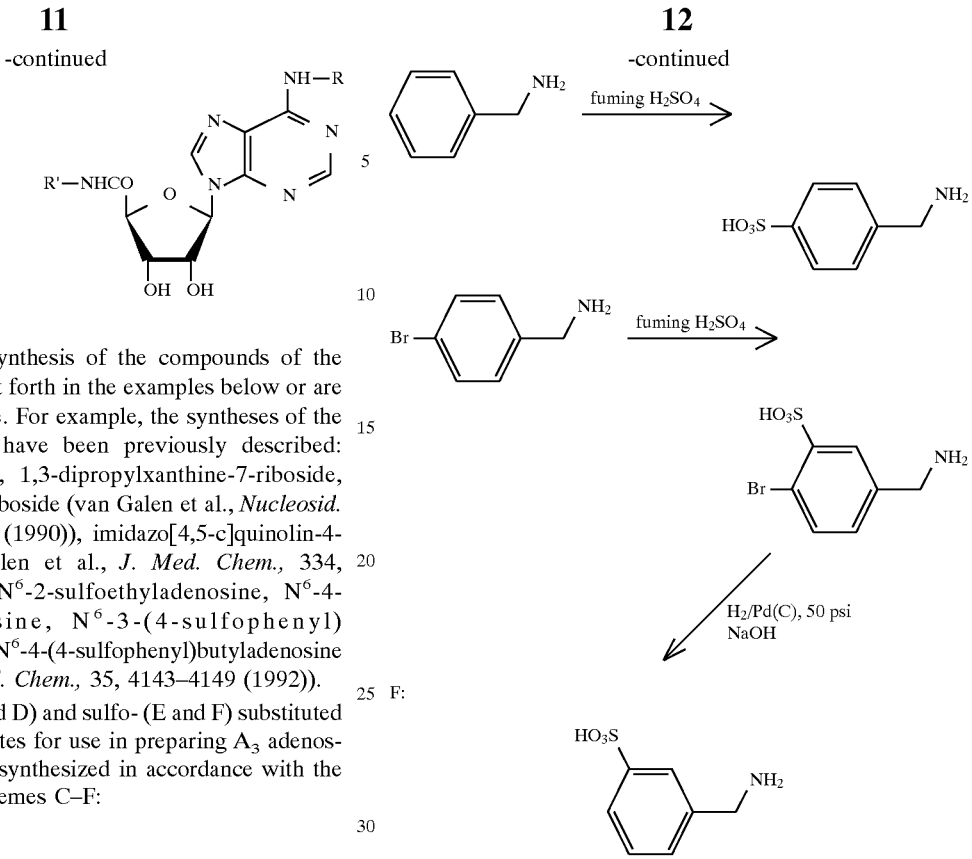

The details of the synthesis of the compounds of the present invention are set forth in the examples below or are reported in the literature. For example, the syntheses of the following compounds have been previously described: theophylline-7-riboside, 1,3-dipropylxanthine-7-riboside, 1,3-dibutylxanthine-7-riboside (van Galen et al., *Nucleosid. Nucleotid.*, 9, 275–291 (1990)), imidazo[4,5-c]quinolin-4-amine (IQA) (van Galen et al., *J. Med. Chem.*, 334, 1202–1206 (1991)), $N^6$-2-sulfoethyladenosine, $N^6$-4-sulfophenyladenosine, $N^6$-3-(4-sulfophenyl)propyladenosine, and $N^6$-4-(4-sulfophenyl)butyladenosine (Jacobson et al., *J. Med. Chem.*, 35, 4143–4149 (1992)).

Various amino- (C and D) and sulfo- (E and F) substituted benzylamine intermediates for use in preparing $A_3$ adenosine agonists have been synthesized in accordance with the following Reaction Schemes C–F:

$N^6$-(3-aminobenzyl)-NMCA and $N^6$-(4-aminobenzyl)-NMCA, respectively, have been prepared by treatment of the 6-chloropurine intermediate (R'=CH$_3$) with 3- or 4-aminobenzylamine. The intermediate 3-aminobenzylamine has been prepared via catalytic reduction of the 3-nitro derivative as shown in reaction scheme A above. The nucleophilic attack of the purine ring occurs selectively at the aryl amine. Since $N^6$-(4-aminobenzyl)-NMCA has been prepared as a precursor for radioiodination, the expected major product of direct iodination, 3-iodo-4-aminobenzyl-adenosine-5'-N-methyluronamide, has been prepared as a standard for purification and pharmacology. The disubstituted benzylamine intermediate has been prepared via protection of the alkylamine as the t-butyloxycarbonyl derivative as shown in Reaction Scheme D above. The $N^6$-(4-aminobenzyl)-NMCA has been also N-acetylated at the 2',3'-isopropylidene protected stage using acetic anhydride to yield $N^6$-(3-acetamido)-NMCA after deprotection. Two sulfo analogues, namely $N^6$-(3-sulfobenzyl)-NMCA and $N^6$-(4-sulfobenzyl)-NMCA have been prepared as shown above in Reaction Scheme F above. The 4-sulfo derivative has been prepared from an intermediate above prepared directly from benzylamine as shown in reaction scheme E above. The 3-sulfo intermediate leading to $N^6$-(3-sulfobenzyl)-NMCA has been prepared via sulfonation of 4-bromobenzylamine followed by catalytic hydrogenation in basic medium as shown in reaction scheme F above.

5'-N-Boc-aminoethylamino-CA, which binds weakly but selectively to $A_3$ receptors, has been synthesized as shown in Reaction Scheme G below.

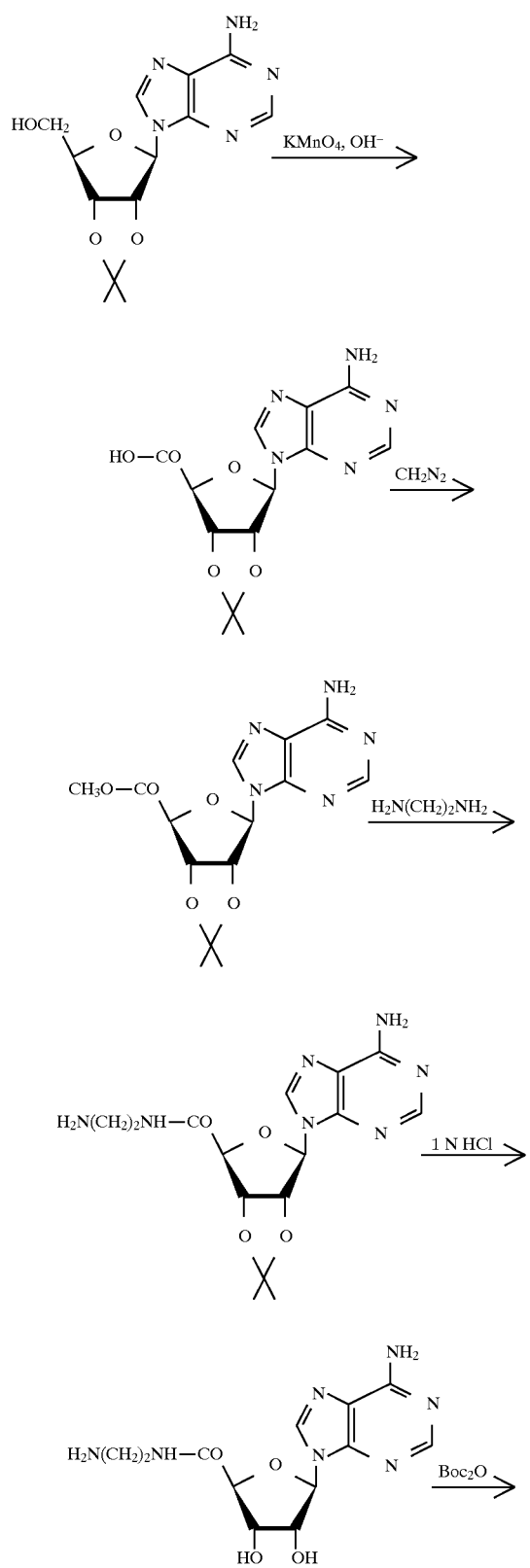
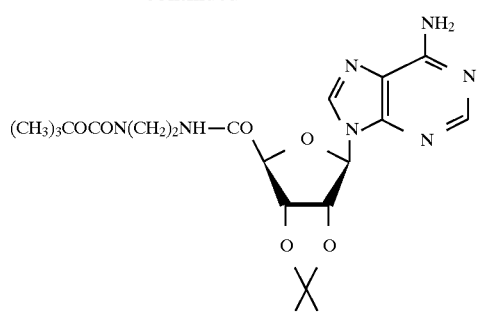
Modified ribosides to be used in the present inventive methods can be synthesized in accordance with the following Reaction Schemes H and I, respectively:
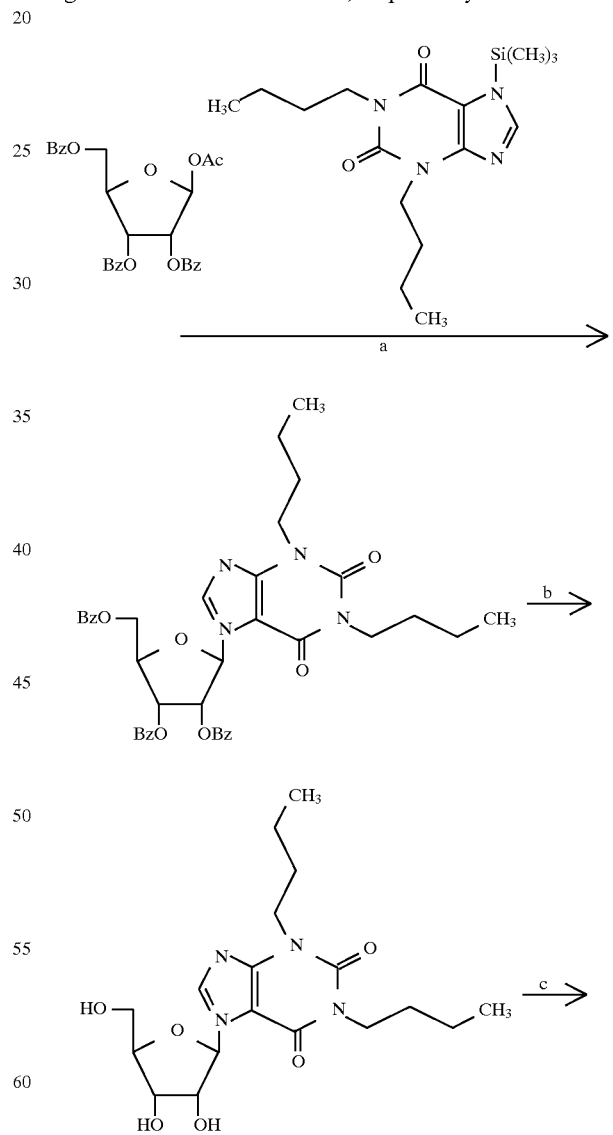

15

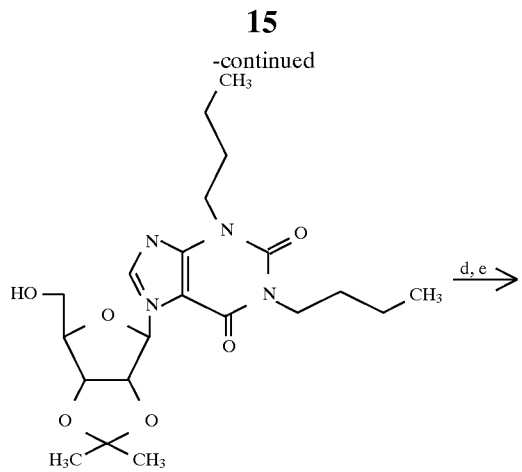

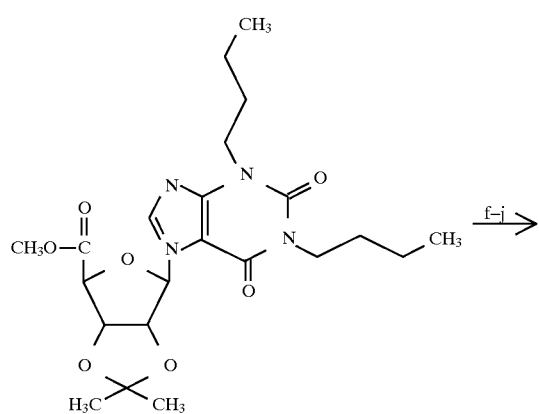

16

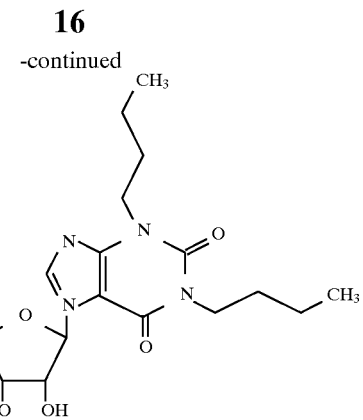

wherein the reagents and conditions are as follows:

(a) potassium nonaflate, SiCl$_3$, CH$_3$CN
(b) NH$_3$/MeOH
(c) p-TsOH, acetone
(d) RuCl$_3$, NaIO$_4$, CHCl$_3$:CH$_3$CN:H$_2$O (2:2:3)
(e) EDAC, DMAP, MeOH
(f) 88% HCO$_2$H
(g) i, MeNH$_2$, MeOH, 85° C.; ii, 88% HCO$_2$H
(h) i, NH$_3$, MEOH, 85° C.; ii, 88% HCO$_2$H
(i) i, EtNH$_2$, MeOH, 85° C.; ii, 88% HCO$_2$H
(j) i, Me$_2$NH, MeOH, 85° C.; ii, 88% HCO$_2$H;

or

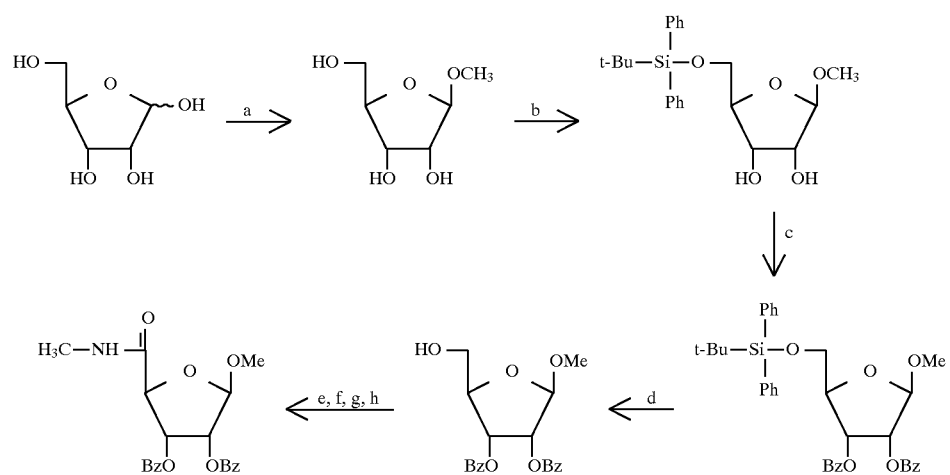

wherein the reagents and conditions are as follows:
(a) HCl, MeOH, room temperature, overnight
(b) TBDPSiCl, DMAP, DMF, room temperature
(c) Bz$_2$O, pyr.
(d) n-BU$_4$NF, THF (e) RuO$_2$, NaIO$_4$, CHCl$_3$:CH$_3$CN:H$_2$O (2:2:3)
(f) EDAC, DMAP, MeOH
(g) MeNH$_2$, MeOH, 75° C.
(h) BzCl, pyr-CH$_2$Cl$_2$, with the methyl substituent being capable of conversion to an acetate for further reaction by techniques well known in the art.

1,3-Dibutyl-xanthine may be synthesized according to the procedure set forth in Jacobson et al., *J. Med. Chem.*, 28, 1334–1340 (1985).

The triple substitution of adenosine, i.e., at 5'-, 2-, and $N^6$-positions, can be carried out by a synthetic strategy in which a 5'-uronamide sugar moiety is condensed with a purine moiety, such as a substituted adenosine derivative. The key sugar intermediate, N-methyl 1-O-acetyl-2,3-dibenzoyl-β-D-ribofuronamide, was synthesized starting from methyl β-D-ribofuranoside, which is commercially available or can be synthesized from D-ribose (Baker et al., *J. Org. Chem.*, 26, 4605–4609 (1961)), in 8 steps. The primary alcohol of β-D-ribofuranoside can be selectively protected with tert-butyldiphenylsilyl chloride (Chaudhary et al., *Tet. Lett.*, 20(2), 99–102 (1979)) to provide 1-O-methyl 5-(t-butyldiphenylsilyl)-β-D-ribofuranoside, and other alcohols can be followed with benzoyl protection to provide 1-O-methyl 5-(t-butyldiphenylsilyl)-2,3-dibenzoyl-β-D-ribofuranoside, the desilylation of which with TBAF/THF will give 1-O-methyl 2,3-dibenzoyl-β-D-ribofuranoside. The 5'-position of 1-O-methyl 2,3-dibenzoyl-β-D-ribofuranoside can be oxidized using ruthenium tetroxide (Singh et al., *Tet. Lett.*, 33(17), 2307–2310 (1992)) to yield 1-O-methyl-2,3-dibenzoyl-β-D-ribofuronic acid which can be purified after methylation on a silica gel column chromatography. Methylamide at 5-position can be introduced by nucleophilic displacement of methyl 1-O-methyl-2,3-dibenzoyl-β-D-ribofuronate with methylamine in THF and benzoyl reprotection of resulting 2,3-diol to yield the sugar intermediate N-methyl 1-O-acetyl-2,3-dibenzoyl-β-D-ribofuronamide.

$N^6$-(3-iodobenzyl)-2-substituted adenosine derivatives can be synthesized from the corresponding adenine derivative. 2,6-Dichloropurine reacted with 3-iodobenzylamine hydrochloride in the presence of triethylamine in ethanol at room temperature provides $N^6$-(3-iodobenzyl)-2-chloroadenine, which can be silylated before coupling to yield the silylated derivative. The glycosidic bond is formed upon treatment of the 1'-O-acetyl riboside derivative N-methyl 1-O-acetyl-2,3-dibenzoyl-β-D-ribofuronamide with the aforesaid 9-silylated adenine derivative in the presence of TMSOTf as a Lewis acid catalyst. Condensation of N-methyl 1-O-methyl-2,3-dibenzoyl-β-D-ribofuronamide with the aforesaid 9-silylated adenine derivative produces ribose ring-opened product. Benzoyl groups of 2-chloro-$N^6$-(3-iodobenzyl)- 9-[5-(methylamido)-2,3-di-O-benzoyl-β-D-ribofuranosyl]-adenine are deprotected with $NH_3$/MeOH to produce 2-chloro-$N^6$-(3-iodobenzyl)-9-[5-(methylamido)-β-D-ribofuranosyl]-adenine, which reacted with various nucleophiles such as methylamine/THF and sodium thiomethoxide/DME yield compounds $N^6$-(3-iodobenzyl)-2-methylamino-9-[5-(methylamido)-β-D-ribofuranosyl]-adenine and $N^6$-(3-iodobenzyl)-2-methylthio-9-[5-(methylamido)-β-D-ribofuranosyl]-adenine. The benzoyl groups of 2-chloro-$N^6$-(3-iodobenzyl)-9-[2,3,5-tri-O-benzoyl-β-D-ribofuranosyl]-adenine can be similarly deprotected to produce the riboside derivative 2-chloro-$N^6$-(3-iodobenzyl)-9-[β-D-ribofuranosyl]-adenine.

Parallel substitutions of xanthine-7-ribosides and related analogues can be similarly carried out. The synthesis of theophylline-7-riboside and other xanthine glycosides has been described (van Galen et al., *Nucleosides & Nucleotides*, 9, 275–291 (1990); van Galen et al., *Nucleo-*

*sides & Nucleotides*, 10, 1191–1193 (1991); Ozola et al., *Nucleosides & Nucleotides*, 12, 479–486 (1991)). Silylated xanthines can be condensed with 1-acetyl-2,3,5-tri-O-benzoyl-ribofuranoside using potassium nonaflate and trichlorosilane as Lewis acid catalyst. Unsymmetrical 1,3-disubstitution is accomplished by glycosylation of a mixture of 1-benzyl-3-butylxanthine and 3-benzyl-1-butylxanthine with 1-acetyl-2,3,5-tri-O-benzoyl-ribofuranoside followed by chromatographic separation and fractional crystalization of the isomers. As shown in Reaction Scheme J below, debenzoylation of intermediates a–g with methanolic ammonia produces the indicated xanthine ribosides, whereas intermediate h, if desired, can be converted into the corresponding methoxy derivative.

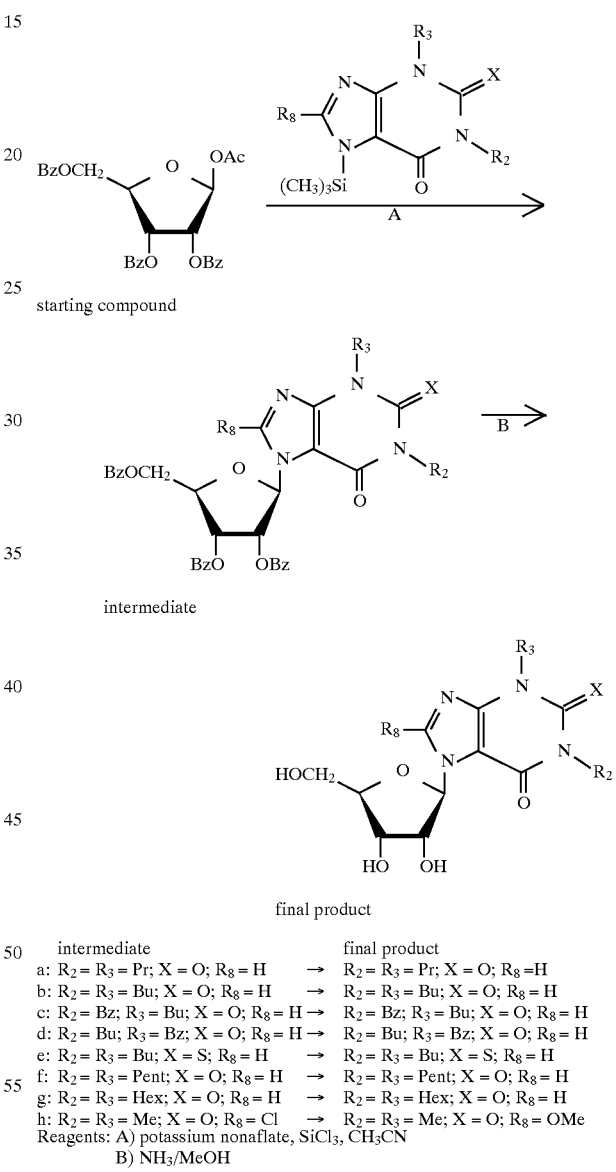

starting compound intermediate final product

| | intermediate | | final product |
|---|---|---|---|
| a: | $R_2 = R_3 = Pr; X = O; R_8 = H$ | → | $R_2 = R_3 = Pr; X = O; R_8 = H$ |
| b: | $R_2 = R_3 = Bu; X = O; R_8 = H$ | → | $R_2 = R_3 = Bu; X = O; R_8 = H$ |
| c: | $R_2 = Bz; R_3 = Bu; X = O; R_8 = H$ | → | $R_2 = Bz; R_3 = Bu; X = O; R_8 = H$ |
| d: | $R_2 = Bu; R_3 = Bz; X = O; R_8 = H$ | → | $R_2 = Bu; R_3 = Bz; X = O; R_8 = H$ |
| e: | $R_2 = R_3 = Bu; X = S; R_8 = H$ | → | $R_2 = R_3 = Bu; X = S; R_8 = H$ |
| f: | $R_2 = R_3 = Pent; X = O; R_8 = H$ | → | $R_2 = R_3 = Pent; X = O; R_8 = H$ |
| g: | $R_2 = R_3 = Hex; X = O; R_8 = H$ | → | $R_2 = R_3 = Hex; X = O; R_8 = H$ |
| h: | $R_2 = R_3 = Me; X = O; R_8 = Cl$ | → | $R_2 = R_3 = Me; X = O; R_8 = OMe$ |

Reagents: A) potassium nonaflate, $SiCl_3$, $CH_3CN$
B) $NH_3$/MeOH

In order to synthesize 5'-modified xanthine nucleosides, 2'- and 3'-hydroxyl groups were selectively protected by isopropylidenation. Oxidation of the 5'-hydroxyl group was accomplished under mild conditions using ruthenium chloride, in a procedure modified from Singh et al., *Tetrahedron Letters*, 33, 2307–2310 (1992). When 0.1 equivalent of ruthenium chloride is used, as described in the literature, deglycosylation is observed, and the reaction cannot be controlled. Reduction of the number of equivalents to 0.01 resulted in an increase in reaction time and a decrease in deglycosylation.

Esterification of the 5'-carboxylic acid was accomplished by a modification of the Hassner procedure. The methyl ester can be purified by silica gel column chromatography. The replacement of the methyl ester group with several nucleophiles, such as methylamine, ammonia, dimethylamine, and ethylamine, followed by deisopropylidenation, produces 5'-modified xanthine ribosides, such as those of Examples 65–67 and 69–71. For the preparation of 8-substituted xanthine ribosides bromination using bromine, or N-bromosuccinimide (NBS), can be utilized on 1,3-dibutyl-7-[2,3-isopropylidene-5-(methylamido)-β-D-ribofuranosyl]-xanthine, 1,3-dipentylxanthine-riboside, or 2',3',5'-triacetyl-1,3-dipentyl-xanthine-riboside. Direct condensations of 8-substituted-1,3-dibutylxanthine with the riboside sugar of Reaction Scheme J above (i.e., the starting compound) under similar condensation condition can also be attempted. However, substitutions of the 8-position on xanthine are not entirely successful, probably due to steric hindrance of 1-butyl or 1-pentyl group. Changing the substituents at the 1- and 3-positions of xanthine from butyl or pentyl to methyl group allowed the condensation to work. Thus the aforesaid riboside sugar was condensed with 8-chloro-theophylline under similar condensation conditions to give intermediate h, which was converted to the 8-methoxy derivative 8-methoxytheophylline-7-β-D-ribofuranoside in $NH_3$/MeOH.

Pharmaceutical Compositions

The present invention also provides a pharmaceutical composition comprising a pharmaceutically acceptable carrier and an effective amount, e.g., a therapeutically effective amount, including a prophylactically effective amount, of one or more of the aforesaid compounds.

The carrier can be any of those conventionally used and is limited only by chemico-physical considerations, such as solubility and lack of reactivity with the compound, and by the route of administration. It will be appreciated by one of skill in the art that, in addition to the following described pharmaceutical compositions, the compounds of the present invention can be formulated as inclusion complexes, such as cyclodextrin inclusion complexes, or liposomes.

Examples of pharmaceutically acceptable acid addition salts for use in the present inventive pharmaceutical composition include those derived from mineral acids, such as hydrochloric, hydrobromic, phosphoric, metaphosphoric, nitric and sulphuric acids, and organic acids, such as tartaric, acetic, citric, malic, lactic, fumaric, benzoic, glycolic, gluconic, succinic, and arylsulphonic, for example p-toluenesulphonic, acids.

The pharmaceutically acceptable carriers described herein, for example, vehicles, adjuvants, excipients, or diluents, are well-known to those who are skilled in the art and are readily available to the public. It is preferred that the pharmaceutically acceptable carrier be one which is chemically inert to the active compounds and one which has no detrimental side effects or toxicity under the conditions of use.

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intramuscular, interperitoneal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

The compounds of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compounds of the present invention may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238–250 (1982), and *ASHP Handbook on Injectable Drugs*, Toissel, 4th ed., pages 622–630 (1986).

Additionally, the compounds of the present invention may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Methods of Use

In addition, the present invention provides a method of selectively activating $A_3$ adenosine receptors in a mammal, which method comprises acutely or chronically administering to a mammal in need of selective activation of its $A_3$ adenosine receptors a therapeutically effective amount, including a prophylactically effective amount, of a compound which binds with the $A_3$ receptor so as to stimulate an $A_3$ receptor-dependent response.

Preferred compounds for use in the present inventive method include those compounds described above and compounds having the formula

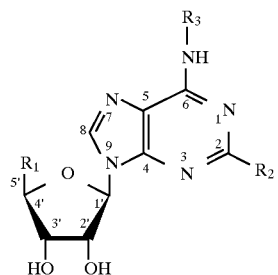

wherein $R_1$ is $R^a R^b NC(=O)$ or $HOR^c$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ is selected from the group consisting of hydrogen, halo, $C_1$–$C_{10}$ alkyloxy, amino, $C_1$–$C_{10}$ alkylamino, $C_2$–$C_{10}$ alkenyl, $C_2$–$C_{10}$ alkynyl, thio, and $C_1$–$C_{10}$ alkylthio, and $R_3$ is selected from the group consisting of R- and S-1-phenylethyl, an unsubstituted benzyl group, and a phenylethyl or benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo. More preferred compounds include those compounds wherein $R_1$ is $R^a R^b NC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, and $C_3$–$C_{10}$ cycloalkyl, $R_2$ is selected from the group consisting of hydrogen, halo, $C_1$–$C_{10}$ alkyloxy, amino, $C_2$–$C_{10}$ alkenes, and $C_2$–$C_{10}$ alkynyl, and $R_3$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo. Additional preferred compounds include those compounds wherein $R^a$ is hydrogen and $R^b$ is selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, and even more preferably $R^a$ is hydrogen and $R^b$ is a $C_1$–$C_{10}$ alkyl, $C_3$–$C_{10}$ cycloalkyl, $C_1$–$C_{10}$ aminoalkyl, or $C_1$–$C_{10}$ boc-aminoalkyl. Especially preferred are those compounds wherein $R^a$ is hydrogen and $R^b$ is a $C_1$–$C_{10}$ alkyl, such as methyl or ethyl, a $C_3$–$C_{10}$ cycloalkyl, such as cyclopropyl, a $C_1$–$C_{10}$ aminoalkyl, such as aminoethyl, and a $C_1$–$C_{10}$ boc-aminoalkyl, such as boc-aminoethyl. Particularly preferred compounds include 5'-N-aminoethylaminocarboxamidoadenosine and 5'-N-boc-aminoethylaminocarboxamidoadenosine.

Also useful in the context of the present inventive method are those compounds having the formula

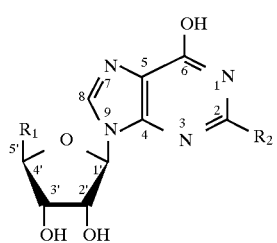

wherein $R_1$ is $R^a R^b NC(=O)$ or $HOR^c$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, or are joined together to form a heterocyclic ring containing two to five carbon atoms, and $R^c$ is selected from the group consisting of $C_1$–$C_{10}$ alkyl, amino, $C_1$–$C_{10}$ haloalkyl, $C_1$–$C_{10}$ aminoalkyl, and $C_3$–$C_{10}$ cycloalkyl, and $R_2$ is selected from the group consisting of hydrogen, halo, $C_1$–$C_{10}$ alkylethers, amino, $C_1$–$C_{10}$ alkylamino, $C_2$–$C_{10}$ alkenes, $C_2$–$C_{10}$ alkynes, thio, and $C_1$–$C_{10}$ alkylthio. More preferred are those compounds wherein $R_1$ is $R^a R^b NC(=O)$, wherein $R^a$ and $R^b$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, and $R_2$ is selected from the group consisting of hydrogen, halo, $C_1$–$C_{10}$ alkyloxy, amino, $C_2$–$C_{10}$ alkenyl, and $C_2$–$C_{10}$ alkynyl. Most preferred are those compounds wherein $R^a$ is hydrogen and $R_2$ is hydrogen, particularly when $R^b$ is hydrogen, a $C_1$–$C_{10}$ alkyl, such as methyl or ethyl, a $C_3$–$C_{10}$ cycloalkyl, such as cyclopropyl, a $C_1$–$C_{10}$ aminoalkyl, a $C_1$–$C_{10}$ aminoethyl, or a $C_1$–$C_{10}$ boc-aminoalkyl, such as boc-aminoethyl. Such preferred compounds include 5'-N-aminoethylaminocarboxamidoadenosine and 5'-N-boc-aminoethylaminocarboxamidoadenosine.

In addition to the modified xanthine-7-ribosides disclosed above, other preferred modified xanthine-7-ribosides can also be used in the present inventive method. Such a modified xanthine-7-riboside is 1,3-$R_1R_2$-xanthine-7-riboside, wherein $R_1$ and $R_2$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, benzyl, and $C_3$–$C_{10}$ cycloalkyl, or, less preferably, are joined together to form a heterocyclic ring containing two to five carbon atoms. Especially preferred such compounds include 1,3-dialkylxanthine-7-ribosides, particularly 1,3-dibutylxanthine-7-riboside. Another modified xanthine-7-riboside which can be used in the present inventive method is 5'-$R_3$-1,3-$R_1R_2$-xanthine-7-riboside, wherein $R_1$ and $R_2$ may be the same or different and are selected from the group consisting of hydrogen, $C_1$–$C_{10}$ alkyl, amino, $C_1$–$C_{10}$ haloalkyl, $C_1$–$C_{10}$ aminoalkyl, benzyl, and $C_3$–$C_1O$ cycloalkyl, or, less preferably, are joined together to form a heterocyclic ring containing two to five carbon atoms, and $R_3$ is selected from the group consisting of $C_1$–$C_{10}$ alkoxycarbonyl and aminocarbonyl, wherein the amino group is substituted at one or more positions with a $C_1$–$C_{10}$ alkyl. Especially preferred compounds of this latter group include 5'-$R_3$-1,3-dibutylxanthine-7-riboside, particularly 5'-methylaminocarbonyl-1,3-dibutylxanthine-7-riboside.

The compounds of the present invention can be utilized in vitro for scientific and research purposes. For example, the present invention provides an assay, which comprises providing one of the aforesaid compounds, which has been suitably labeled, contacting a sample with the labeled compound under conditions sufficient to effect binding between the labeled compound and a component of the sample, and determining whether any binding occurred. The compounds of the present invention, such as 5'-N-methyl-$N^6$-(3-halobenzyl) adenosine 5'-N-methyl uronamides and iodinatable aryl amines (e.g., compounds 44 and 50 in Table 1, infra), may be used to probe $A_3$ adenosine receptors in order to isolate or characterize the receptors, including their physiological role, distribution, and regulation. In particular, the compounds of the present invention may be labeled, e.g., radioiodinated, for photoaffinity crosslinking to the receptor protein. The crosslinking to the receptor can be carried out with the photoaffinity crosslinking reagent SANPAH (N-succinimidyl-6(4'-azido-2'-nitro-phenyl-amino) hexanoate) or by conversion of the aryl amino group to an azide, followed by photolysis in the presence of the receptor. Alternatively, a chemically reactive bifunctional reagent, such as p-phenylene diisothiocyanate, can be coupled to the amine congener, in a manner that leaves one electrophilic group unreacted. Another type of label or reporter group, a fluorescent dye, such as fluorescein isothiocyanate, may be coupled to an amine congener to provide an affinity probe. These probes obviate the need for radioactive ligands for receptor characterization in studies utilizing membrane homogenates and tissue slices. A suitable reaction scheme for labeling a compound of the present invention, wherein R'=methyl is preferred, is set forth below as Reaction Scheme K.

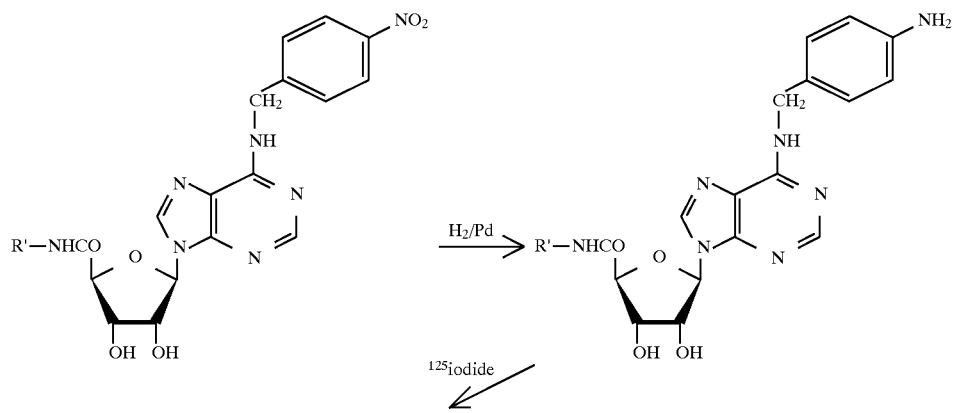

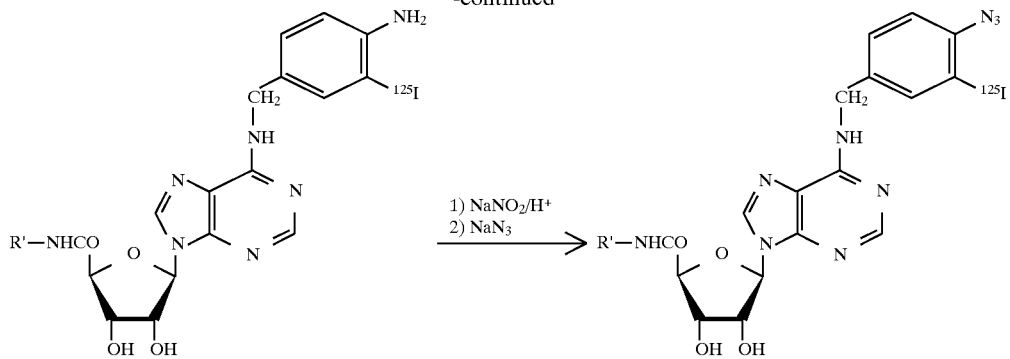

A compound of the present invention can be also linked to an amine functionalized agarose matrix for affinity chromatography involving the $A_3$-receptor.

The method of the present invention has particular usefulness in in vivo applications. For example, $A_3$ adenosine receptor agonists can be used in the treatment of any disease state or condition involving the release of inositol-1,4,5-triphosphate (IP3), diacylglycerol (DAG), and free radicals and subsequent arachidonic acid cascades. Thus, high blood pressure, locomotor hyperactivity, hypertension, acute hypoxia, depression, and infertility can be treated in accordance with the present inventive method, wherein one of the above-described compounds is acutely administered, e.g., within about a few minutes to about an hour of the onset or realization of symptoms. The method also has utility in the treatment of chronic disease states and conditions, in particular those conditions and disease states wherein chronic prophylactic or therapeutic administration of one of the above-described compounds will prevent the onset of symptoms or will reduce recovery time. Examples of disease states and conditions that may be chronically treated in accordance with the present inventive method include inflammatory disorders, such as vascular inflammation and arthritis, allergies, asthma, wound healing, stroke, cardiac failure, acute spinal cord injury, acute head injury or trauma, seizure, neonatal hypoxia (cerebral palsy; prophylactic treatment involves chronic exposure through placental circulation), chronic hypoxia due to arteriovenous malformations and occlusive cerebral artery disease, severe neurological disorders related to excitotoxicity, Parkinson's disease, Huntington's chorea, and other diseases of the central nervous system (CNS), cardiac disease, kidney disease, and contraception.

Moreover, the above compounds have been found to increase basal or systemic blood pressure, and thus the chronic administration of these compounds can be used to treat malignant hypotension. For example, the administration of IB-MECA results in a significant increase (e.g., about 10–30%) in basal or systemic blood pressure (e.g., from about 70 mm Hg to about 90 mm Hg).

Such compounds have also been found to be significant cerebral protectants. As such, the above compounds can be used to treat and/or protect against a variety of disorders, including, for example, seizures, transient ischemic shock, strokes, focal ischemia originating from thrombus or cerebral hemorrhage, global ischemia originating from cardiac arrest, trauma, neonatal palsy, hypovolemic shock, and hyperglycemia and associated neuropathies. The above compounds, particularly, for example, IB-MECA, have also been found to have precognitive effects and, therefore, can be used in the treatment of disorders wherein the elicitation of such an effect would prove useful, such as in the treatment of Alzheimer's disease and other dementing and cognitive disorders.

Although any of the above compounds may be administered chronically, the above-described modified xanthine-7-ribosides are preferred for chronic dosage regimens. Modified xanthine-7-ribosides are preferred in the present inventive method necessitating chronic administration because their use under such conditions is generally not accompanied by the adverse side-effects typically encountered with other compounds. For example, 1,3-dibutyl-xanthine-riboside had a shallow dose response curve in inhibition of adenylate cyclase in CHO cells stably transfected with rat $A_3$ adenosine receptor cDNA (in comparison with $N^6$-benzyl-NECA or $N^6$-cyclohexyl-NECA). Therefore, these derivatives are partial agonists and, as such, produce desensitization of the receptor without the side-effects of acute administration. Cf. von Lubitz et al., *Eur. J. Pharmacol.*, 219, 153–158 (1993).

The present inventive method includes the administration to an animal, such as a mammal, particularly a human, in need of the desired $A_3$ receptor-dependent response of an effective amount, e.g., a therapeutically effective amount, of one or more of the aforementioned present inventive compounds or pharmaceutically acceptable salts or derivatives thereof, alone or in combination with one or more other pharmaceutically active compounds.

Some of the compounds of the present invention can be utilized as functionalized congeners for coupling to other molecules, such as amines and peptides. The use of such congeners provide for increased potency, prolonged duration of action, specificity of action, and prodrugs. Water solubility is also enhanced, which allows for reduction, if not complete elimination, of undesirable binding to plasma proteins and partition into lipids. Accordingly, improved pharmacokinetics can be realized.

One skilled in the art will appreciate that suitable methods of administering a compound of the present invention to an animal are available, and, although more than one route can be used to administer a particular compound, a particular route can provide a more immediate and more effective reaction than another route. Accordingly, the above-described methods are merely exemplary and are in no way limiting.

The dose administered to an animal, particularly a human, in the context of the present invention should be sufficient to effect a prophylactic or therapeutic response in the animal over a reasonable time frame. One skilled in the art will recognize that dosage will depend upon a variety of factors including the strength of the particular compound employed, the age, species, condition, and body weight of the animal, as well as the severity/stage of the disease or condition. The size of the dose will also be determined by the route, timing and frequency of administration as well as the existence, nature, and extent of any adverse side-effects that might accompany the administration of a particular compound and the desired physiological effect. It will be appreciated by one of skill in the art that various conditions or disease states, in particular chronic conditions or disease states, may require prolonged treatment involving multiple administrations.

Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments until the optimum effect under the circumstances is reached. For convenience, the total daily dosage may be divided and administered in portions during the day if desired. In proper doses and with suitable administration of certain compounds, the present invention provides for a wide range of selective $A_3$ receptor-dependent responses. Exemplary dosages range from about 0.1 to about 100 mg/kg body weight of the animal being treated/day. Therapeutically effective dosages range from about 0.01 to about 10 mg/kg body weight/day.

EXAMPLES

The following examples further illustrate the present invention and, of course, should not be construed as in any way limiting its scope. In the examples, unless otherwise noted, compounds were characterized and resonances assigned by 300 MHz proton nuclear magnetic resonance mass spectroscopy using a Varian GEMINI-300 FT-NMR spectrometer. Also, unless noted otherwise, chemical shifts are expressed as ppm downfield from tetramethylsilane. Synthetic intermediates were characterized by chemical ionization mass spectrometry (NH3) and adenosine derivatives by fast atom bombardment mass spectrometry (positive ions in a noba or m-bullet matrix) on a JEOL SX102 mass spectrometer. In the EI mode accurate mass was determined using a VG7070F mass spectrometer. All adenosine derivatives were judged to be homogeneous using thin layer chromatography (silica, 0.25 mm, glass-backed, Alltech Assoc., Deerfield, Ill.; analytical TLC plates and silica gel (230–400 mesh), VRW, Bridgeport, N.J.) following final purification.

Example 1

This example describes the synthesis of $N^6$-benzyladenosine-$N^1$-oxide.

$N^6$-Benzyladenosine (25 mg, 70 $\mu$mol) and m-chloroperbenzoic acid (38 mg, 220 $\mu$mol) were dissolved in 1 ml acetic acid. The resulting solution was stirred at room temperature for 2 days. The solvent was evaporated under a stream of nitrogen, and the residue was dissolved in a minimum of methanol and chromatographed on a silica plate (250$\mu$) using acetonitrile:water, 4:1 (v/v). The UV absorbing band at $R_f$=0.53 was extracted with methanol to provide 7.3 mg (28% yield) of $N^6$-benzyladenosine-$N^1$-oxide. Mass and $^1$H-NMR spectra were consistent with the assigned structure.

Example 2

This example describes the synthesis of adenosine-5'-N-ethyluronamide-$N^1$-oxide. Adenosine-5'-N-ethyluronamide-$N^1$-oxide was synthesized by a method similar to that of Example 1. Following recrystallization from hot methanol/ether, pure adenosine-5'-N-ethyluronamide-$N^1$-oxide was obtained in 28% yield. Mass (EI, peaks at 324 (m), 308) and $^1$H-NMR spectra were consistent with the assigned structure.

Example 3

This example describes the synthesis of $N^6$-benzyladenosine-5'-N-ethyluronamide.

To a solution of 5'-N-ethylcarboxamidoadenosine (NECA, 50 mg, 0.162 mmol) in dimethylformamide (DMF, 1 ml) was added benzyl bromide (56 ml, 0.47 mmol). The resulting solution was stirred for two days at 40° C. while protected from moisture. DMF was removed under vacuum resulting in a syrup that crystallized when acetone and ether were added. The solvent was removed by decantation, and the solid was dried and dissolved in methanol (2 ml). $K_2CO_3$ (10 mg) was added and warmed under reflux overnight. The reaction mixture was cooled, filtered, and evaporated. The product was purified by preparative thin layer chromatography (TLC) ($CHCl_3$:MeOH 13:2) in 42% yield. Mp: 170°–173° C. $^1$H NMR (in DMSO-$d_6$): δ1.06 (t, J=7 Hz,3H, $CH_3$), 3.20 (m, 2H, $CH_2$), 4.13 (t, J=4 Hz, 1H, H-3'), 4.30 (s, 1H, H-4'), 4.62 (m, 1H, H-2'), 4.71 (br. s, 2H, $N^6$—$CH_2Ph$), 5.53 (d, J=7 Hz, 1H, OH-2'), 5.73 (d, J=4 Hz, 1H, OH-3'), 5.96 (d, J=8 Hz, 1H, H-1'), 7.30 (m, 5H, Phenyl), 8.25 (s, 1H, H-2), 8.42 (s, 1H, H-8), 8.55 (br. s, 1H, $N^6$H—$CH_2Ph$), 8.86 (t, J=5 Hz, 1H, NH-Et). Mass Spectrum (CI—$NH_3$): m/e 399 ($MH^+$, base).

Example 4

This example describes the synthesis of inosine-5'-N-ethyluronamide (NECI). 2',3'-O-Isopropylideneinosine-5'-uronic acid (20 mg, 62 $\mu$mol) (Olsson et al., *J. Med. Chem.*, 29, 1683–1689 (1986)), 1-[3-(dimethylamino)propyl]-3-ethylcarbodiimide hydrochloride (25 mg, 130 $\mu$mol), and N-hydroxysuccinimide (13 mg, 112 $\mu$mol) were dissolved in a minimum volume of DMF. Ethylamine (70% in water, 7 $\mu$l) was added and, after 1 hour of stirring, was cooled to 0° C. and precipitated with water to yield 14 mg (65% yield). The product (10 mg, 29 $\mu$mol) was heated in 1N HCl for 2 hours at 60° C. After cooling and neutralizing with $NaHCO_3$, the product was purified twice using reverse phase SepPak cartridges, with water as eluant. Lyophilization of the fraction afforded 6.95 mg (78% yield) of an amorphous solid. Mp: 168° C. (d). $^1$H NMR (in DMSO-$d_6$): δ1.03 (t, J=7 Hz,3H, $CH_3$), 3.17 (m, 2H, $CH_2$), 4.15 (br s, 1H, H-3'), 4.30 (s, 1H, H-4'), 4.54 (m, 1H, H-2'),5.61 (br s, 1H, OH), 5.68 (br. s, 1H, OH), 5.96 (d, J=7 Hz, 1H, H-1'), 8.08 (s, 1H, H-2), 8.39 (s, 1H, H-8).

Mass spectrum (CI—$NH_3$): m/e 310 ($MH^+$, base).

Example 5

This example describes the synthesis of $N^6$-(4-nitrobenzyl)adenosine-5'-N-ethyluronamide.

To a solution of NECA (50 mg, 0.162 mmol) in DMF (0.5 ml) was added 4-nitrobenzyl bromide (53 mg, 0.245 mmol), and the solution was stirred for two days at 40° C. DMF was removed under vacuum giving a syrup that crystallized when acetone and ether were added. The solvent was removed using a Pasteur pipette. Methanol (1.0 ml) and concentrated $NH_4OH$ (2.0 ml) were added, and the mixture was warmed in a closed vessel at 90° C. for 45 min. The solvent was evaporated, and the product was purified by preparative TLC (silica gel, ethyl acetate:isopropanol:water, 4:1:2) to yield 7 mg of the pure product ($R_f$ 0.77, 20% yield). Mp: 196° C.

¹H NMR (in DMSO-d₆): δ1.06 (t, J=7 Hz,3H, CH₃), 3.20 (m, 2H, CH₂), 4.13 (br. s, 1H, H-3'), 4.30 (s, 1H, H-4'), 4.60 (m, 1H, H-2'), 4.82 (br. s, 2H, N⁶—CH₂Ph), 5.55 (d, J=6 Hz, 1H, OH-2'), 5.73 (d, J=4 Hz, 1H, OH-3'), 5.97 (d, J=7 Hz, 1H, H-1'), 7.58 (d, 2H, J=9 Hz, arom), 8.17 (d, 2H, J=9 Hz, arom), 8.25 (s, 1H, H-2), 8.46 (s, 1H, H-8), 8.70 (br. s, 1H, N⁶H—CH₂Ph), 8.81 (t, J=5 Hz, 1H, NH-Et).

Mass Spectrum (CI—NH₃): m/e 444 (MH⁺, base).

Example 6

This example describes the synthesis of N⁶-benzyladenosine-5'-N-methyluronamide.

To a solution of adenosine-5'-N-methyluronamide (MECA, 20 mg, 0.068 mmol) in DMF (1 ml) was added benzyl bromide (24 μl, 0.20 mmol), and the solution was stirred for 60 hrs at 40° C. DMF was removed under vacuum giving a syrup that crystallized when acetone and ether were added. The solvent was removed by decantation. Methanol (0.5 ml) and concentrated K₂CO₃ (10 mg) were added, and the mixture was warmed in a closed vessel at 60° C. for 6 hrs. The reaction mixture was cooled, filtered and evaporated. The chromatographically pure product was isolated using C18-silica packed cartridges. Yield:3.4 mg (13% yield).

¹H NMR (in DMSO-d₆): δ2.7 (d, J=4 Hz, 3H, CH₃), 4.13 (t, J=4 Hz, 1H, H-3'), 4.31 (q, J=4.5 and 7, 1H, H-4'), 4.59 (m, 1H, H-2'), 4.71 (br. s, 2H, N⁶—CH₂Ph), 5.96 (d, J=7 Hz, 1H, H-1'), 7.30 (m, 5H, Phenyl), 8.29 (s, 1H, H-2), 8.43 (s, 1H, H-8), 8.56 (br. s, 1H, N⁶H—CH₂Ph), 8.86 (d, J=4 Hz, 1H, NH—Me).

Example 7

This example describes the synthesis of N⁶-benzyladenosine-5'-N-cyclopropyluronamide.

To a solution of adenosine-5'-N-cyclopropyluronamide (20 mg, 0.062 mmol) in anhydrous DMF (1 ml) was added benzyl bromide (22 μl, 0.19 mmol), and the solution was stirred for 60 hrs at 40° C. DMF was removed under vacuum giving a syrup that crystallized when acetone and ether were added. The solvent was removed by decantation. Methanol (0.5 ml) and concentrated NH₄OH (2.0 ml) were added, and the mixture was warmed in a closed vessel at 90° C. for 2 hrs. The mixture was reduced in volume by evaporation and cooled in an ice bath, resulting in precipitation of the chromatographically pure product. The white solid was isolated by filtration, washed with water, and dried to yield 15 mg (59% yield) of product which melted at 178°–180° C.

¹H NMR (in DMSO-d₆): δ0.46 (m 0, 2H, CH₂), 0.69 (m, 2H, CH₂), 2.70 (d, 1H, CH₃), 4.13 (t, J=4 Hz, 1H, H-3'), 4.27 (s, 1H, H-4'), 4.57 (c, 1H, H-2'), 4.71 (br. s, 2H, N⁶—CH₂Ph), 5.53 (d, J=8 Hz, 1H, OH-2'), 5.73 (d, J=4 Hz, 1H, MeOH-3')5.95 (d, J=8 Hz, 1H, H-1'), 7.30 (m, 5H, Phenyl), 8.22 (s, 1H, H-2), 8.42 (s, 1H, H-8), 8.56 (br. s, 1H, N⁶H—CH₂Ph), 8.88 (d, J=4 Hz, 1H, NH—Me).

Example 8

This example describes the synthesis of N⁶-(2-nitrobenzyl)adenosine-5'-N-ethyluronamide.

To a solution of NECA (25 mg, 0.081 mmol) in DMF (0.5 ml) was added 2-nitrobenzyl bromide (53 mg, 0.249 mmol), and the solution was stirred for two days at 40° C. DMF was removed under vacuum giving a syrup that crystallized when acetone and ether were added. The solvent was removed using a Pasteur pipette. Methanol (2.0 ml) and concentrated NH₄OH (2.0 ml) were added, and the mixture was warmed in a closed vessel at 90° C. for 45 min. The solvent was evaporated, and the product was purified by preparative TLC (silica gel, ethyl acetate:isopropanol:water, 4:1:2) to yield 3.5 mg of the pure product (9.7% yield). Mp: 181° C.

¹H NMR (in DMSO-d₄): δ1.05 (t, J=7 Hz,3H, CH₃), 3.30 (m, 2H, CH₂), 4.13 (t, J=5 1 Hz), 4.27 (m, 1H, H-3'), 4.30 (s, 1H, H-4"), 4.58 (m, 1H, H-2'), 4.98 (m, 2H, N⁶—CH₂Ph) ,5.54 (d, J=7, 1H, OH-2'0, 5.73 (d, J=4, 1H, OH-4'), 5.97 (d, J=7, 1H, H-1'), 7.55 (m, 2H, arom), 7.67 (t, 1H, arom), 8.04 (d, 1H, arom), 8.21 (s, 1H, H-2'), 8.47 (s, 1H, H8), 8.62 (m, 1HN⁶H—CH₂Ph), 8.80 (t, J=5, 1H, NH-Et).

Example 9

This example describes the synthesis of N⁶-(3-chlorobenzyl)adenosine-5'-N-ethyluronamide.

To a solution of NECA (50 mg, 0.162 mmol) in DMF (1 ml) was added 3-chlorobenzyl bromide (61 μl, 0.47 mmol), and the solution was stirred in a closed vessel for two days at 40° C. DMF was evaporated under a stream of nitrogen. The residue was treated with acetone (1 ml) and ether (2 ml). The solvent was removed using a Pasteur pipette, and the residue, an amorphous solid, was again extracted with chloroform to remove traces of the benzyl bromide. The dried residue was treated with methanol (2.0 ml) and concentrated NH₄OH (4.0 ml), and the mixture was warmed in a closed tube at 90° C. for 2 h with stirring. The mixture was reduced in volume by evaporation and cooled in an ice bath, resulting in precipitation of the chromatographically pure product. The white solid was isolated by filtration to yield 43 mg (62% yield) of product, which melted at 199°–200° C.

¹H NMR (in DMSO-d₆): δ1.06 (t, J=7 Hz,3H, CH₃), 3.2 (m, 2H, CH₂), 4.13 (t, 1H, H-3'), 4.30 (s, 1H, H-4'), 4.6 (m, 1H, H-2'), 4.71 (br. s, 2H, N⁶—CH₂Ph), 5.53 (d, J=7 Hz, 1H, OH-2'), 5.72 (d, J=4 Hz, 1H, OH-3'), 5.97 (d, J=8 Hz, 1H, H-1'), 7.2–7.4 (m, 4H, Phenyl), 8.26 (s, 1H, H-2), 8.44 (s, 1H, H-8), 8.6 (br. s, 1H, N⁶H—CH₂Ph), 8.82 (t, J=5 Hz, 1H, NH-Et).

Mass Spectrum (CI—NH₃): m/e 433 (MH⁺, base).

Example 10

This example describes the synthesis of N⁶-(4-methoxybenzyl)adenosine-5'-N-ethyluronamide.

To a solution of NECA (50 mg, 0.162 mmol) in DMF (0.5 ml) was added 4-methoxybenzyl chloride (33 μl, 0.24 mmol), and the solution was stirred for three days at 40° C. DMF was removed under vacuum giving a syrup that crystallized when acetone and ether were added. The solvent was removed using a Pasteur pipette. Methanol (1.0 ml) and concentrated NH₄OH (2.0 ml) were added, and the mixture was warmed in a closed vessel at 90° C. for 45 min. The solvent was evaporated, and the product was purified by preparative TLC (silica gel, ethyl acetate: isopropanol:water, 4:1:2) to yield 4.9 mg of the pure product (14% yield).

¹H NMR (in DMSO-d₆): δ1.07 (t, J=7 Hz,3H, CH₃), 3.2 (m, 2H, CH₂), 3.69 (s, OCH₃), 4.12 (d, J=5 Hz, 1H, H-3'), 4.29 (s, 1H, H-4'), 4.59 (c, J=8 Hz, J=5 Hz 1H, H-2'), 4.63 (br. s, 2H, N⁶—CPh), 5.96 (d, J=8 Hz, 1H, H-1'), 6.84 (d, J=9 Hz, 2H, arom), 7.27 (d, J=9 Hz, 2H, arom), 8.25 (s, 1H, H-2), 8.40 (s, 1H, H-8), 8.45 (br. s, 1H, N⁶H—CH₂Ph), 8.85 (t, J=5 Hz, 1H, NH-Et).

Mass Spectrum (Cl—NH₃): m/e 429 (MH⁺, base).

Example 11

This example describes the synthesis of inosine-5'-N-methyluronamide.

2',3'-Isopropylideneinosine 5'-carboxylic acid (50 mg, 0.155 mmol), EDAC (59 mg, 0.31 mmol), and N-hydroxysuccinimide (36 mg, 0.31 mmol) were dissolved in DMF (1 ml). Methylamine was added, and the mixture was stirred for 90 min. Water was then added, and the 6-hydroxypurine-5'-N-methyl-carboxamidoriboside solid residue was separated and dried in vacuo. 6-hydroxypurine-5'-N-methyl-carboxamidoriboside was purified by column chromatography (silica, eluted with chloroform:methanol:25% ammonium hydroxide, 80:20:1) to yield 49.8 mg (96%) of the pure product. The isopropylidene group was removed by adding hydrochloric acid (1N, 1 ml) and heating to 60° C. for 45 min or until complete as judged by TLC. Inosine-5'-N-methyluronamide was purified using reverse phase cartridges.

Example 12

This example describes the synthesis of $N^6$-(3-iodobenzyl)adenosine-5'-N-methyluronamide.

6-Chloropurine-5'-N-methyl-carboxamidoriboside (35 mg, 99 μmol), 3-iodobenzylamine hydrochloride (28 mg, 104 μmol), and triethylamine (41 μl, 0.30 mmol) were dissolved in absolute ethanol (1 ml). The solution was stirred at 75° C. for 16 hours in a sealed vessel. The solvent was evaporated under a stream of nitrogen, and water was added to remove the triethylammonium salt. The supernatant was removed and discarded, and the insoluble residue containing intermediate 3-iodobenzyladenine-5'-N-methylcarboxamidoriboside was used without further purification.

Hydrochloric acid (1N, 1 ml) was added, and the resulting solution was heated to 60° C. for 4 hours. After cooling in an ice bath, sodium bicarbonate solution was added to neutralize. A white solid formed and was filtered, washed with water, and dried to yield 28 mg of $N^6$-(3-iodobenzyl)adenosine-5'-N-methyluronamide (55% yield overall).

Example 13

This example describes the synthesis of $N^6$-(3-aminobenzyl)adenosine-5'-N-methyluronamide.

3-Aminobenzylamine was prepared by catalytic reduction of 3-nitrobenzylamine hydrochloride (5% Pd/C in methanol).

2',3'-Isopropylidene-inosine 5'-carboxylic acid (1.1 g, 3.4 mmol, Olsson et al., *J. Med. Chem.*, 29, 1683–1689 (1986)) was added to a solution of thionyl chloride (0.51 ml, 0.68 mmol) and dimethylformamide (0.26 ml) in anhydrous chloroform (43 ml, dried over $Al_2O_3$). The mixture was heated to reflux with the exclusion of moisture for 6 h. After cooling the solvent was removed in vacuo leaving a syrup, that was dissolved in chloroform (12 ml). The solution was cooled to 0° C. and 2 ml of methylamine dissolved in 20 ml of chloroform was added. After stirring for 15 min at<10° C., the solution was extracted successively with HCl (0.1N, 3×60 ml), sodium bicarbonate (0.5M, 100 ml), and water (2×50 ml). The organic layer was dried ($MgSO_4$) and the solvent evaporated leaving 632 mg of homogeneous ($R_f$= 0.75, chloroform:methanol:ammonium hydroxide, 80:20:1) 2',3'-isopropylidene-6-chloropurine-riboside-5'-methyluronamide (53% yield). NMR DMSO, $d_6$ δ8.80 (s, 1H, purine), 8.73 (s, 1H, purine), 7.48 (s, 1H, C4'), 6.50 (s, 1H, C1'), 5.4–5.5 (m, 2H, C2' and C3'), 2.16 (d, J=4.7 Hz, 3H, $NCH_3$), 1.53 (s, 3H, i-Pr), 1.34 (s, 3H, i-Pr).

2',3'-isopropylidine-6-chloropurine-riboside-5'-methyluronamide (100 mg, 0.28 mmol) was dissolved in ethanol (15 ml) and treated with 3-aminobenzylamine (47 mg, 0.30 mmol) and triethylamine (117 μl, 0.84 mmol). The solution was heated at 80° C. for 12 h in an oil bath. The solvent was evaporated, leaving a solid residue. The residue was treated with 1N HCl (1.0 ml), and the mixture heated at 80° C. for 45 min. Sodium bicarbonate solution was added until pH 7, and the mixture was extracted 3×with ethyl acetate. The solvent was removed under vacuum, and the residue was recrystallized from methanol/water to provide 56 mg of the pure product (50% yield).

Example 14

This example describes the synthesis of $N^6$-(3-trifluoromethylbenzyl)adenosine-5'-N-methyluronamide.

The compound was prepared as described above for Example 12 using 3-trifluorobenzylamine, except that due to aqueous insolubility, the hydrolysis on the isopropylidene protecting group was carried out in a 1:1 mixture of 1N HCl and methanol.

Example 15

This example describes the synthesis of $N^6$-(4-sulfobenzyl)adenosine-5'-N-methyluronamide triethylammonium salt.

p-Sulfobenzylamine was synthesized in 40% yield from benzylamine and fuming sulfuric acid, by an adaptation of the method described in Jacobson et al., *J. Med. Chem.*, 35, 4143–4149 (1992), and was recrystallized from a solution in ammonium hydroxide, upon neutralization with hydrochloric acid. NMR DMSO, $d_6$ δ8.10 (br.s, 3H, $NH_3^+$), 7.62 (d, J=8.1 Hz, 2H, o- to sulfo), 7.38 (d, J=8.1 Hz, 2H, m- to sulfo), 4.02 (s, 2H, $CH_2$).

2',3'-Isopropylidene-6-chloropurine-riboside-5'-methyluronamide (30 mg, 85 μmol, prepared as described in Example 13), p-sulfobenzylamine (17 mg, 90 μmol), and triethylamine (34 μl, 0.27 mmol) were combined in absolute ethanol (1 ml) and heated to 90° C. for 3 days. The mixture was filtered, and the filtrate was reduced in volume by evaporation leaving a viscous syrup. The isopropylidene-protected intermediate was purified (23.5 mg, recovered) on a TLC plate run in chloroform:methanol:acetic acid (85:10:5). Hydrochloric acid (1 ml, 1N) was added, and the solution was warmed at 60° C. for 40 min. After cooling and evaporation of the solvent, methanol and ethyl acetate were added. The resulting precipitate was separated and dried to provide 14.3 mg (29% yield) of $N^6$-(4-sulfobenzyl)adenosine-5'-N-methyluronamide triethylammonium salt.

Example 16

This example describes the synthesis of $N^6$-(3-fluorobenzyl)adenosine-5'-N-ethyluronamide.

6-Chloropurine-5'-N-ethyl-carboxamidoriboside (30 mg, 81 μmol) and 3-fluorobenzylamine (10.8 mg, 86 μmol) were dissolved in absolute ethanol (1 ml). Triethylamine (17 μl, 0.12 mmol) was added and the solution was warmed at 80° C. for 16 h in a sealed vessel. No starting material ($R_f$ 0.41, silica TLC plates, chloroform:methanol, 95:5) remained in the mixture. The solvent was evaporated under a stream of nitrogen, and water was added to remove the triethylammonium salt. The supernatant was removed and discarded, and the insoluble residue containing intermediate 3-fluorobenzyladenine-5'-N-ethylcarboxamidoriboside was used without further purification.

The isopropylidene group was removed by addition of hydrochloric acid as described in Example 11. The intermediate 3-fluorobenzyladenine-5'-N-ethylcarboxamidoriboside and product displayed $R_f$ values of 0.51 and 0.10, respectively (silica, chloroform:methanol, 95:5). After cooling, sodium bicarbonate solution was added to neutralize. A white solid precipitated and was filtered, washed with water, and dried to yield 23 mg of $N^6$-(3-fluorobenzyl)adenosine-5'-N-ethyluronamide (68% yield overall).

Example 17

This example describes the synthesis of 2',3'-isopropylidene-adenosine-5'-carboxylic acid.

2',3'-Isopropylidene-adenosine (0.5 g, 1.6 mmol, Aldrich Chemical Co., St. Louis Mo.) was dissolved in glacial acetic acid (11 ml) and chromium trioxide (0.222 g, 2.22 mmol) was added. A brown suspension was formed. The color changed gradually to dark green. The suspension was stirred at room temperature for 4 days. The dark solid formed was filtered, washed with water and crystallized from MeOH to afford a white solid (0.28 g, 54%). mp 257° C. $^1$H NMR (DMSO-$d_6$) δ8.24 (s, 1H, H-8), 8.08 (s, 1H, H-2), 7.28 (br.s, 2H, NH$_2$), 6.33 (s, 1H, H-1'), 5.50 (ABq, 2H, H-2', H-3'), 4.68 (s, 1H, H-4'), 1.52,1.35 (s, 3H, Me) ppm. High Res. MS calc'd. for $C_{13}H_{15}N_5O_5$: 321.1058; Found: 321.1073. IR (KBr) v: 3000, 1706 cm$^{-1}$.

Example 18

This example describes the synthesis of 2',3'-Isopropylidene-adenosine-5'-methyl-carboxylate.

An excess of diazomethane in ether (0.75M) was added dropwise over 0.5 hr to a suspension of 2',3'-isopropylidene adenosine 5'-carboxylic acid (0.22 g, 0.68 mmol) in dioxane: MeOH (1:1, 50 ml), until a clear yellowish solution was obtained. The reaction mixture was stirred at room temperature for 1.5 h. Nitrogen was bubbled through the solution until the yellow color disappeared. The solvent was removed and the product was dried under high vacuum to produce a white solid (0.211 g, 92%). mp 221°–222° C. $^1$H NMR (DMSO $d_6$) δ: 8.25 (s, 1H, H-8), 8.05 (s, 1H, H-2), 7.32 (s, 2H, NH2), 6.38 (s, 1H, H-1'), 5.61 (d, J=6 Hz, 1H, H-2'), 5.43 (d, J=6 Hz, 1H, H-3'), 4.85 (s, 1H, H-4'), 3.29 (s, 3H, CO$_2$Me), 1.51, 1.34 (s, 3H, Me) ppm. High Res. MS calc'd. for C14H17N5O5: 335.1238; Found: 335.1230.

Example 19

This example describes the synthesis of 1,3-di-n-butyl-6-aminouracil.

N,N-Di-n-butylurea (34.45 g, 0.2 mmol), cyanoacetic acid (19.56 g, 0.23 mol), and acetic anhydride (81.66 ml, 0.8 mol) were heated at 80° C. for 2 h under nitrogen and solvent was removed by rotary evaporation to yield N-(2-cyanoacetyl)-N,N'-dibutylurea. The N-(2-cyanoacetyl)-N, N'-dibutylurea was dissolved in methanol (100 ml) and 4N NaOH (100 ml) was added. The reaction mixture was cooled for 30 min with stirring and the solid was filtered and dried to yield 1,3-di-n-butyl-6-aminouracil (47.04 g, 99.5%) as a colorless solid, m.p. 90.1°–92.4° C.; $^1$H NMR (DMSO-$d_6$) δ1.72–1.93 (m, 6H, 2×CH$_3$, 1.18–1.33 (m, 4H, 2×CH$_2$), 1.39–1.52 (M, 4H, 2×CH$_2$), 3.70 (t, 2H, N—CH$_2$), 3.76 (t, 2H, N—CH$_2$), 4.64 (s, 1H, H-4), 6.77 (br s, exchangeable with D$_2$O, 2H, NH$_2$).

Example 20

This example describes the synthesis of 6-amino-1,3-di-n-butyl-5-nitroso-uracil.

To a mixture of 1,3-di-n-butyl-6-amino-uracil g, 112.8 mmol), glacial acetic acid (10 ml), and 6N HCl (18.8 ml) in water (500 ml) was added dropwise a solution of sodium nitrite (7.78, g, 112.8 mmol) in water (30 ml) on ice bath. The reaction mixture was stirred for 30 min. The violet solid was collected by filtration and washed with water (2×20 ml), dried for 2 days at 60° C. in a vacuum oven to yield 6-amino-1,3-di-n-butyl-5-nitroso-uracil (24.99 g, 82.6%), m.p. 199°–205° C.; $^1$H NMR (CDCl$_3$) δ0.97–1.01 (m, 6H, 2×CH$_3$), 1.36–1.49 (m, 4H, 2×CH$_2$), 1.62–1.74 (m, 4H, 2×CH$_2$), 3.94 (t, J=7.8 Hz, 2H, N—CH$_2$), 4.08 (t, J=7.5 Hz, 2H, N—CH$_2$), 6.46 (br s, 2H, NH$_2$). Anal. Calc'd for $C_{12}H_{20}N_4O_3$: C, 53.72; H, 7.51; N, 20.88; Found: C, 54.37; H, 7.67; N, 20.65.

Example 21

This example describes the synthesis of 1,3-di-n-butyl-xanthine.

A mixture of 6-amino-1,3-di-n-butyl-5-nitroso-uracil (3.1 g, 11.6 mmol) and 5% Pd-C in dry DMF (30 ml) was hydrogenated at 50 psi until it became a colorless solution (about 2 h). The catalyst was filtered off through Celite pad and the filtrate was mixed with 88% formic acid (15 ml) and 1-(3-dimethylaminopropyl)-3-ethyl-carbodiimide hydrochloride (1.1 g, 5.74 mmol) at 0° C. under nitrogen. The violet solution was stirred at room temperature for 3 h. DMF and formic acid were removed by rotary evaporation and the solid residue was mixed with 2N sodium hydroxide (50 ml, 100 mmol). The reaction mixture was heated at reflux for 1 h. The yellow solution was cooled and neutralized with 6N hydrochloric acid to pH 3. The solid was collected by filtration, washed with water, and dried to yield 1,3-di-n-butyl-xanthine (2.3 g, 75%), m.p. 165.5°–169° C.; $^1$H NMR (DMSO-$d_6$) δ1.41–1.47 (m, 6H, 2×CH$_3$), 1.61–1.68 (m, 4H, 2×CH$_2$), 1.74–1.79 (m, 2H, CH$_2$), 1.82–1.85 (m, 2H, CH$_2$), 3.84 (t, 2H, N—CH$_2$), 3.98 (t, 2H, N—CH$_2$), 8.10 (s, 1H, H-8), 13.7 (br s, 1H, NH).

Example 22

This example describes the synthesis of 1,3-di-n-butyl-xanthine-7-β-D-ribofuranoside.

A mixture of 1,3-di-n-butyl-xanthine (3 g, 11.35 mmol), ammonium sulfate (5 mg), and HMDS (20 ml) was stirred in reflux for 1 h under nitrogen. HMDS was removed by rotary evaporation in vacuo with exclusion of moisture. The brown syrup was dissolved in dry acetonitrile (70 ml). 1-O-Acetyl-2,3,5-tri-O-benzoyl-β-D-ribofuranoside (5.73 g, 11.36 mmol), potassium nonaflate (15.35 g, 45.39 mmol), and trichlorosilane (4.29 ml, 42.5 mmol) were added to the solution and the reaction mixture was refluxed for 3 h under nitrogen.

Aqueous saturated sodium bicarbonate (30 ml) and chloroform (30 ml) were added. After stirring for 30 min, two layers were separated and the water layer was extracted with chloroform (300 ml). The combined organic layer was washed with brine, dried over anhydrous MgSO$_4$, filtered, and concentrated to dryness. Purification on silica gel column chromatography (CHCl$_3$—MeOH, 250:1→100:1) yielded 1,3-dibutyl-7-(2,3,5-tribenzoyl-1-β-D-ribofuranosyl)xanthine as pale yellow foam. $^1$H NMR (CDCl$_3$) δ0.92–0.98 (m, 6H, 2×CH$_3$), 1.71–1.44 (m, 4H, 2×CH$_2$), 1.53–1.61 (m, 2H, CH$_2$), 1.68–1.76 (m, 2H, CH$_2$, 3.98 (t, J=7.6 Hz, 2H, N—CH$_2$), 4.09 (t, J=7.5 Hz, 2H, N—CH$_2$), 4.71–4.82 (m, 2H), 4.87 (dd, J=11.5 and 2.7 Hz, 1H), 5.98–6.05 (m, 2H, H-5'), 6.68 (d, J=4.9 Hz, 1H, H-1'), 7.34–7.62, 7.91–8.11 (m, 16H, Ar and H-8).

A mixture of 1,3-dibutyl-7-(2,3,5-tribenzoyl-1-β-D-ribofuranosyl)xanthine and NH$_3$/MeOH (80 ml) was stirred at room temperature for 2.5 days. The volatiles were removed and the residue was purified on silica gel column chromatography (CHCl$_3$—MeOH, 20:1) to yield 1,3-di-n-butylxanthine-7-β-ribofuranoside (3.5 g, 78.1%) as a white solid, m.p. 139°–140° C.; $^1$H NMR (DMSO-d$_6$) δ0.89 (pseudo t, J=7.4 and 7.3 Hz, 6H, 2×CH$_3$), 1.23–1.35 (m, 4H, 2×CH$_2$), 1.47–1.57 (m, 2H, CH$_2$), 1.59–1.69 (m, 2H, CH$_2$), 3.54 (dd, J=12.1 and 3.7 Hz, 1H), 3.68 (dd, J=12.1 and 3.7 Hz, 1H), 3.84–3.94 (m, 2H), 3.99 (t, J=7.2 Hz, 2H), 4.08 (t, J=4.9 Hz, 1H), 4.33 (t, J=4.8 Hz, 1H), 5.05 (t, exchangeable with D$_2$O, 1H, 5'-OH), 5.15 (d, exchangeable with D$_2$O, 1H, OH), 5.50 (d, exchangeable with D$_2$O, 1H, OH), 6.10 (d, J=4.8 Hz, 1H, H-1'), 8.45 (s, 1H, H-8). Anal. Calc'd for C$_{18}$H$_{28}$N$_4$O$_6$: C, 54.53; H, 7.12; N, 14.13; Found: C, 54.71; H, 7.10; N, 14.10.

Example 23

This example describes the synthesis of 1,3-di-n-butylxanthine-7-β-D-2,3-O-isopropylidene-ribofuranoside.

A mixture of 1,3-di-n-butylxanthine-7-β-D-ribofuranoside (1.56 g, 3.94 mmol), p-toluenesulfonic acid (1.3 g, 1.58 mmol), and dry acetone (25 ml) was stirred at room temperature for 7 h and kept in refrigerator for 2 days. After stirring for 1 h at room temperature, the reaction mixture was neutralized by triethylamine and the solvent was removed by rotary evaporation. The residue was purified by silica gel column chromatography (CHCl$_3$—MeOH, 100:0→50:1) to yield 1,3-di-n-butylxanthine-7-β-D-2,3-O-isopropylidene-ribofuranoside (1.7 g, 98.9%) as a thick syrup. $^1$H NMR (DMSO-d$_6$) δ0.89 (t, J=7.3 Hz, 6H, 2×CH$_3$), 1.21–1.35 (m, 7H, 2×CH$_2$ and isopropylidene), 1.47–1.56 (m, 5H, CH$_2$ and isopropylidene), 1.59–1.69 (m, 2H, CH$_2$), 3.49–3.57 (m, 2H, H-5'), 3.86 (pseudo t, J=7.6 and 7.2 Hz, 2H, N—CH$_2$), 3.99 (pseudo t, J=7.3 and 7.2 Hz, 2H, N—CH$_2$), 4.17 (dd, J=8.1 and 4.9 Hz, 1H), 4.88 (dd, J=6.4 and 3.1 Hz, 1H), 5.07 (t, J=5.2 Hz, exchangeable with D$_2$O, 1H, 5'-OH), 5.15 (dd, J=6.4 and 3.5 Hz, 1H), 6.29 (d, J=3.0 Hz, 1H, H-1'), 8.40 (s, 1H, H-8). Anal. Calc'd for C$_{21}$H$_{32}$N$_4$O$_6$: C, 57.78; H, 7.39; N, 12.84; Found: C, 57.68; H, 7.43; N, 12.77.

Example 24

This example describes the synthesis of methyl-1,3-di-n-butylxanthine-7-β-D-2,3-O-isopropylidene-ribofuronate.

A solution of sodium periodate (1.61 g, 7.53 mmol) in water (15 ml) was added to a solution of 1,3-di-n-butylxanthine-7-β-D-2,3-O-isopropylidene-ribofuranoside (0.8 g, 1.83 mmol) in CHCl$_3$:CH$_3$CN(1:1,20 ml) at room temperature and followed by ruthenium (III) chloride (3.8 mg, 0.018 mmol). The reaction mixture was stirred vigorously for 6 days at room temperature. After the two layers were separated, the aqueous layer was extracted with chloroform (2×50 ml) and the combined organic layer was washed with brine, dried over anhydrous MgSO$_4$, filtered, and concentrated to dryness to yield crude 1,3-di-n-butylxanthine-7-β-D-2,3-O-isopropylidene-ribofuronic acid (0.74 g) as a foam.

To a solution of acid (dried in vacuo for 3 h) in MeOH (15 ml) were added DMAP (0.02 g, 016 mmol) and then EDAC (0.79 g, 4.13 mmol) and the reaction mixture was stirred for 17 h at room temperature. After removal of solvent, the residue was dissolved in ethyl acetate (70 ml) and washed with water (2×30 ml), and brine (40 ml), dried over anhydrous MgSO$_4$, filtered, and concentrated to dryness. The residue was purified by silica gel column chromatography (hexanes-ethyl acetate, 1:1) to yield methyl-1,3-di-n-butylxanthine-7-β-D-2,3-O-isopropylidene-ribofuronate (0.36 g, 47.2%) as a colorless solid and 1,3-di-n-butylxanthine-7-β-D-2,3-O-isopropylidene-ribofuranoside (0.24 g) was recovered, m.p. 72°–73° C.; $^1$H NMR (CDCl$_3$) δ0.92–0.99 (m, 6H, 2×CH$_3$), 1.32–1.47 (m, 7H, 2×CH$_2$ and isopropylidene), 1.55–1.69 (m, 5H, CH$_2$ and isopropylidene), 1.71–1.79 (m, 2H, CH$_2$), 3.77 (s, 3H, —OCH$_3$), 3.95 (t, J=7.8 Hz, 2H, N—CH$_2$), 4.10 (pseudo t, J=7.6 and 7.3 Hz, 2H, N—CH$_2$), 4.80 (s, 1H), 5.17 (d, J=6.2 Hz, 1H), 5.46 (d, J=6.2 Hz, 1H), 6.26 (s, 1H, H-1'), 7.88 (x, 1H, H-8). Anal. Calc'd for C$_{22}$H$_{32}$N$_4$O$_7$: C, 56.89; H, 6.94; N, 12.06; Found: C, 57.17; H, 7.07; N, 11.89.

Example 25

This example describes the synthesis of methyl-1,3-di-n-butylxanthine-7-β-D-ribofuronate.

A solution of methyl-1,3-di-n-butylxanthine-7-β-D-2,3-O-isopropylidene-ribofuronate (30 mg. 0.065 mmol) in 88% formic acid (3 ml) was stirred for 3 h at room temperature and the solvent was removed by rotary evaporation. The residue was purified by preparative TLC (CHCl$_3$—MeOH, 10:1) to yield methyl 1,3-di-n-butylxanthine-7-β-D-ribofuronate (14.8 mg, 57%) as a colorless solid, m.p. 178°–179° C.; $^1$H NMR (DMSO-d$_6$) δ0.90 and 0.91 (2×t, J=7.5 Hz, 2×3H, 2×CH$_3$), 1.23–1.35 (m, 4H, 2×CH$_2$), 1.47–1.57 (m, 2H, CH$_2$), 1.60–1.70 (m, 2H, CH$_2$), 3.72 (s, 3H, —OCH$_3$), 3.87 (t, J=7.3 Hz, 2H, N—CH$_2$), 4.00 (t, J=7.2 Hz, 2H, N—CH$_2$), 4.29 (m, 1H), 4.49 (m, 2H), 5.73 (d, J=6.1 Hz, exchangeable with D$_2$O, 1H, OH), 5.81 (d, J=4.7 Hz, exchangeable with D$_2$O, 1H, OH), 6.29 (d, J=5.4 Hz, 1H, H-1'), 8.46 (s, 1H, H-8). Anal. Calc'd for C$_{19}$H$_{28}$N$_4$O$_7$: C, 53.77; H, 6.65; N, 13.20; Found: C, 53.90; H, 6.62; N, 12.89.

Example 26

This example describes the synthesis of N-methyl 1,3-di-n-butylxanthine-7-β-D-ribofuronamide.

To a solution of methyl-1,3-di-n-butyl-xanthine-7-β-D-2, 3-O-isopropylidene-ribofuronate (50 mg, 0.11 mmol) in MeOH (10 ml) was bubbled methylamine for 5 min at −78° C. (⅓ increase in volume). The reaction mixture was heated for 17 h at 85° C. in a sealed tube. After evaporation of the solvent, the slightly yellow residue was purified by preparative TLC (CHCl$_3$—MeOH, 20:1) to yield N-methyl 1,3-di-n-butylxanthine-7-β-D-2,3-isopropylidene-ribofuronamide (23.1 mg, 46.3%) as a foam.

$^1$H NMR (CDCl$_3$) δ0.96 and 0.97 (2×t, J=7.3 Hz, 2×3H, 2×CH$_3$, 1.34–1.44 (m. 7H, 2×CH$_2$ and isopropylidene), 1.51–1.69 (m, 5H, CH$_2$ and isopropylidene), 1.72–1.79 (m, 2H, CH$_2$), 2.79 (d, J=4.9 Hz, 3H, —NH—CH$_3$), 4.01 (t, J=7.5 Hz, 2H, N—CH$_2$), 4.12 (pseudo t, J=7.6 and 7.3 Hz, 2H, N—CH$_2$), 4.60 (d, J=3.0 Hz, 1H), 5.14 (dd, J=6.9 and 4.0 Hz, 1H), 5.21 (dd, J=6.9 and 3.1 Hz, 1H), 5.91 (d, J=4.0 Hz, 1H, H-1'), 6.92 (m, 1H, NH), 7.72 (s, 1H, H-8).

A mixture of isopropylidene compound (20 mg, 0.043 mmol) and 88% formic acid (3 ml) was reacted for 6 h at room temperature. After the reaction mixture was concentrated to dryness, the residue was coevaporated with toluene (2×5 ml) and triturated with ether to yield N-methyl 1,3-di-n-butylxanthine-7-β-D-ribofuronamide (12.7 mg, 69.5%) as a colorless solid, m.p. 180°–181° C.; $^1$H NMR (DMSO-d$_6$) δ0.88–0.92 (m, 6H, 2×CH$_3$), 1.26–1.35 (m, 4H, 2×CH$_2$), 1.48–1.58 (m, 2H, CH$_2$), 1.61–1.70 (m, 2H, CH$_2$), 2.64 (d, J=4.3 Hz, 3H, NHCH$_3$), 3.88 (t, J=7.4 Hz, 2H, N—CH$_2$), 4.01 (pseudo t, J=7.3 and 7.1 Hz, 2H, N—CH$_2$), 4.16–4.19 (m, 1H), 4.30 (d, J=3.6 Hz, 1H), 4.44–4.47 (m, 1H), 5.60

(pseudo t, J=6.5 and 5.5 Hz, exchangeable with $D_2O$, 2H, 2×OH), 6.19 (d, J=5.4 Hz, 1H, H-1'), 8.11 (q, J=4.3 Hz, exchangeable with $D_2O$, 1H, NH), 8.65 (s, 1H, H-8).

Example 27

This example describes the synthesis of 1,3-di-n-butylxanthine-7-β-D-ribofuronamide.

A mixture of methyl-1,3-di-n-butylxanthine-7-β-D-2,3-O-isopropylidene-ribofuronate (87 mg, 0.19 mmol) and methanolic ammonia (10 ml, saturated at 0° C.) was stirred at 85° C. for 18 h in a sealed bottle. After cooling, the volatiles were removed by rotary evaporation and the residue was purified by preparative TLC ($CHCl_3$—MeOH, 20:1) to yield 1,3-di-n-butyl-xanthine-7-β-D-2,3-isopropylidene-ribofuronamide (67.5 mg, 80.2%) as a syrup. $^1H$ NMR ($CDCl_3$) δ0.93–0.99 (m, 6H, 2×$CH_3$), 1.32–1.47 (m, 7H, 2×$CH_2$ and isopropylidene), 1.55–1.66 (m, 5H, $CH_2$ and isopropylidene), 1.69–1.79 (m, 2H, $CH_2$), 4.00 (pseudo t, J=7.8 and 7.3 Hz, 2H, N—$CH_2$), 4.12 (pseudo t, J=7.5 and 7.3 Hz, 2H, N—$CH_2$), 4.59 (d, J=3.6 Hz, 1H), 5.15 (dd, J=7.1 and 3.9 Hz, 1H), 5.28 (dd, J=7.1 and 3.6 Hz, 1H), 5.35 and 6.86 (2×br s, 2×1H, $NH_2'$), 5.93 (d, J=3.9 Hz, 1H, H-1'), 7.74 (s, 1H, H-8).

A similar deisopropylidenation procedure for N-methyl-1,3-di-n-butylxanthine-7-β-D-ribofuronamide with 56 mg of protected compound followed by crystallization with ether-MeOH yielded 1,3-di-n-butylxanthine-7-β-D-ribofuronamide (20 mg, 40%) as a slightly yellow solid, m.p. 158, 4° C.; $^1H$ NMR (DMSO-$d_6$) δ0.88–0.92 (m, 6H, 2×$CH_3$), 1.23–1.37 (m, 4H, 2×$CH_2$), 1.47–1.57 (m, 2H, $CH_2$), 1.60–1.70 (m, 2H, $CH_2$), 3.87 (pseudo t, J=7.5 and 7.2 Hz, 2H, N—$CH_2$), 4.00 (pseudo t, J=7.3 and 7.2 Hz, 2H, N—$CH_2$), 4,14–4.15 (m, 1H, H-3'), 4.29 (d, J=3.7 Hz, 1H, H-4'), 4.40–4.43 (m, 1H, H-2'), 5.58 (d, J=5.0 Hz, exchangeable with $D_2O$, 1H, OH), 5.62 (d, J=6.1 Hz, exchangeable with $D_2O$, 1H, OH), 6.19 (d, J=5.8 Hz, 1H, H-1'), 7.43 and 7.62 (2×br s, exchangeable with $D_2O$, 2×1H, $NH_2$), 8.67 (s, 1H, H-8).

Example 28

This example describes the synthesis of N-ethyl-1,3-di-n-butyl-xanthine-7-β-D-ribofuronamide.

A mixture of methyl-1,3-di-n-butylxanthine-7-β-D-2,3-O-isopropylidene-ribofuronate (70 mg, 0.15 mmol) and 25% ethylamine/MeOH (10 ml, dissolved at −78° C.) was heated for 18 h at 85° C. in a sealed tube. After evaporation of the solvent, the slightly yellow residue was purified by preparative TLC ($CHCl_3$—MeOH, 20:1) to yield N-ethyl-1,3-di-n-butyl-xanthine-7-β-D-2,3-isopropylidene-ribofuronamide (55.7 mg, 77.4%) as a syrup. $^1H$ NMR ($CDCl_3$) δ0.93–0.99 (m, 6H, 2×$CH_3$), 1.11 (t, J=7.3 Hz, 3H, —$NHCH_2CH_3$), 1.33–1.41 (m, 7H, 2×$CH_2$ and isopropylidene), 1.58–1.70 (m, 5H, $CH_2$ and isopropylidene), 1.72–1.77 (m, 2H, $CH_2$), 3.24–3.32 (m, 2H, —$NHCH_2CH_3$), 4.00 (pseudo t, J=7.9 and 7.8 Hz, 2H, N—$CH_2$), 4.12 (pseudo t, J=7.5 and 7.3 Hz, 2H, N—$CH_2$), 4.58 (d, J=3.5 Hz, 1H), 5.13 (dd, J=6.7 and 3.8 Hz, 1H), 5.18 (dd, J=6.7 and 3.1 Hz, 1H), 5.91 (d, J=4.2 Hz, 1H, H-1'), 6.96 (m, 1H, NH), 7.73 (s, 1H, H-8).

A similar deisopropylidenation procedure for N-methyl 1,3-di-n-butylxanthine-7-β-D-ribofuronamide with 55 mg of protected compounds followed by crystallization with ether-MeOH yielded N,N-dimethyl-1,3-di-n-butylxanthine-7-β-D-ribofuronamide (25.1 mg, 73.8%) as a colorless solid, m.p. 189.4°–189.8° C.; $^1H$ NMR (DMSO-$d_6$) δ0.88–0.93 (m, 6H, 2×$CH_3$), 1.05 (t, J=7.4 Hz, 3H, $NHCH_2CH_3$), 1.24–1.35 (m, 4H, 2×$CH_2$), 1.48–1.58 (m, 2H, $CH_2$), 1.61–1.71 (m, 2H, $CH_2$), 3.09–3.19 (m, 2H, $NHCH_2CH_3$), 3.88 (pseudo t, J=7.5 and 7.2 Hz, 2H, N—$CH_2$), 4.01 (t, J=7.2 Hz, 2H, N—$CH_2$), 4.14–4.19 (m, 1H), 4.29 (d, J=3.5 Hz, 1H), 4.43–4.48 (m, 1H), 5.57 and 5.59 (2×d, J=6.4 and 5.5 Hz, exchangeable with $D_2O$, 2H, 2×OH), 6.17 (d, J=5.5 Hz, 1H, H-1') 8.18 (t, J=5.4 Hz, exchangeable with $D_2O$, 1H, NH), 8.64 (s, 1H, H-8).

Example 29

This example describes the synthesis of N,N-dimethyl-1,3-di-n-butylxanthine-7-β-D-ribofuronamide.

A solution of methyl-1,3-di-n-butyl-xanthine-7-β-D-2,3-O-isopropylidene-ribofuronate. (77 mg, 0.166 mmol) and 25% dimethylamine/MeOH (10 ml, dissolved at −78° C.) was heated for 15 h at 75° C. in a sealed tube. After evaporation of the volatiles, the residue was purified by preparative TLC ($CHCl_3$—MeOH, 20:1) to yield, N,N-dimethyl-1,3-di-n-butylxanthine-7-β-D-2,3-isopropylidene-ribofuronamide (50 mg, 63.2%) as a thick syrup. $^1H$ NMR ($CDCl_3$) δ0.92–0.98 (m, 6H, 2×$CH_3$), 1.33–1.46 (m, 7H, 2×$CH_2$ and isopropylidene), 1.58–1.68 (m, 5H, $CH_2$ and isopropylidene), 1.71–1.78 (m, 2H, $CH_2$), 2.93 and 3.11 [2×s, 2×3H, —N($CH_3$)$_2$], 4.01 (t, J=7.8 Hz, 2H, N—$CH_2$), 4.09 (t, J=7.6 Hz, 2H, N—$CH_2$), 5.07 (s, 1H), 5.15 (d, J=6.3 Hz, 1H), 5.33 (m, 1H), 6.69 (s, 1H, H-1'), 8.01 (s, 1H, H-8).

A similar deisopropylidenation procedure for N-methyl 1,3-di-n-butyl-xanthine-7-β-D-ribofuronamide with 40 mg of protected compound followed by purification on preparative TLC ($CHCl_3$—MeOH, 10:1) yielded N,N-dimethyl-1,3-di-n-butyl-xanthine-7-β-D-ribofuronamide (30 mg, 82%) as a colorless solid, m.p. 154.4°–154.9° C.; $^1H$ NMR (DMSO-$d_6$) δ0.88–0.92 (m, 6H, 2×$CH_3$), 1.24–1.37 (m, 4H, 2×$CH_2$), 1.48–1.57 (m, 2H, $CH_2$), 1.60–1.70 (m, 2H, $CH_2$), 2.89 and 3.05 [2×s, 2×3H, N($CH_3$)$_2$], 3.87 (pseudo t, J=7.5 and 7.1 Hz, 2H, N—$CH_2$), 4.00 (pseudo t, J=7.2 and 6.9 Hz, 2H, N—$CH_2$), 4.22 (dd, J=8.7 and 4.2 Hz, 1H), 4.29–4.34 (m, 1H), 4.90 (d, J=3.9 Hz, 1H), 5.65 and 5.69 (2×d, J=5.5 and 6.0 Hz, exchangeable with $D_2O$, 2H, 2×OH), 6.32 (d, J=4.7 Hz, 1H, H-1'), 8.75 (s, 1H, H-8).

Example 30

This example describes the synthesis of 1-O-methyl 5-(t-butyldiphenylsilyl)-β-D-ribofuranoside.

To a mixture of methyl-β-D-ribofuranoside (460 mg, 2.8 mmol, Sigma, St. Louis, Mo.) and anhydrous methylene chloride (20 ml) were added triethylamine (0.468 ml, 3.36 mmol), t-butyldiphenylchlorosilane (0.9 ml, 3.46 mmol), and DMAP (13.7 mg, 0.112 mmol) successively at room temperature. The reaction mixture was stirred at room temperature for 18 h under nitrogen. It was washed with water (20 ml), saturated ammonium chloride (20 ml), and brine (20 ml), dried over anhydrous $MgSO_4$, filtered, and concentrated to dryness. The residue was separated by silica gel column chromatography ($CHCl_3$—MeOH, 50:1) to yield 1-O-methyl 5-(t-butyldiphenylsilyl)-β-D-ribofuranoside (618 mg, 54.8%) as a thick syrup. $^1H$ NMR (DMSO-$d_6$) δ0.96 (s, 9H, t-Bu), 3.22 (s, 3H, —$OCH_3$), 3.61 (dd, J=11.0 and 5.3 Hz, 1H), 3.74 (d, J=4.4 Hz, 1H), 3.81 (dd, J=11.0 and 2.7 Hz, 1H), 3.90 (m, 1H), 4.00 (m, 1H), 4.68 (s, 1H, H-1'), 4.84 (br s, 1H, exchangeable with $D_2O$, OH), 5.05 (br s, 1H, exchangeable with $D_2O$, OH), 7.45 and 7.67 (m, 10H, $Ph_2$).

Example 31

This example describes the synthesis of 1-O-methyl 5-(t-butyldiphenylsilyl)-2,3-dibenzoyl-β-D-ribofuranoside.

To a solution of 1-O-methyl-5-(t-butyldiphenylsilyl)-β-D-ribofuranoside (579 mg, 1.44 mmol) in methylene chloride-pyridine (4:1, 12.5 ml) was added dropwise benzoyl chloride (0.367 ml, 3.16 mmol) at 0° C. The reaction mixture was stirred for 2.5 h at 0° C. and for 14.5 h at room temperature.

Ice was added to quench the reaction and it was stirred for 1 h. Methylene chloride (100 ml) was added and two phases were separated. The organic layer was washed with water, saturated ammonium chloride, and brine, dried over $MgSO_4$, filtered, and concentrated to dryness to yield crude 1.0-methyl 5-(t-butyldiphenylsilyl)-2,3-dibenzoyl-β-D-ribofuranoside), which was purified by silica gel column chromatography (hexanes-ethyl acetate, 5:1→1:1) to yield 1.0-methyl 5-(t-butyldiphenylsilyl)-2,3-dibenzoyl-β-D-ribofuranoside (869 mg, 99%) as thick syrup. $^1$H NMR ($CDCl_3$) δ1.05 (s, 9H, t-Bu), 3.42 (s, 3H, —$OCH_3$), 3.86 (dd, J=11.1 and 4.8 Hz, 1H, H-5a), 3.92 (dd, J=11.1 and 4.7 Hz, 1H, H-5b), 4.48 (dd, J=10.6 and 4.6 Hz, 1H), 5.15 (s, 1H), 5.63 (d, J=5.0 Hz, 1H), 5.82 (pseudo t, J=5.8 and 5.4 Hz, 1H), 7.29–8.18 (m, 20H, Ar).

Example 32

This example describes the synthesis of 1-O-methyl 2,3-dibenzoyl-β-D-ribofuranoside.

A solution of 1-O-methyl-5-(t-butyldiphenylsilyl)-2,3-dibenzoyl-β-D-ribofuranoside (849 mg, 1.39 mmol) and 1.0M tetrabutylammonium fluoride in THF (1.53 ml, 1.53 mmol) was stirred for 2 h at room temperature. After evaporation of the solvent, the residue was purified by silica gel column chromatography (hexanes-ethyl acetate, 1:1) to yield 1-O-methyl-2,3-dibenzoyl-β-D-ribofuranoside (461 mg, 89%) as thick syrup. $^1$H NMR (DMSO-$d_6$) δ3.38 (s, 3H, —$OCH_3$), 3.62 (m, 2H, H-5), 4.37 (q, J=5.2 Hz, 1H, H-4), 5.02 (pseudo t, J=6.0 and 5.3 Hz, exchangeable with $D_2O$, 1H, 5-OH), 5.18 (s, 1H, H-1), 5.45 (m, 1H, H-2), 5.53 (t, J=5.2 Hz, 1H, H-3), 7.42–7.88 (m, 10H, Ar).

Example 33

This example describes the synthesis of N-methyl-1-O-methyl-2,3-dibenzoyl-β-D-ribofuronamide.

A mixture of 1-O-methyl-2,3-dibenzoyl-β-D-ribofuranoside (374.8 mg, 1.01 mmol), ruthenium (IV) oxide (10 mg), and solium periodate (1161 mg, 5.43 mmol) in $CHCl_3$:$CH_3CN$:$H_2O$ (2:2:3, 14 ml) was stirred vigorously for 2.5 h at room temperature. Chloroform (20 ml) was added and semisolid was removed by filtration. The filtrate was separated and the water layer was extracted with chloroform (2×40 ml). Combined washings and extracts were washed with brine, dried over $MgSO_4$, filtered, and concentrated to dryness. After drying in vacuo overnight 1-O-methyl-2,3-dibenzoyl-β-D-ribofuronic acid (340 mg, 89.5%) was obtained as a thick syrup. $^1$H NMR ($CDCl_3$) δ3.56 (s, 3H, —$OCH_3$), 4.90 (d, J=6.1 Hz, 1H, H-4), 5.25 (s, 1H, H-1), 5.66 (d, J=5.0 Hz, 1H, H-2), 6.00 (pseudo t, J=5.7 and 5.4 Hz, 1H, H-3), 7.32–7.99 (m, 10H, Ar).

EDAC (198 mg, 1.04 mmol) was added to a solution of acid (0.16 g, 0.414 mmol) in MeOH (3 ml) and the reaction mixture was stirred for 3 h at room temperature. After the solvent was removed by rotary evaporation, the residue was dissolved in chloroform (50 ml) and it was washed with water (30 ml) and brine (30 ml), dried over anhydrous $MgSO_4$, filtered, and concentrated to dryness. The residue was purified by preparative TLC (hexanes-ethyl acetate, 1:1) to yield methyl 1-O-methyl-2,3-dibenzoyl-β-D-ribofuronate (120 mg, 72.3%) as colorless solid, m.p. 92.2°–93.7° C.; $^1$H NMR ($CDCl_3$) δ3.52 (s, 3H, 1-$OCH_3$), 3.82 (2, 3H, 5-$OCH_3$), 4.84 (d, J=6.2 Hz, 1H, H-4), 5.21 (s, 1H, H-1), 5.62 (d, J=4.8 Hz, 1H, H-2), 6.01 (pseudo t, J=5.7 and 5.5 Hz, 1H, H-3), 7.32–7.99 (m, 10H, Ar).

A mixture of methyl ester (35 mg, 0.087 mmol) in 2.0M methylamine in THF (3 ml) was heated for 15 h at 50° C. in a sealed tube. The volatiles were removed by evaporation and the residue was reacted with benzoyl chloride (0.15 ml, 1.29 mmol) in methylene chloride-pyridine (2:1, 6 ml) for 3 h at room temperature. Ice was added and the reaction mixture was stirred for 15 min. Methylene chloride (30 ml) was added and the two layers were separated. The aqueous layer was extracted with methylene chloride (20 ml) and the combined organic layer was washed with brine (30 ml), dried over $MgSO_4$, filtered, and concentrated to dryness. The residue was separated by preparative TLC (hexanes-ethyl acetate, 1:1) to yield 1,3-di-n-butyl-xanthine (25 mg, 72%) as a syrup.

$^1$H NMR ($CDCl_3$) δ2.92 (d, J=5.0 Hz, 3H, —$NHCH_3$), 3.58 (s, 3H, 1-$OCH_3$), 4.82 (d, J=5.5 Hz, 1H, H-4), 5.24 (s, 1H, H-1), 5.60 (m, 1H, H-2), 5.87 (t, J=5.1 Hz, 1H, H-3), 6.68 (br m, 1H, —NH), 7.33–7.99 (m, 10H, Ar).

Example 34

This example describes the culture of Chinese hamster ovary (CHO) cells and the preparation of a suspension of CHO cell membranes stably transfected with rat $A_3$ cDNA. These materials were used for the subsequent experimental work set out herein.

CHO cells were transfected with rat $A_3$ cDNA is (Meyerhof et al., supra) using methods well known to those of skill in the art. CHO cells stably expressing the $A_3$ receptor (Zhou et al., supra) were grown in F-12 (Ham's) medium (Gibco BRL, Gaithersburg, Md.) containing 10% fetal bovine serum (FBS, Gibco BRL) and penicillin/streptomycin (100 U/ml and 100 μg/ml, respectively; Gibco BRL) at 37° C. in a 5% $CO_2$ atmosphere. When the transfected CHO cells had reached confluency, they were washed twice with Dulbecco's phosphate buffer solution before dislodging after addition of 3 ml trypsin-EDTA. For the final passage, cells were grown in 150×50 mm tissue culture dishes. Cells were washed twice with 10 ml of ice-cold lysis buffer (10 mM Tris, 5 mM EDTA, pH 7.4, 5° C.). After addition of 5 ml of lysis buffer, cells were mechanically scraped and homogenized in an ice-cold Dounce homogenizer (20 strokes by hand). The suspension was centrifuged at 43,000×g for 10 min. The pellet was resuspended in the minimum volume of ice-cold 50/10/1 buffer (50 mM Tris, 10 mM $MgCl_2$, 1 mM EDTA, pH 8.26, 5° C.) required for the binding assay and homogenized in a Dounce homogenizer. Typically, 6–8 175 $cm^2$ flasks were used for a 48-tube assay. Adenosine deaminase (ADA, Boehringer Mannheim, Indianapolis, Ind.) was added to a final concentration of 3 U/ml, and the suspension was incubated at 37° C. for 15 min. The membrane suspension was subsequently kept on ice until use. When large batches (ca 100 flasks) were processed, homogenization was performed with a Polytron (Brinkman, Luzern, Switzerland) and further work-up was as described above. The preparation was stored at −70° C. and retained its [$^{125}$I]$N^6$-2-(4-aminophenyl)ethyladenosine ([$^{125}$I]APNEA, prepared as described in Stiles et al., J. Biol. Chem., 260, 10806–10811 (1985)) binding properties for at least one month.

Rat cerebral cortical and striatal membranes were prepared (Jacobson et al., J. Med. Chem., 35, 4143–4149 (1992)) and treated with ADA for 30 min at 37° C. prior to storage at −70° C.

Example 35

This example describes a radioligand binding assay used to study the structure activity relationship (SAR) at the $A_3$ receptor.

Binding of [$^{125}$I]APNEA to CHO cells stably transfected with the $A_3$ receptor clone was performed essentially as described in Stiles et al., J. Biol. Chem., 260, 10806–10811 (1985). Assays were performed in 50/10/1 buffer in glass tubes which contained 100 μl of the membrane suspension, 50 μl of [$^{125}$I]APNEA (final concentration 0.5 nM) or

[$^{125}$I]AB-MECA and 50 μl of inhibitor. Inhibitors were routinely dissolved in dimethylsulfoxide (DMSO) and were then diluted with buffer. The final DMSO concentrations never exceeded 1%; this concentration did not influence [$^{125}$I]APNEA binding. Incubations were carried out in duplicate for 1 hour at 37° C., and were terminated by rapid filtration over Whatman GF/B filters, using a Brandell cell harvester (Brandell, Gaithersburg, Md.). Tubes were washed three times with 3 ml of buffer. Radioactivity was determined in a Beckman gamma 5500B γ-counter. Non-specific binding was determined in the presence of 40 μM N$^6$-[(R)-1-methyl-2-phenylethyl]adenosine (R-PIA). $K_i$-values were calculated according to Cheng-Prusoff (Cheng et al., Biochem. Pharmacol., 22, 3099–3108 (1973)), assuming a $K_d$ for [$^{125}$I]APNEA of 17 nM (Zhou et al., supra).

Binding of [$^3$H]PIA (Amersham, Arlington Heights, Ill.) to A$_1$ receptors from rat brain membranes and of [$^3$H]CGS 21680 (DuPont NEN, Boston, Mass.) to A$_2$ receptors from rat striatal membranes was performed as described previously (Jacobson et al. (1992), supra).

Solid samples of the adenosine derivatives were dissolved in DMSO and stored in the dark at −20° C. The stock solutions were diluted with DMSO to a concentration of <0.1 mM prior to addition to the aqueous medium. The final concentration of DMSO in the assay medium was generally 2%.

Binding data for a variety of adenosine derivatives, as well as a number of nucleosides having bases other than adenine, are set forth in the table below. At least six different concentrations spanning three orders of magnitude, adjusted appropriately for the IC$_{50}$ of each compound, were used. IC$_{50}$ values, computer-generated using a nonlinear regression formula of the GraphPAD program (Institute of Scientific Information), were converted to apparent $K_i$ values using $K_D$ values (Jacobson et al. (1992), supra) of 1.0 and 14 nM for [$^3$H]PIA and [$^3$H]CGS 21680 binding, respectively, and the Cheng-Prusoff equation (Cheng et al., Biochem. Pharmacol., 22, 3099–3108 (1973)).

TABLE 1

Affinities of selected compounds at A$_1$, A$_2$ and A$_3$ receptors indicated as either K$_i$ (nM) or percent displacement at a concentration of 100 μM, unless otherwise indicated. Values are means of 3–5 experiments ± SEM. Values without SEM are taken from the literature.

| # | Compound | A$_1$-affinity[a] | A$_2$-affinity[b] | A$_3$-affinity[c] |
|---|---|---|---|---|
| | purine and 5'-modified adenosines | | | |
| 1 | ADAC | 0.85 nM | 210 nM | 281 ± 51 nM |
| 2 | R-PIA | 1.2 nM | 124 nM | 158 ± 52 nM |
| 3 | S-PIA | 49.3 nM | 1,820 nM | 920 ± 311 nM |
| 4 | CPA | 0.59 nM | 462 nM | 240 ± 36 nM |
| 5 | CHA | 1.3 nM | 514 nM | 167 ± 26 nM |
| 6 | N$^6$-phenyladenosine | 4.62 nM | 663 nM | 802 ± 279 nM |
| 7 | N$^6$-benzyladenosine | 120 nM | 285 nM | 120 ± 20 nM |
| 8 | N$^6$-phenethyladenosine | 12.7 nM | 161 nM | 240 ± 58 nM |
| 9 | N$^6$-dimethyladenosine[6] | 10,000 nM | 28,900 ± 8,500 nM | 32,500 ± 5,100 nM |
| 10 | DPMA | 142 nM | 4.4 nM | 3,570 ± 1,700 nM |
| 11 | N$^6$-(2-sulfo)ethyladenosine | 41% | 0% | 32,400 ± 7,600 nM |
| 12 | N$^6$-p-sulfophenyladenosine (SPA) | 74 nM | 8,900 nM | 526 ± 142 nM |
| 13 | N$^6$-3-(p-sulfophenyl)propyl adenosine | 610 nM | 3,840 nM | 844 ± 67 nM |
| 14 | N$^6$-4-(p-sulfophenyl)butyl adenosine | 432 nM | 11,300 nM | 808 ± 116 nM |
| 15 | 1-deaza-2-chloro-N$^6$-CPA (DCCA) | 1.6 nM | 13,200 nM | 770 ± 234 nM |
| 16 | 2-chloroadenosine[10] | 9.3 nM | 63 nM | 1,890 ± 900 nM |
| 17 | 2-chloro-N$^6$-CPA | 0.6 nM | 950 nM | 237 ± 71 nM |
| 18 | 2-phenylaminoadenosine (CV 1808) | 560 nM | 119 nM | 4,390 ± 1,170 nM |
| 19 | CGS 21680 | 2,600 nM | 15 nM | 584 ± 32 nM |
| 20 | 5'-carboxamidoadenosine(CA)[e,6] | 72.6 nM | 120 nM | 1,410 ± 60 nm |
| 21 | NMCA[e] | 83.6 nM | 66.8 nM | 72 ± 16 nM |
| 22 | NECA | 6.3 nM | 10.3 nM | 113 ± 34 nM |
| 23 | 5'-N-cyclopropyl-CA[e,10] | 6.4 nM | 13.4 nM | 1,600 ± 70 nM |
| 24 | N$^6$-benzyl-5'-N-cyclopropyl-CA | 112 ± 13 nM | 55 ± 6 nM | 103 ± 22 nM |
| 25 | 5'-N-aminoethylamino-CA | 0% | 12.5% | 14,700 ± 2,540 nM |
| 26 | 5'-N-boc-aminoethylamino-CA | 0% | 0% | 18,000 ± 4,270 nM |
| 27 | N$^6$-cyclohexylNECA[7] | 0.43 nM | 170 nM | 16.0 ± 5.4 nM |
| 28 | N$^6$-benzylNECA | 87.3 ± 13.9 nM | 95.3 ± 24.6 nM | 6.8 ± 2.5 nM |
| 29 | N$^6$-dimethylNECA[7] | 9,600 nM | 13,500 ± 3,600 nM | 2,260 ± 490 nM |
| 30 | N$^6$-benzyl-N$^6$-methyladenosine[7] | 7,600 ± 1,900 nM | 40,100 ± 6,200 nM | 78.4 ± 4.6% |
| 31 | 8-bromoadenosine[3] | 41.5 ± 3.2% | 22,700 ± 5,100 nM | 31.3 ± 6.0% |
| 32 | 3-deazaadenosine[6] | 21,500 nM | 59,800 ± 4,600 nM | 61,700 ± 34,500 nM |
| 33 | 7-deazaadenosine (tubercidine)[6] | >100,00 nM | 48.3 ± 0.4% | 38.9 ± 17.7% |
| 34 | adenosine-N$^1$-oxide[3] | 246 ± 31 nM | 328 ± 60 nM | 3,090 ± 1,910 nM |
| 35 | NECA-N$^1$-oxide | 154 ± 20 nM | 101 ± 19 nM | 468 ± 58 nM |
| 36 | N$^6$-benzyladenosine-N1-oxide | 864 ± 88 nM | 8,530 ± 1,250 nM | 7,250 ± 1,680 nM |
| 37 | N'-(4-nitrobenzyl)NECA | 341 ± 52 nM | 190 ± 52 nM | 60 ± 3 nM |
| 38 | N'-(2-nitrobenzyl)NECA | 196 ± 52 nM | 83.5 ± 9.5 nM | 27 ± 5 nM |
| 39 | N$^6$-benzyl-5'-carboxamidoadenosine | 580 ± 99 nM | 423 ± 46 nM | 246 ± 35 nM |
| 40 | N$^6$-benzyl-NMCA | 898 ± 124 nM | 597 ± 42 nM | 16 ± 1 nM |
| 41 | N$^6$-(3-bromobenzyl)-NMCA | 65 ± 2 nM | 64 ± 9 nM | 1.0 ± 0.3 nM |
| 42 | N$^6$-(3-iodobenzyl)-NMCA (3-IB-MECA) | 54 ± 5 nM | 56 ± 8 nM | 1.1 ± 0.3 nM |
| 43 | N$^6$-(3-nitrobenzyl)-NMCA | 735 ± 5 nM | 441 ± 45 nM | 19 ± 1 nM |

TABLE 1-continued

Affinities of selected compounds at $A_1$, $A_2$ and $A_3$ receptors indicated as either $K_i$ (nM) or percent displacement at a concentration of 100 μM, unless otherwise indicated. Values are means of 3–5 experiments ± SEM. Values without SEM are taken from the literature.

| # | Compound | $A_1$-affinity[a] | $A_2$-affinity[b] | $A_3$-affinity[c] |
|---|---|---|---|---|
| 44 | $N^6$-(3-aminobenzyl)-NMCA | 1,000 ± 60 nM | 794 ± 118 nM | 28 ± 13 nM |
| 45 | $N^6$-(3-acetamidobenzyl)-NMCA | 7,370 ± 690 nM | 12.5 ± 1.9% | 65 ± 15 nM |
| 46 | $N^6$-(3-methylbenzyl)-NMCA | 322 ± 23 nM | 415 ± 33 nM | 10 ± 3 nM |
| 47 | $N^6$-(3-trifluoromethylbenzyl)-NMCA | 496 ± 50 nM | 574 ± 49 nM | 31 ± 6 nM |
| 48 | $N^6$-(4-chlorobenzyl)-NMCA | 478 ± 38 nM | 2,730 ± 210 nM | 17 ± 10 nM |
| 49 | $N^6$-(4-bromobenzyl)-NMCA | 516 ± 38 nM | 2,460 ± 380 nM | 12 ± 5 nM |
| 50 | $N^6$-(4-aminobenzyl)-NMCA | 431 ± 45 nM | 1,590 ± 180 nM | 14 ± 3 nM |
| 51 | $N^6$-(3-iodo-4-aminobenzyl)-NMCA (AB-MECA) | 18 ± 5 nM | 316 ± 43 nM | 1.27 ± 0.18 nM |
| 52 | $N^6$-(3-sulfobenzyl)-NMCA triethylammonium salt | >10,000 nM | >10,000 nM | 1,310 ± 110 nM |
| 53 | $N^6$-(4-sulfobenzyl)-NMCA triethylammonium salt | 0% | 0% | 4,500 ± 480 nM |
| 54 | $N^6$-benzyl-NECA | 87 nM | 95 nM | 6.8 nM |
| 55 | $N^6$-(R-phenylethyl)-NECA | 3.2 ± 0.1 nM | 259 ± 15 nM | 18 ± 4 nM |
| 56 | $N^6$-(S-phenylethyl)-NECA | 65 ± 4 nM | 1,650 ± 120 nM | 494 ± 91 nM |
| 57 | $N^6$-(3-fluorobenzyl)-NECA | 51 ± 7 nM | 32 ± 4 nM | 10.7 ± 1.2 nM |
| 58 | $N^6$-(3-chlorobenzyl)-NECA | 22 ± 3 nM | 19.0 ± 0.3 nM | 1.1 ± 0.3 nM |
| 59 | $N^6$-(3-bromobenzyl)-NECA | 10.9 ± 1.5 nM | 6.2 ± 0.7 nM | 2.8 ± 1.9 nM |
| 60 | $N^6$-(3-iodobenzyl)-NECA | 7.7 ± 0.9 nM | 7.2 ± 0.6 nM | 0.88 ± 0.21 nM |
| 61 | $N^6$-(2-nitrobenzyl)-NECA | 31 ± 4 nM | 24 ± 3 nM | 2.8 ± 0.5 nM |
| 62 | $N^6$-(3-nitrobenzyl)-NECA | 78 ± 10 nM | 35 ± 7 nM | 8.7 ± 1.2 nM |
| 63 | $N^6$-(4-nitrobenzyl)-NECA | 49 ± 9 nM | 574 ± 64 nM | 9.0 ± 1.3 nM |
| 64 | $N^6$-(3-methylbenzyl)-NECA | 36.5 ± 1.2 nM | 17.7 ± 1.8 nM | 1.2 ± 0.1 nM |
| 65 | $N^6$-(2-methoxybenzyl)-NECA | 52 ± 5 nM | 21 ± 3 nM | 7.1 ± 0.3 nM |
| 66 | $N^6$-(3-methoxybenzyl)-NECA | 69 ± 8 nM | 38 ± 6 nM | 4.3 ± 0.6 nM |
| 67 | $N^6$-(4-methoxybenzyl)-NECA | 209 ± 30 nM | 609 ± 34 nM | 11 ± 3 nM |
| | ribose-modified adenosines | | | |
| 68 | β-L-adenosine[6] | 29,000 ± 4,700 nM | 25.4 ± 1.1% | 9.5 ± 4.2% |
| 69 | α-D-adenosine[3] | 350,000 nM | 128,000 ± 25,000 nM | 14.2 ± 6.5% |
| 70 | 2'-deoxyadenosine[3] | 30.9 ± 8.0% | 38.9 ± 2.9% | 28.3 ± 2.3% |
| 71 | 2'-O-methyladenosine[6] | 29.4 ± 7.5% | 49.0 ± 5.0% | 42.9 ± 9.4% |
| 72 | 3'-deoxyadenosine (Cordycepin)[3] | 5.8 ± 2.8% | 26.3 ± 3.4% | 32.7 ± 2.0% |
| 73 | 5'-deoxyadenosine[3] | 269 ± 135 nM | 596 ± 54 nM | 2,830 ± 460 nM |
| 74 | 5'-deoxy-5'-aminoadenosine[6] | 42,700 ± 6,000 nM | 38,500 ± 3,800 nM | 30.6 ± 2.2% |
| 75 | 5'-deoxy-5'-methylthioadenosine[3] | 281 nM | 1,100 nM | 1.420 ± 530 nM |
| 76 | 5'-deoxy-5'-isobutylthio adenosine[3] | 1,140 ± 130 nM | 6,890 ± 1,750 nM | 3,360 ± 360 nM |
| 77 | S-adenosylmethionine[3] | 675 ± 87 nM | 2,780 ± 250 nM | 2,470 ± 450 nM |
| 78 | AMP[4] | —[d] | 57.5 ± 4.0% | 17.2 ± 6.3% |
| 79 | adenine-β-D-arabinofuranoside[6] | 20.2 ± 8.4% | 26.0 ± 8.4% | 23.7 ± 3.8% |
| 80 | β-D-psicofuranosyladenine[6] | 36.1 ± 4.9% | 51.5 ± 7.4% | 21.1 ± 0.9% |
| | non-adenosine nucleosides | | | |
| 81 | xanthosine[5] | 9.1 ± 2.4% | 8.5 ± 2.5% | 23.4 ± 8.8% |
| 82 | uridine[5] | 14.3 ± 6.9% | 2.8 ± 5.2% | 18.9 ± 2.8% |
| 83 | thymidine[5] | 23.4 ± 2.5% | 1.7 ± 3.4% | 21.3 ± 4.9% |
| 84 | cytidine[5] | 18.0 ± 1.2% | 16.0 ± 1.5% | 24.5 ± 10.2% |
| 85 | inosine[1] | 16,700 ± 2,900 nM | 50,000 ± 12,700 nM | 45,100 ± 38,800 nM |
| 86 | guanosine[3] | 27,800 ± 9,600 nM | 8,500 ± 15,700 nM | 98,500 ± 28,700 nM |
| 87 | (4-nitrobenzyl)-6-thioguanosine | 15,000 ± 3,500 nM | 48,500 ± 11,300 nM | 40,700 ± 26,300 nM |
| 88 | 6-thioguanosine[3] | 44.2 ± 2.3% | 27.7 ± 5.8% | 44.8 ± 18.1% |
| 89 | 6-thiopurine riboside[3] | 61.2 ± 3.9% | 33.6 ± 3.3% | 41.9 ± 5.0% |
| 90 | NMCI | 0% | 6.2 ± 4.2% | 6,220 ± 1,220 nM |
| 91 | NECI | 43.7 ± 10.3% | 30.6 ± 2.3% | 5,000 ± 1,150 nM |
| | non-xanthine adenosine antagonists | | | |
| 92 | CP 66713[8] | 270 nM | 21 nM | 29.7 ± 7.8% |
| 93 | CGS 15943[9] | 21 nM | 3.3 nM | 38.0 ± 14.5% |
| 94 | IQA | 1,600 nM | 1,400 nM | 32.6 ± 10.8% |
| 95 | 9-ethyl-$N^6$cyclopentyladenine[7] | 440 nM | 17,000 nM | 30.4 ± 9.1% |
| 96 | EHNA | 455 ± 10 nM | 59.6 ± 2.8% | 57.5 ± 14.3% |
| 97 | amiloride | 11,000 nM | 17,000 nM | 22.0 ± 3.5% |
| | simple alkylxanthines | | | |
| 98 | xanthine (X)[1] | 298,000 nM | 16.2 ± 2.6% | 14.0 ± 7.9% |
| 99 | 1-methylX | 11,400 nM | 36,200 nM | 11.1 ± 1.6% |
| 100 | 3-methylX | 35,000 nM | 38.0 ± 0.9% | 18.1 ± 6.7% |
| 101 | 7-methylX | 52.3 ± 7.9% | 37.7 ± 4.9% | 16.4 ± 9.6% |
| 102 | 9-methylX | 26.6 ± 3.2% | 16.1 ± 1.9% | 22.8 ± 9.5% |
| 103 | 1,3-dimethylX (theophylline, T) | 8,500 nM | 25,000 nM | 23.1 ± 9.5% |
| 104 | 1,7-dimethylX (paraxanthine) | 30,000 nM | 19,400 ± 3,500 nM | 15.5 ± 12.1% |

TABLE 1-continued

Affinities of selected compounds at $A_1$, $A_2$ and $A_3$ receptors indicated as either $K_i$ (nM) or percent displacement at a concentration of 100 μM, unless otherwise indicated. Values are means of 3–5 experiments ± SEM. Values without SEM are taken from the literature.

| # | Compound | $A_1$-affinity[a] | $A_2$-affinity[b] | $A_3$-affinity[c] |
|---|---|---|---|---|
| 105 | 1,9-dimethylX[2] | 29.4 ± 1.6% | 6.0 ± 6.3% | 17.0 ± 7.9% |
| 106 | 3,7-dimethylX (theobromine)[3] | 83,400 nM | 187,000 nM | 19.9 ± 7.1% |
| 107 | 3,9-dimethylX[2] | 19.7 ± 7.9% | 4.2 ± 5.9% | 19.0 ± 6.8% |
| 108 | 1-methyl-3-isobutyl (IBMX) | 7,000 nM | 16,000 nM | 30.1 ± 12.4% |
| 109 | 1,3-dibutylX[6] | 500 nM | 2,930 ± 700 nM | 143,000 ± 29,000 nM |
| 110 | 1,3-dihexylX[6] | 1,260 ± 90 nM | 14.3 ± 3.0% (10 μm) | 9.2 ± 6.5% (10 μM) |
| 111 | 1,3-dibenzylX[6] | 2,000 nM | 3.61 ± 0.94% μM) | 20.3 ± 8.5% (10 μM) |
| 112 | 1,3,7-trimethylX (caffeine, C) | 29,000 nM | 48,000 nM | 30.1 ± 12.4% |
| 113 | 1,3,9-trimethylX (isoC) | >100,000,000 nM | 14.4 ± 5.7% | 13.2 ± 12.4% |
| 114 | 2-thio-3-propylX[6] | 26,100 ± 1,500 nM | 32,500 ± 4,800 nM | 27.7 ± 11.3% |
| | 7-substituted alkylxanthines | | | |
| 115 | 7-benzylT[6] | 6,000 nM | 46,000 | 29.7 ± 0.2% |
| 116 | 7-β-hydroxyethylT | 105,000 nM | 17,400 ± 900 nM | 21.1 ± 13.3% |
| 117 | T-7-riboside | 27,000 ± 3,200 nM | n.t. | 89,400 ± 13,400 nM |
| 118 | 1,3-dipropylX-7-riboside (DPXR) | 15,900 ± 1,800 nM | 32.0 ± 1.1% | 81,200 ± 10,700 nM |
| 119 | 1,3-dibutylX-7-riboside (DBXR) | 4,190 ± 1,030 nM | 19,500 ± 4,200 nM | 6,030 ± 2,320 nM |
| 120 | 1-benzyl-3-butyl-7-(1-β-D-ribofuranosyl)X | 2,190 ± 390 | 3,800 ± 2,200 | 12,900 ± 300 |
| 121 | 1-butyl-3-benzyl-7-(1-β-D-ribofuranosyl)X | 1,720 ± 30 | 4,510 ± 1,230 | 12,400 ± 20 |
| 122 | 1,3-dibutyl-7-(5-methoxycarbonyl-β-D-ribofuranosyl)X | n.t. | n.t. | 3,230 ± 590 |
| 123 | 1,3-dibutyl-7-(1-β-D-ribofuranuronamido)X | 2,940 ± 350 | 59,200 ± 5,200 | 15,300 ± 700 |
| 124 | 1,3-dibutyl-7-(1-β-D-ribofuranosyl)X-5'-methyluronamide | 30% | 39,200 | 229 ± 27 |
| 125 | 1,3-dibutyl-7-(1-β-D-ribofuranosyl)X-5'-dimethyluronamide | n.t. | n.t. | 228,000 ± 9,000 |
| 126 | 1,3-dibutyl-7-(1-β-D ribofuranosyl)X-5'-ethyluronamide | 7,500 | 17,000 | 602 ± 76 |
| | 8-substituted alkylxanthines | | | |
| 127 | 8-phenylT | 86 nM | 850 nM | 12.0 ± 6.0% |
| 128 | 8-cyclopentylT | 11 nM | 1,400 nM | 38.7 ± 2.5% |
| 129 | 8-cyclopentyl-1-propylX[6] | 226 ± 37 nM | 48,700 ± 5,000 nM | 22.6 ± 7.7% |
| 130 | 8-cyclopentyl-1,3-dipropylX (CPX) | 0.46 nM | 340 nM | 18.7 ± 2.9% (10 μM) |
| 131 | 8-cyclohexylC[6] | 28,000 nM | 10,400 ± 2,600 nM | 35.2 ± 1.8% |
| 132 | 8-chloroT[1] | 30.2 ± 6.7% | 24.7 ± 3.9% | 16.8 ± 9.5% |
| 133 | XAC | 1.2 nM | 63 nM | 7.1 ± 0.9% |
| 134 | CSC | 28,200 nM | 54 nM | 4.2 ± 5.1% (10 μM) |
| 135 | 8-sulfophenyl-1,3-dipropylX | 140 nM | 790 nM | 21.9 ± 6.2% |

[a]Displacement of [$^3$H]PIA (or [$^3$H]CHA) binding from rat brain membranes.
[b]Displacement of [$^3$H]CGS 21680 (or [$^3$H]NECA in the presence of 50 nM CPA) from rat striatal membranes.
[c]Displacement of [$^{125}$I]APNEA or [$^{125}$I]AB-MECA binding from membranes of CHO cells stably transfected with the rat $A_3$-cDNA.
[d]AMP displayed an extremely high slope factor (3.62 ± 0.39 μM) in $A_1$ displacement. The apparent $K_i$ was 47.5 ± 6.5 μM.
[e]Values at $A_1$ and $A_2$ receptors are taken from Bruns et al., Mol. Pharmacol., 29, 331–346 (1986).
[1]Aldrich, Milwaukee, WI
[2]Fluka, Ronkonkoma, NY
[3]Sigma, St. Louis, MO
[4]Boehringer Mannheim, Indianapolis, IN
[5]Janssen/Spectrum, Gardena, CA
[6]Dr. J. Daly, National Institutes of Health, Bethesda, MD
[7]Dr. R. Olsson, University of South Florida, Tampa, FL
[8]Dr. R. Sarges, Pfizer, Groton, CT
[9]Dr. J. Francis, Ciba-Geigy, Summit, NJ
[10]Research Biochemicals International, Natick, MA The affinity of adenosine, itself, cannot be accurately determined in this binding assay, due to the presence of adenosine deaminase, which is required to degrade endogenously generated adenosine. Hence, it is not possible to directly compare the affinities of adenosine with the derivatives tested here. The affinity of adenosine has previously been estimated at 30 μM (Zhou et al., supra), but this value should only be taken as a rough approximation.

The most potent compounds at the $A_3$ receptor are $N^6$-substituted and/or 5'-uronamide substituted adenosine derivatives. In a series of $N^6$-aryl(alkyl) substituted compounds, $N^6$-benzyladenosine is more potent ($K_i$ 120 nM) than $N^6$-phenyladenosine ($K_i$ 802 nM) or $N^6$-phenethyladenosine ($K_i$ 240 nM) but essentially nonselective. Introduction of a p-sulfo group in $N^6$-phenyladenosine slightly enhances affinity (SPA, $K_i$ 526 nM) for the $A_3$ receptor. Two other $N^6$-sulfo derivatives, $N^6$-3-(4-sulfophenyl)propyladenosine and $N^6$-4-(4-sulfophenyl)butyladenosine, have affinities in the same range (see Table, supra), but the 2-sulfoethyl derivative, which has a shorter $N^6$-substituent, is considerably less potent ($K_i$ 32.4 $\mu$M). The polar sulfo group is apparently tolerated at $A_3$ receptors, and sulfo substitution appears to shift affinity in the direction of $A_3$ selectivity. The 5'-N-methylcarboxamide analogue of $N^6$-benzyladenosine was 37–56 fold selective for $A_3$ receptors over $A_2$ and $A_1$ receptors, respectively, whereas the 5'-N-cyclopropylcarboxamide analogue was not selective and much less potent. Although the 5'-N-methyl substitution was generally favored over the 5'-N-ethyl substitution, there were several exceptions, such as the 3-nitro and 3-methyl analogues, in which the potency was more favorable in the N-ethyl series. The $N^6$-cycloalkyl derivatives, 35 CHA and CPA, are among the more potent compounds at $A_3$ ($K_i$ 167 and 240 nM, respectively), as is the $N^6$-functionalized congener ADAC ($K_i$ 281 nM). The $N^6$-substituted compound, DPMA, has moderate potency at $A_3$ ($K_i$ 3.57 $\mu$M). The affinity of $N^6$-dimethyladenosine is quite low ($K_i$ 32.5 $\mu$M). The affinity of $N^6$-benzyl-$N^6$-methyladenosine and $N^6$-dimethyl-NECA is also considerably lower than the parent compounds $N^6$-benzyladenosine and NECA. Thus, although disubstitution at $N^6$ reduces affinity, it enhances selectivity for $A_3$ receptors (e.g., $N^6$-dimethyl-NECA is 4-fold selective for $A_3$ over $A_1$ and 6-fold for $A_3$ over $A_2$). NECA (5'-N-ethylcarboxamide adenosine) is relatively potent ($K_i$ 113 nM). The effects of $N^6$- and C5'-substitutions appear to reinforce each other. Thus, the 5'-N-ethylcarboxamide of CHA is considerably more potent than either CHA ($K_i$ 167 nM, 10-fold) or NECA ($K_i$ 113 nM, 7-fold), and, with a $K_i$ of 16 nM, it is a highly potent compound at $A_3$ receptors. Likewise, $N^6$-dimethyl-NECA is 14-fold more potent than $N^6$-dimethyladenosine at $A_3$ receptors. $N^6$-benzyl-NECA has a high $A_3$ affinity, with a $K_i$ value of 6.8 nM, and it is 18-fold more potent than the parent compound $N^6$-benzyladenosine at $A_3$ receptors. $N^6$-benzyl NECA is also $A_3$ selective (13-fold selective for $A_3$ over $A_1$ and 14-fold selective for $A_3$ over $A_2$).

Comparisons of benzyl group substitutions were made for both the N-ethyl and the N-methyluronamide series. The R-isomer of $N^6$-phenylisopropyl-adenosine is favored over the S-isomer. For the doubly modified $N^6$-(1-phenylethyl)-5'-uronamido-adenosine analogues, the R-configuration is also favored by a factor of 27 at $A_3$ receptors. The presence of a sulfo group on the benzyl substituent (Ijzerman et al., Drug Design Disc., 9, 49–68 (1992)) is expected to result in selectivity for peripheral versus central $A_3$ receptors in vivo (see compounds 52 and 53 in Table 1).

Among $N^6$-benzyl-5'-N-ethyluronamides, selectivity for $A_3$ vs. $A_1$-receptors ranged from 4- to 30-fold and was greatest for the 3-methyl derivative. 3-Chloro-, 3-methoxy-, and 3-nitro-derivatives were also very selective for $A_3$ over $A_1$ receptors. Selectivity for $A_3$ over $A_{2a}$ receptors ranged from 2- to 64-fold and was greatest for the 4-nitro derivative and the 4-methoxy derivative. Substitution at the 4 position provided high selectivity for $A_3$ over $A_{2a}$ receptors in both the N-methyl and N-ethyl series. Substitution at the 3-position generally favored $A_3$-potency and selectivity. 3-Halo benzyl derivatives were particularly potent. The 3- and 4-bromo derivatives in the 5'-N-methyl series, respectively, were both relatively selective, but the affinity at $A_3$ receptors was 6-fold greater with substitution at the 3-position than at the 4-position. In the 5'-N-ethyl series, the order of potency at $A_1$ and $A_{2a}$ receptors was I~Br>Cl>F. At $A_3$ receptors, the order was I~Cl>Br>F. In the 5'-N-ethyl series, the 3-iodobenzyl analogue and to a lesser degree the 3-bromo analogue were very highly potent and selective for $A_3$ receptors. 5'-N-Methyl-$N^6$-(3-iodobenzyl)adenosine displayed a $K_i$ value of 1.0 nM at $A_3$ receptors and selectivity over $A_1$ and $A_{2a}$ receptors of 49 and 51-fold, respectively.

The 3-methyl and 3-trifluoromethyl analogues were prepared in the N-methyl series. The trifluoromethyl analogue was weaker at $A_3$ receptors. Thus, an electron withdrawing group at the 3-position is not favorable for potency, further supported by the relatively modest potency of the 3-nitro derivative.

The acetamido derivative demonstrated that there is an unfavorable interaction at this site on the receptor. The 3-acetamido group is not favored at $A_1$ and $A_3$ receptors and entirely disallowed at $A_{2a}$ receptors. Thus, $N^6$-(3-acetamidobenzyl)-NMCA is 110-fold and >500-fold selective for $A_3$ over $A_1$ and $A_{2a}$ receptors, respectively.

$N^6$-(4-amino-3-iodobenzyl)-NMCA weakly displaced radioligand from $A_3$ but not $A_1$ or $A_{2a}$ receptors; thus, it is a highly selective ligand. It is evident that a negative charge at the 4-benzyl position is poorly tolerated at all three receptor subtypes.

The 8 position of the purine moiety is not amenable to substitution in $A_3$ receptor binding. The 2-position may be substituted without eliminating recognition at $A_3$ receptors; however, among the few analogues examined there was no indication of enhancement of $A_3$ selectivity.

Modification of the N-1 position (either oxidation to the N-oxide or 1-deaza analogues) is tolerated at $A_3$ receptors. The 5'-N-ethyl uronamide modification was combined with various changes at the N-1 position. NECA-N-1-oxide was not selective but the loss of potency versus NECA was greater for $A_1$ and $A_{2a}$ receptors than for $A_3$ receptors. Introduction of larger groups, such as 2- and 4-nitrobenzyl, into NECA did not affect potency at $A_1$ and $A_{2a}$ receptors but increased potency at $A_3$ receptors by an order of magnitude.

Certain C2-modifications are tolerated to a degree at the $A_3$ receptor. 2-chloroadenosine and 2-phenylaminoadenosine are of intermediate potency ($K_i$ 1.9 and 4.4 $\mu$M, respectively). An $N^6$-substituted derivative (2-chloro-$N^6$-CPA, $K_i$ 237 nM), and one bearing a 5'-N-ethylcarboxamide group (CGS 21680, $K_i$ 584 nM), are more potent C2-substituted derivatives.

With regard to modifications of the ribose moiety, both the L-enantiomer and the $\alpha$-anomer of adenosine are virtually inactive ($IC_{50}$>>100 $\mu$M). Psicofuranosyladenine, which contains an extra $CH_2OH$-group at C1', is also very weak. 2'-Deoxy-, 2'-O-methyl and 3'-deoxyadenosine all have low affinity ($IC_{50}$>100 $\mu$M), and inversion of the stereochemistry of the 2'-OH group (adenine-$\beta$-D-arabinofuranoside) similarly results in a low affinity compound. Thus, the presence of the 2'-OH in the S-configuration and the 3'-OH appear to be essential for high affinity. The 5'-position is more amenable to modifications than the 2'- or the 3'-position. 5'-Deoxy, 5'-thioether and 5'-uronamide substitutions are tolerated at $A_3$ receptors. The 5'-deoxy derivative of adenosine is moderately potent (Ki 2.83 $\mu$M), and, as previously indicated, the 5'-N-ethylcarboxamide derivative (NECA) is one of the more potent compounds tested ($K_i$ 113 nM). Although it is an $A_3$ agonist, it is not $A_3$ selective—favoring $A_1$ and $A_{2a}$ receptors over $A_3$ receptors by an order of magnitude in affinity. The primary carboxamide (CA) is weaker than NECA at $A_3$ receptors with roughly the same selectivity ratios. NMCA was the most favored 5' uronamide in binding to $A_3$ receptors but was nonselective, although moderately potent at $A_3$ receptors. 5'-N-Aminoethylamino-CA and 5'-N-boc-aminoethylamino-CA were much less potent than NECA in receptor affinity but were $A_3$-selective. Some 5'-deoxyadenosine derivatives, including those with methylthio-, isobutylthio- and methionine substituents have affinities in the lower micromolar range, whereas 5'-deoxy-5'-aminoadenosine and AMP (bearing a 5'-phosphate group) are virtually inactive ($IC_{50}$>100 μM). These results suggest that the ribose domain of the $A_3$ receptor may be quite similar to the ribose domains of the $A_1$ and $A_2$ receptors.

6-Thiopurine riboside and 8-bromoadenosine both have low affinity ($IC_{50}$>100 μM) at $A_3$. A bulky 8-substituent forces the ribose moiety into a predominantly syn conformation, which is a likely explanation for its inactivity. 7-Deazaadenosine has a $IC_{50}$>>100 μM, which indicates the importance of N7. 3-Deazaadenosine is slightly more potent, with a $K_i$ of 62 μM. 1-Deaza-2-chloro-CPA (DCCA, $K_i$ 770 nM) is three-fold less potent than 2-chloro-CPA ($K_i$ 237 nM). This suggests that the presence of N1 is not crucial, i.e., if the nitrogen is replaced with carbon, for example, the compound will still react with the $A_3$ receptor. The $N^1$-oxides of adenosine, NECA and $N^6$-benzyladenosine, are moderately potent compounds ($K_i$ 3.09, 0.47 and 7.25 μM, respectively).

Of the unsubstituted non-adenine nucleosides tested, only inosine ($K_i$ 45 μM) and guanosine ($K_i$ 99 μM) show some affinity for the $A_3$ receptor. The 5'-N-ethylcarboxamide derivative of inosine (NECI) is more potent ($K_i$ 5 μM), which is consistent with the affinity-enhancing effect of the 5'-carboxamido substituent of NECA. The 5'-N-methylcarboxamide derivative of inosine (NMCI) has approximately the same affinity as NECI but apparently has increased selectivity. NECI is also selective for $A_3$ receptors, having an $IC_{50}$ larger than 100 μM at $A_1$ and $A_2$ receptors. An adenosine transport inhibitor, (4-nitrobenzyl)-6-thioguanosine ($K_i$ 41 μM), is slightly more potent than the parent compound, guanosine.

Of the non-xanthines tested, CGS 15943, CP 66713, 1H-imidazo[4,5-c]quinolinamine, 9-ethylcyclopentyladenine and amiloride did not appear to be particularly potent, with $K_i$-values in the range of 100 μM or larger. The adenosine deaminase inhibitor, erythro-9-(2-hydroxy-3-nonyl)adenine (EHNA), was somewhat more potent with an $IC_{50}$ slightly better than 100 μM (57.5% displacement at 100 μM).

Xanthine was found to be a very weak displacer of [$^{125}$I]APNEA binding (14% at 100 μM). Substitutions at the 1- and the 3-positions enhanced affinity. Compared to theophylline (1,3-dimethylxanthine, 23.1% at 100 μM), 1,3-dibutylxanthine is more potent ($K_i$ 143 μM). 1,3-Dihexylxanthine (9.2% at 10 μM) and 1,3-dibenzylxanthine (20.3% at 10 μM) also seem more potent than theophylline, but their limited solubility precludes direct comparison. Still, even the most potent of these 1,3-substituted xanthines is quite weak at $A_3$ receptors.

The 8-substituents do not appear to contribute much to affinity, and none of the 8-substituted xanthine derivatives tested is particularly potent (see Table, supra). Substitutions at the 7-position appear to be tolerated; both caffeine and 7-benzyltheophylline are slightly more potent at $A_3$ receptors than the 7-unsubstituted parent compound, theophylline.

Example 36

This example describes the distribution of $A_3$ receptors in mouse brain.

Twenty white male mice were killed by cervical fracture. Brains were rapidly removed, placed in ice-cold 50 mM Tris-HCl buffer (pH 7.4), and cortex, cerebellum, hippocampus, brain stem and striatum were dissected. Tissue was homogenized in 20 ml of ice-cold 50 mM Tris-HCl buffer (pH 7.4) using a Polytron (setting #6) for 10 seconds. The homogenates were centrifuged at 35000×g for 15 min at 4° C. The pellets then were resuspended in fresh volume of the same buffer, homogenized with the Polytron and re-centrifuged. The final pellet was stored at −70° C. before use in the receptor binding assay. For the binding assay, membranes were diluted at a protein concentration of 1–3 mg/ml. Protein concentrations were determined by the BCA protein assay reagents (Pierce Chemical Co., Rockford, Ill.) using bovine albumin as a standard.

[$^{125}$I]AB-MECA binding to $A_3$ adenosine receptor in mouse brain membranes was performed in 50 mM Tris, 10 mM $MgCl_2$, 1 mM EDTA buffer (pH 7.4) containing 100 μl membrane suspension with ADA (3 units/ml) added. Where applicable, the $A_1$ component of binding was eliminated by the addition of 100 nM CPX (Research Biochemicals International, Natick, Mass.) to the medium. The final concentration of [$^{125}$I]AB-MECA ranged from 0.1–4 nM, while the final volume of the preparation was 0.5 ml. Incubations were carried out in duplicate for 90 min at 25° C. Nonspecific binding was defined in the presence of 40 μM R-PIA ($N^6$-R-phenylisopropyladenosine) and constituted approximately 30% of the total binding. Binding reactions were terminated by filtration through Whatman GF/B filters using a Brandel M24R cell harvester (Brandel Gaithersburg, Md.). Filters were washed three times with 3 ml ice-cold buffer and placed in vials. Radioactivity was determined in a Beckman 5500B gamma-counter.

FIG. 1 is a graph of $A_3$ adenosine receptor binding versus concentration of [$^{125}$I]AB-MECA (nM), which shows a representative saturation curve for binding at $A_3$ adenosine receptors in mouse cerebellar membranes using [$^{125}$I]AB-MECA in the presence of 100 nM CPX. The $K_d$ value for binding to $A_3$ receptors was 1.39+0.04 nM with a $B_{max}$ of 14.8+2.1 fmol/mg protein.

Linear fitting of Scatchard plots and the saturation experiments, analyzed by non-linear regression using computer program GraphPad InPlot (Version 4.0, San Diego, Calif.), gave similar results for determination of $K_d$ and $B_{max}$ values. Each experimental result is reported as mean±S.E.M. from three or four experiments. The high affinity radioligand, [$^{125}$I]AB-MECA (Ramkumar et al., *J. Biol. Chem.*, 268, 16887–16890 (1993)), bound specifically to both $A_1$ and $A_3$ adenosine receptors in membranes prepared from regions of NIH Swiss mouse brains. Specific binding represented ca. 70% of total binding, with $B_{max}$ values (expressed as fmol specifically bound/mg protein in parentheses): hippocampus (215±17), cortex (159±15), cerebellum (120±5), and striatum (123±23). Scatchard analysis indicated $K_d$ values ranging from 1.9 to 2.8 nM. The $A_{2a}$ selective antagonist 8-(3-chlorostyryl)caffeine (CSC) failed to displace specific binding of [$^{125}$I]AB-MECA. The specific binding consisted of two components, since the $A_1$ selective antagonist 1,3-dipropyl-8-cycylopentylxanthine (CPX) completely displaced most but not all of the high affinity [$^{125}$I]AB-MECA binding (sigmoidal competition curves had $K_i$ values ranging from 2 to 8 nM). Thus, the majority of the specific binding of [$^{125}$I]AB-MECA was to high affinity $A_1$ receptors. The residual binding, which was not displaced by CPX at concentrations as high as 1 μM, represented binding to $A_3$ adenosine receptors. Low levels of $A_3$ adenosine receptors (18% of total specific binding using 0.4 nM [$^{125}$I]AB-MECA in the presence of 100 nM CPX) were detected in the cerebellum and striatum, with even lower levels in the hippocampus and cortex (7–9% of total specific binding). A Scatchard analysis showed that, in the presence of 100 nM CPX, the $K_d$ for binding of [$^{125}$I]AB-MECA to cerebellar $A_3$ receptors was 1.39±0.04 nM with a $B_{max}$ of 14.8±2.1 fmol/mg protein (n=3).

$A_3$ receptors were found to be present in the mouse brain, with highest density in the cerebellum and striatum. Thus, the striatum, which is critical to the locomotor depressant effects of $A_{2a}$ agonists (Nikodijevic et al., FEBS Letters, 261, 67–70 (1990)), contains $A_3$ receptors at a density at least 10-fold lower than $A_{2a}$ receptors. Since previously reported levels of mRNA coding for $A_3$ receptors in rat brain indicated the greatest density in hippocampus and cerebellum (De et al., Soc. for Neuroscience, 1993, Abstract 42.11), there is either a species difference between rat and mouse, or the level of message is not entirely predictive of the level of receptor density. $A_1$ receptors are localized in high density in the hippocampus and appear to be involved in the cerebroprotective effects of adenosine (Schingnitz et al., Nucleosides Nucleotides, 10, 1067–1076 (1991)). A3 receptors were also detected in the hippocampus but at densities 1–2 orders of magnitude lower than $A_1$ receptors.

Example 37

This example describes the use of an $A_3$-selective adenosine receptor agonist as a locomotor depressant.

Adult male mice (NIH Swiss Strain, 25–30 g) were housed in groups of ten animals per cage with a light-dark cycle of 12:12 hr. The animals were given free access to standard pellet food and water and were acclimatized to laboratory conditions for 24 hr prior to testing. Each animal was used only once in the activity monitor.

A potent ($K_i$ 1.1±0.3 nM at rat brain $A_3$ receptors) and selective (50-fold less potent in binding to either $A_1$ or $A_{2a}$ rat brain receptors) $A_3$ agonist, 3-IB-MECA, was selected for in vivo studies. The locomotor effects in mice of 3-IB-MECA alone or in combination with potent and selective $A_1$ and $A_{2a}$ receptor antagonists were examined.

Locomotor activity of individual animals was studied in an open field using a Digiscan activity monitor (Omnitech Electronics Inc., Columbus, Ohio) equipped with an IBM-compatible computer. The computer-tabulated measurements represent multivariate locomotor analysis with specific measures, such as simultaneous measurements of ambulatory, rearing, stereotypical, and rotational behaviors. Data were collected in the morning, for three consecutive intervals of 10 min each, and analyzed as a group. Statistical analysis was performed using the Student t-test. The results are reported as mean ± standard error for each point. All drugs were dissolved in a vehicle consisting of a 20:80 v/v mixture of Alkamuls EL-620 (Rhone-Poulenc, Cranbury, N.J.) and phosphate-buffered saline, except for CSC, which was dissolved initially in DMSO and diluted in at least 20 volumes of vehicle. Drugs were administered i.p. in a volume corresponding to 5 ml/kg body weight. Where applicable, the antagonist was injected 10 minutes before the agonist. After injection of agonist, the mouse was placed in the activity monitor for 5 min before data collection was begun.

Figure 2:
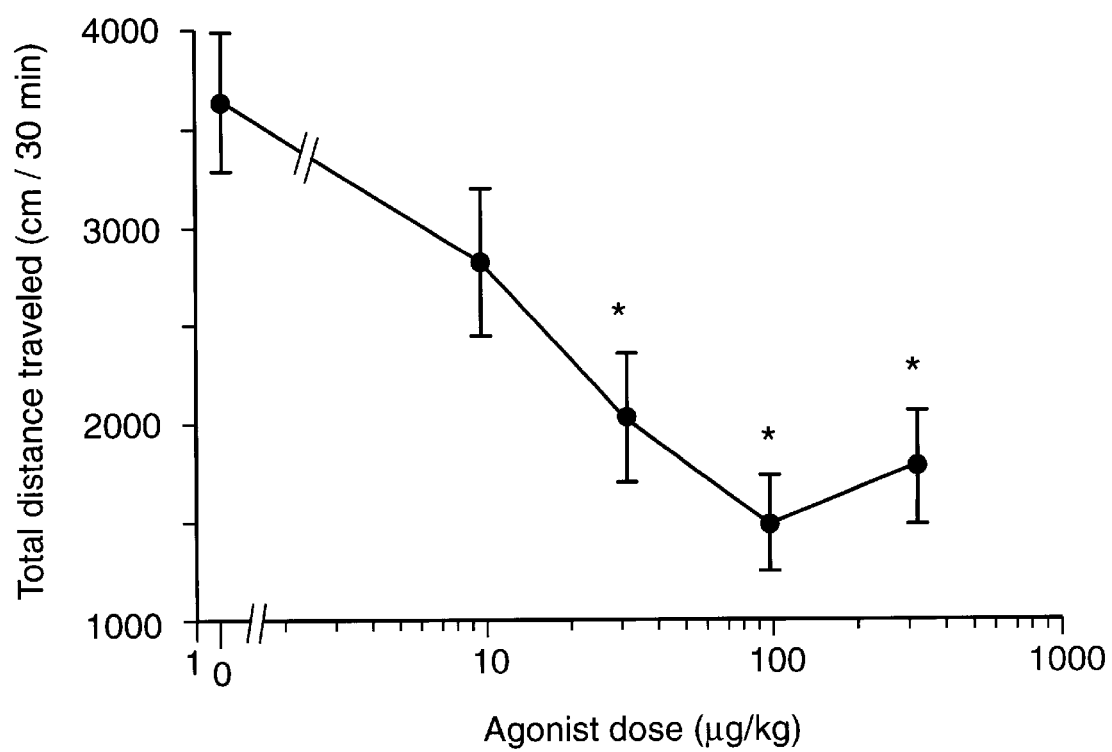
FIG. 2 is a graph of total distance traveled by mice (cm/30 min) versus dose of $A_3$ adenosine receptor agonist 3-IB-MECA (μg/kg).

FIG. 2 is a graph of total distance traveled by the mice (cm/30 min) versus dose of the $A_3$ adenosine receptor agonist 3-IB-MECA (μg/kg), which shows the locomotor activity in mice. The *p value is<0.05 vs. vehicle control (n=6–19). 3-IB-MECA administered i.p. in a dose range of 0.01 to 0.3 mg/kg was found to be a locomotor depressant (based on total distance travelled), with a threshold dose of 0.01 mg/kg and maximal depression reached at about 0.1 mg/kg (FIG. 2). Unlike depression elicited by selective $A_1$ and $A_{2a}$ agonists, the depression did not exceed 90% at the higher doses, but reached a plateau at ca. 60% below control level (FIG. 2). Vertical activity, stereotype counts, and rotational movement were depressed in a dose-dependent manner following administration of 3-IB-MECA; however, average distance per move and average speed were not changed significantly.

Administration of 3-IB-MECA also caused rapid scratching behavior, the frequency of which appeared to increase with the dose of the $A_3$ agonist. Since activation of $A_3$ receptors causes release of histamine in cultured mast cells, it was proposed that the scratching could be related to histamine. Coadministration of a histamine $H_1$-antagonist, cyproheptadine at 10 mg/kg i.p. eliminated this behavior, while at 1 mg/kg dose of cyproheptadine the effect was only partial.

Figure 3:
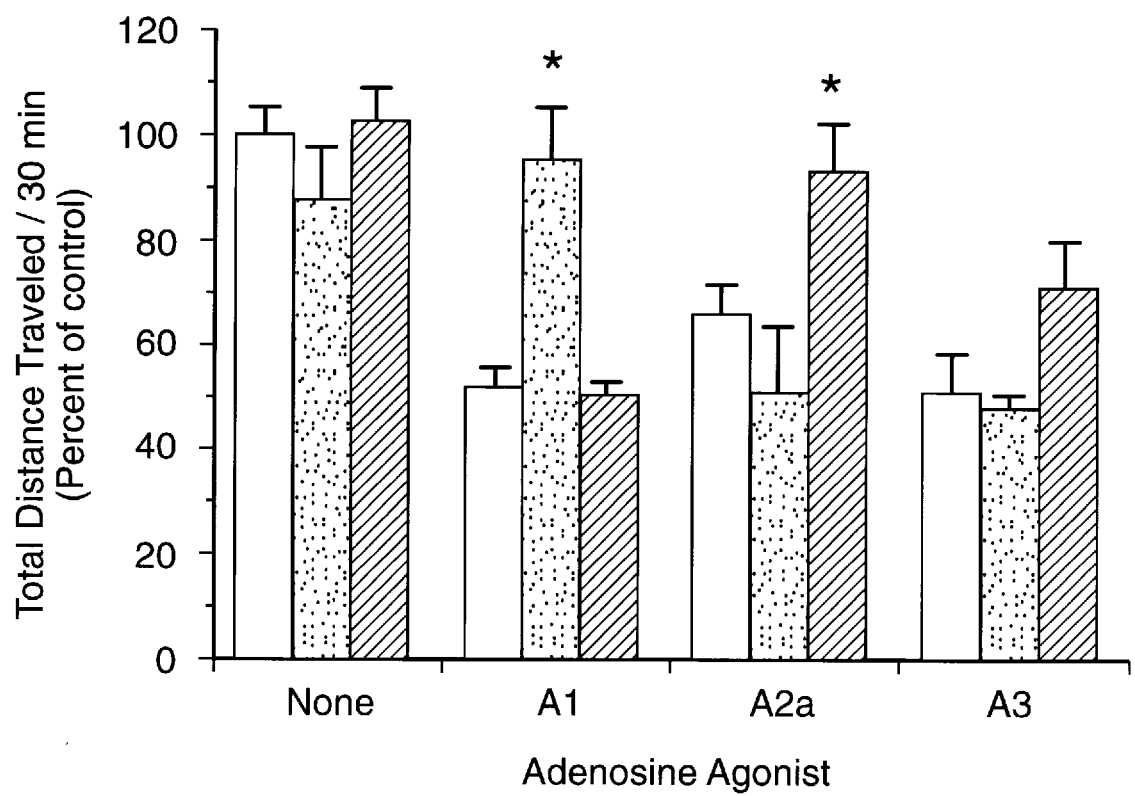
FIG. 3 is a bar graph of total distance traveled (cm/30 min) (percent of control) by mice versus type of adenosine receptor agonist.

FIG. 3 is a bar graph of total distance traveled/30 min (percent of control) versus adenosine receptor agonist, which shows the locomotor activity in mice following injection of an $A_1$- (CPA, 100 μg/kg), $A_{2a}$- (APEC, 16 μg/kg), or $A_3$-(3-IB-MECA, 100 μg/kg) selective agonist and the effects of coadministration of selective antagonists (n=6–19). Locomotor activity as a percent of control is shown for no antagonist (unshaded bars) or for coadministration of selective xanthine antagonists: CPX (shaded bars, $A_1$, 0.25 mg/kg) or CSC (hatched bars, $A_{2a}$, 1.0 mg/kg). The *p value<0.05 vs. adenosine agonist alone.

The highly $A_1$-selective antagonist CPX (0.25 mg/kg) completely reversed locomotor depression elicited by the potent $A_1$ agonist CPA (Research Biochemicals International, Natick, Mass.) at its determined $ED_{50}$ value of 100 μg/kg i.p (FIG. 3). CPX did not diminish the depressant effects of either the $A_{2a}$-selective agonist APEC or 3-IB-MECA at doses chosen to cause comparable ca. 50% reduction in locomotor activity.

The xanthine antagonist CSC is highly $A_{2a}$-selective in binding assays, functional adenylate cyclase assays, and in vivo with respect to locomotor activity. A dose of CSC of 1 mg/kg caused a small, statistically insignificant reversal of the 3-IB-MECA-mediated locomotor depression (FIG. 3). The same dose of CSC has been shown to cause a complete reversal of the behavioral depression elicited by APEC in the same experimental model.

The non-reversal of locomotor depression by the $A_1$- and $A_{2a}$-adenosine antagonists is consistent with in vitro observations with rat $A_3$-receptors, ie. the inability of xanthines to antagonize at this site (Zhou et al., PNAS USA, 89, 7432–7436 (1992); van Bergen et al., ACS 206th National Meeting, Chicago, Ill., August, 1993, Abstract MEDI217). Both CPX and CSC are known to act centrally (Jacobson et al., FEBS Letters, 323, 141–144 (1993)).

Example 38

This example demonstrates the cerebroprotective effects of chronic administration of an $A_3$-selective adenosine receptor agonist.

Female Mongolian gerbils were treated with 100 µg/kg IB-MECA (intraperitoneally) either 15 min prior to or for 10 days followed by one drug-free day prior to 10 min or 20 min forebrain arrest of cerebral circulation (ischemia). Ischemia was effected by bilateral occlusion of the carotid arteries. Control gerbils were injected with saline (0.15 ml, i.p. for 10 days). During postischemic recovery, the rate of cerebral blood flow return to pre-ischemia level, neurological status, and survival were monitored. After 7 days, all surviving animals were perfused with formaldehyde for further studies of morphology and histochemistry.

Figure 4:
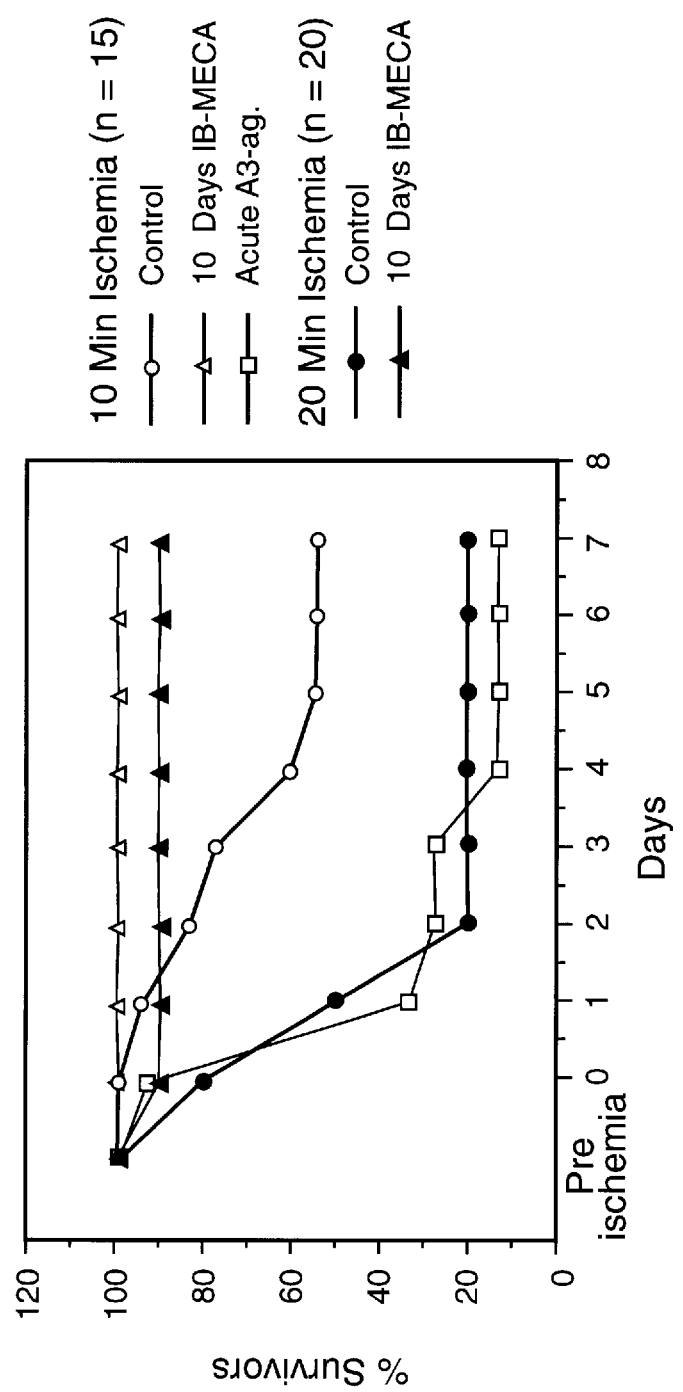
FIG. 4 is a graph of % survivors versus days following either 10 or 20 minute forebrain ischemia, with (acute or chronic) and without the administration of IB-MECA (0.1 mg/kg).

FIG. 4 is a graph of % survivors versus days after ischemia and sets forth the results of this experiment. As shown in FIG. 4, 60% of control gerbils survived for 7 days after 10 min ischemia (○, n=15). A 40% mortality was realized for control gerbils within the initial 36 hr post-ischemia. Ten percent of those gerbils treated with IB-MECA 15 min prior to 10 min ischemia survived for 7 days after 10 min ischemia (□, n=15). A 90% mortality was realized for the acutely treated gerbils within 12 hr post-ischemia. All those gerbils that had been chronically treated with IB-MECA prior to 10 min ischemia survived for 7 days after 10 min ischemia (Δ, n=15). Twenty percent of control gerbils survived for 7 days after 20 min ischemia (●, n=20), whereas 90% of those gerbils that had been chronically treated with IB-MECA prior to the 20 min ischemia survived for 7 days (▲, n=20). Of the control gerbils exposed to 10 min ischemia, 30% demonstrated seizures, 40% demonstrated mild forelimb paresis, 20% demonstrated ptosis, and 70% demonstrated hyperactivity. Of those gerbils treated with IB-MECA 15 min prior to 10 min ischemia, 60% demonstrated seizures, and 40% demonstrated irreversible coma. In contrast, only 40% of gerbils treated with IB-MECA for 10 days prior to 10 min ischemia demonstrated mild hyperactivity.

Figure 5:
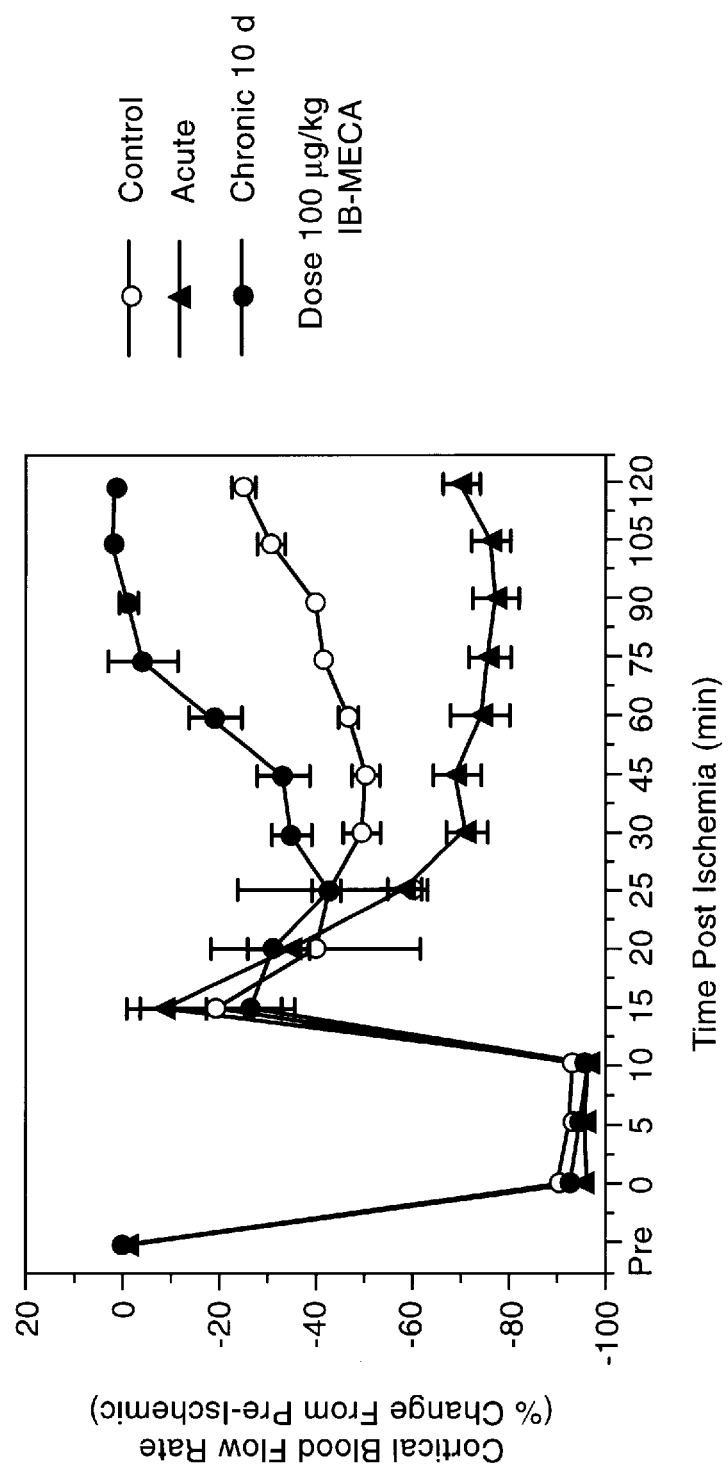
FIG. 5 is a graph of the rate of cortical blood flow (% change from pre-ischemia) versus time after 10 min cerebral ischemia (min) in the presence (acute or chronic) and absence of the $A_3$ adenosine receptor agonist IB-MECA.

FIG. 5 is a graph of the rate of cortical blood flow in the gerbils (% change from pre-ischemia) versus time after 10 min cerebral ischemia (min) in the presence and absence of the $A_3$ adenosine receptor agonist IB-MECA. As shown in FIG. 5, full recovery of post-ischemic blood flow was realized in control animals subjected to 10 min ischemia within 2.5 hr (○). One of those gerbils treated with IB-MECA 15 min prior to 10 min ischemia realized full recovery of blood flow in just over 3.5 hr (▲). In contrast, full recovery of blood flow was realized in gerbils treated with IB-MECA for 10 days prior to 10 min ischemia in about 90 min (●). No neurological side effects were observed in acutely and chronically treated gerbils that were not subjected to ischemia.

Figure 6:
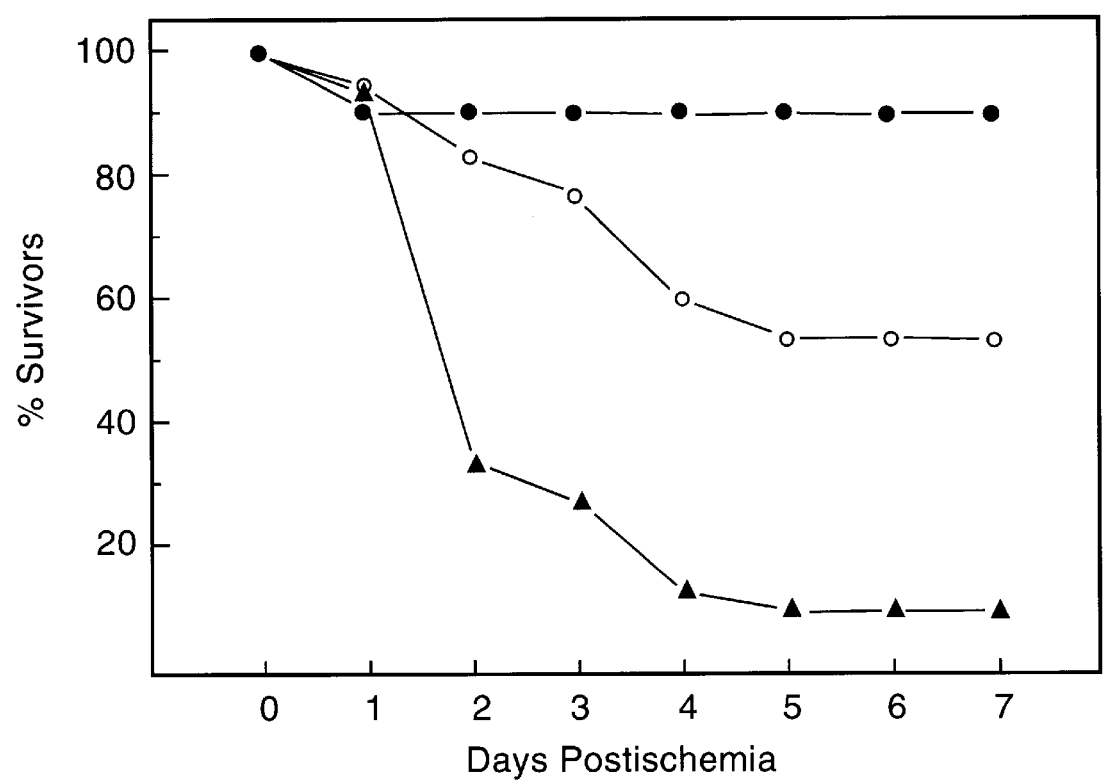
FIG. 6 is a bar graph of % survivors versus days post-ischemia.

FIG. 6 is a graph of % survivors versus days post-ischemia in a repeated experiment. FIG. 6 shows that the end-point mortality for control animals was 53% (○); the end-point mortality for acutely treated animals was 90% (▲, p<0.01). In contrast, 90% of the chronically treated animals survived (●, p<0.01).

Figure 7:
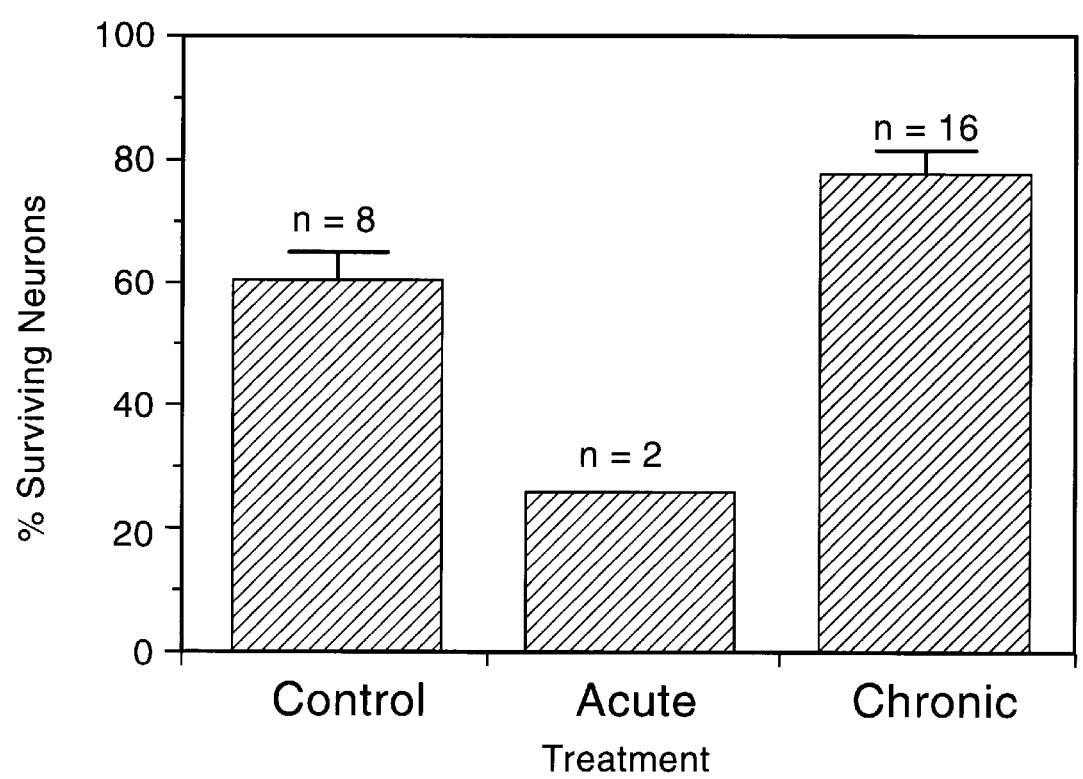
FIG. 7 is a bar graph of % surviving neurons in gerbil hippocampus following 10 min forebrain ischemia versus treatment with (acute or chronic) and without 100 μg/kg IB-MECA.

FIG. 7 is a bar graph of % surviving neurons in gerbil hippocampus following 10 min forebrain ischemia versus treatment method (control (○), acute (15 min, ▲) or chronic (●)) with 100 µg/kg IB-MECA, wherein n represents the number of hemispheres in each group (control: n=8; acute: n=2; chronic: n=16, where p<0.01 vs. control). Acute administration of the drug resulted in the impairment of postischemic cortical blood flow rate, increased mortality rate, and extensive neuronal destruction in the hippocampus. Chronic (10 days) treatment with IB-MECA prior to 10 min ischemia resulted in improved post-ischemic blood reflow, increased survival, and >80% survival of hippocampal neurons, whereas acute treatment with IB-MECA protected only about 30% of hippocampal neurons.

These data suggest that IP3 is a second messenger of the $A_3$ receptor and show that the $A_3$ receptor is desensitized by chronic administration of an $A_3$-selective adenosine receptor agonist, e.g., IB-MECA.

The above data show that chronic administration of an $A_3$-selective adenosine receptor agonist provides cerebroprotection from the effects of ischemia.

Example 39

This example demonstrates the cardiovascular effects of an $A_3$-selective adenosine receptor agonist.

Rats (each weighing 300–340 g) were lightly anesthetized using 1.5–2% halothane. They were monitored for heart rate with a tail sensor and blood pressure using the tail cuff method. Peripheral blood flow (scalp) was monitored using a Perimed laser Doppler blood flow apparatus, with a narrow diameter probe placed in contact with the shaved skin above the center of the cranium. A small amount of clear gel was applied to maintain uniform transmission of light. Body temperature was measured using a rectal probe. Respiratory rate was also recorded. Measurements were made at regular intervals: every 2 min for the first ten min period, and every five min thereafter, until 30 min, at which time a 30 min interval was used, until 90 min. Each drug group had 5–7 animals. Drugs were dissolved in a vehicle consisting of an 80:20 mixture of Alkamuls EL-620 and saline, pH 7.4. For a 0.1 mg/kg dose, a solution of 2.5 mg/ml in vehicle was prepared. When administered alone, the agonist was given at the beginning of the monitoring period. When coadministered with an antagonist, the antagonist was given at the beginning of the monitoring period, and the agonist was given after 10 min.

As a control experiment, the effects of mild halothane anesthesia on cardiovascular parameters were investigated and found to be minimal. A dose of 0.1 mg/kg, i.p., of IB-MECA was chosen, since at this dose locomotor depression in NIH mice, which are insensitive to either an $A_1$ or an $A_{2a}$ antagonist, is nearly maximal. The $A_3$ agonist administered alone caused a lowering of the blood pressure with little effect on heart rate. The effects of this agonist on blood flow and respiratory rates were not significant. In contrast, a potent and selective $A_1$ agonist, $N^6$-cyclopentyladenosine, at a dose of 0.1 mg/kg, i.p., caused an intense drop in both blood pressure (by 50%) and heart rate (by 20%) from their initial values. The hypotensive effect began to wane at approximately 20 min post-injection, but the bradycardiac effect of the $A_1$ agonist was prolonged during the entire monitoring period (90 min).

The effect of adenosine agonists on temperature was also measured (although the temperature of the animal was externally maintained by a heat source at 37° C.). IB-MECA maintained the original temperature until about 30 min post-injection, after which time the temperature dropped gradually by approximately 0.5° C. The hypothermic effects of $A_1$ agonists have been described. Busto et al., *J. Cereb. Blood Flow Metab.*, I, 729–738 (1987); Welsh et al., *J. Cereb. Blood Flow Metab.*, 10, 557–563 (1990); and Minamisawa et al., *Stroke*, 21, 758–764 (1990). The temperature of the animals dropped by approximately 1° C. over the course of the monitoring period.

A non-selective adenosine $A_1$ and $A_2$ antagonist, BW1433 (1,3-dipropyl-8-(4-carboxyvinylphenyl)xanthine, Dr. S. Daluge, Burroughs Wellcome, Research Triangle, N.C.), was used to eliminate any non-$A_3$ receptor component of the biological activity. This agent is particularly useful for probing the peripheral actions of adenosine (Jacobson et al., J. Med. Chem., 35, 4143–4149 (1992)), since it does not readily cross the blood-brain barrier. The dose of 4 mg/kg was selected based on previous experiments on reversing the antilipolytic effects of adenosine agonists. This antagonist, a 1,3-dipropylxanthine derivative, alone had biological effects in vivo. These included a prolonged rise in both blood pressure and heart rate (to>40% of initial values in each case, from 10–30 min post-injection). Blood flow and respiratory rates were increased by administration of the adenosine antagonist alone. The effect of BW1433 on body temperature was somewhat erratic, but there were no major changes.

When IB-MECA was injected 10 min after the adenosine antagonist BW1433, it still had an effect on blood pressure and heart rate, which were both restored to approximate control levels by the $A_3$ agonist IB-MECA. This is not interpreted as a simple antagonism, since the level of $A_1$ and $A_{2a}$ antagonism produced by the previously administered BW1433 is sufficient to block even high concentrations of agonists selective for those subtypes (Jacobson et al., J. Med. Chem., 35, 4143–4149 (1992)). Thus, if IB-MECA acted as an agonist at the $A_1$ and $A_{2a}$ receptors, its effect would also have been blocked. This suggests that $A_3$ receptors may be involved in maintaining cardiovascular homeostasis, in case of challenges to the system that would otherwise raise the blood pressure and heart rate. Similarly, the blood flow and respiratory rate were restored to their initial values by the $A_3$ agonist. The coadministration of BW1433 and IB-MECA had nearly no effect on body temperature.

IB-MECA was found to be 50-fold selective for $A_3$ receptors versus both $A_1$ and $A_{2a}$ receptors in rat brain. The above data suggest that it is also selective in vivo in a cardiovascular model. It is noteworthy that the Ki values for inhibition of radioligand binding by CPA ($N^6$-cyclopentyladenosine, Research Biochemicals International, Natick, Mass.) or IB-MECA at $A_1$ or $A_3$ receptors, respectively, are both about 1 nM. Furthermore, the doses of the two agents used in this Example were also identical (0.1 mg/kg).

IB-MECA acts in a manner that is highly atypical with respect to previously characterized adenosine agonists. The result is that most cardiovascular functions are maintained at near control values, even in the presence of a potent but non-selective (active only at $A_1$ and $A_2$, but not $A_3$ receptors) adenosine antagonist, BW1433. When the drug is administered alone, the curious result is that heart rate, respiration, and peripheral blood flow (scalp) is nearly constant, but there is a pronounced hypotensive effect that begins within 2 min post-injection and is prolonged throughout the entire 90 min monitoring period. This reasonably indicates that this $A_3$ agonist has a clinically useful half-life in vivo.

Example 40

This example demonstrates the anxiolytic effects of an $A_3$-selective adenosine receptor agonist.

C57BL/J mice were chronically treated by injection with 100 μg/kg IB-MECA, an $A_1$-selective adenosine receptor compound, or vehicle. Unlike control groups, IB-MECA chronically-treated animals demonstrated almost no injection-induced anxiety or stress behavioral responses as measured by aggressive and/or flight responses to handling.

Example 41

This example describes the synthesis of $N^6$-(3-iodobenzyl)-9-[β-D-ribofuranosyl]-adenine.

A mixture of 6-chloropurine riboside (Aldrich Chemical Co., 100 mg, 0.35 mmol), triethylamine (0.146 ml, 1.05 mmol), and 3-iodobenzylamine hydrochloride (103 mg, 0.38 mmol) in ethanol (2 ml) was heated for 18 h at 85° C. in a sealed bottle. After the reaction mixture was concentrated to dryness, the residue was purified on a silica gel column chromatography (CHCl$_3$—MeOH, 10:1) to yield $N^6$-(3-iodobenzyl)-9-[β-D-ribofuranosyl]-adenine (148 mg, 88%) as a colorless solid: m.p. 172° C.; $^1$H NMR (DMSO-d$_6$) d 3.54 (m, 1H, H-5'a), 3.67 (m, 1H, H-5'b), 3.96 (d, J=3.3 Hz, 1H, H-4'), 4.14 (m, 1H, H-3'), 4.60 (m, 1H, H-2'), 4.66 (br s, 2H, CH$_2$), 5.16 (d, J=4.4 Hz, 1H, exchangeable with D$_2$O, 3'-OH), 5.34 (br s, 1H, exchangeable with D$_2$O, 5'-OH), 5.43 (d, J=6.1 Hz, 1H, exchangeable with D$_2$O, 2'-OH), 5.89 (d, J=6.0 Hz, 1H, H-1'), 7.11 (pseudo t, J=8.0 and 7.8 Hz, 1H, H-5"), 7.36 (d, J=7.6 Hz, 1H, H-4" or -6"), 7.58 (d, J=7.8 Hz, 1H, H-4" or -6"), 7.72 (s, 1H, H-2"), 8.21 (s, 1H, H-2 or 8), 8.40 (s, 1H, H-2 or 8), 8.48 (br s, 1H, exchangeable with D$_2$O, N$^6$H,).

Example 42

The example describes the synthesis of 2-chloro-$N^6$-(3-iodobenzyl)-9-[β-D-ribofuranosyl]-adenine.

A mixture of 2-chloro-$N^6$-(3-iodobenzyl)-9-[2,3,5-tri-O-benzoyl-β-D-ribofuranosyl]-adenine (760 mg, 0.916 mmol) and NH$_3$/MeOH (15 ml) was stirred for 66.5 h at room temperature. After the reaction mixture was concentrated to dryness, the residue was purified on a silica gel column chromatography (CHCl$_3$—MeOH, 20:1) to yield 2-chloro-$N^6$-(3-iodobenzyl)-9-[β-D-ribofuranosyl]-adenine (445 mg, 94%) as a foam. $^1$H NMR (DMSO-d$_6$) d 3.55 (m, 1H, H-5'a), 3.65 (m, 1H, H-5'b), 3.94 (d, J=3.6 Hz, 1H, H-4'), 4.12 (m, 1H, H-3'), 4.51 (q, J=5.5 Hz, 1H, H-2'), 4.60 (br d, J=5.7 Hz, 2H, CH$_2$), 5.04 (pseudo t, J=5.7 and 5.5 Hz, 1H, exchangeable with D$_2$O, 5'-OH), 5.19 (d, J=4.9 Hz, 1H, exchangeable with D$_2$O, OH), 5.47 (d, J=6.0 Hz, 1H, exchangeable with D$_2$O, OH), 5.83 (d, J=5.5 Hz, 1H, H-1'), 7.13 (pseudo t, J=7.9 and 7.6 Hz, 1H, H-5"), 7.36 (d, J=7.5 Hz, 1H, H-4" or -6"), 7.60 (d, J=7.9 Hz, 1H, H-4" or -6"), 7.74 (s, 1H, H-2"), 8.43 (s, 1H, H-8), 8.94 (br t, J=6.0 Hz, 1H, exchangeable with D$_2$O, NH,).

Example 43

This example describes the synthesis of 2-amino-$N^6$-(3-iodobenzyl)-9-[β-D-ribofuranosyl]-adenine.

A mixture of 2-amino-6-chloropurine riboside (purchased from Aldrich Chemical Co., 80 mg, 0.26 mmol), 3-iodobenzylamine hydrochloride (71.5 mg, 0.265 mmol), and triethylamine (0.11 ml, 0.79 mmol) in ethanol (1.6 ml) was heated for 24 h at 80° C. After the reaction mixture was concentrated to dryness the residue was purified on a silica gel column chromatography (CHCl$_3$—MeOH, 20:1→10:1) to yield 2-amino-$N^6$-(3-iodobenzyl)-9-[β-D-ribofuranosyl]-adenine (99 mg, 75%) as a colorless solid: m.p. 152°–154° C.; $^1$H NMR (DMSO-d$_6$) d 3.52 (m, 1H, H-5'a), 3.63 (m, 1H, H-5'b), 3.89 (m, 1H, H-4'), 4.10 (m, 1H, H-3'), 4.50 (m, 1H, H-2'), 4.60 (br s, 2H, CH$_2$), 5.08 (d, J=4.6 Hz, 1H, exchangeable with D$_2$O, 3'-OH), 5.35 (m, 2H, exchangeable with D$_2$O, 5'- and 2'-OH), 5.73 (d, J=6.2 Hz, 1H, H-1'), 5.83 (br s, 2H, exchangeable with D$_2$O, NH$_2$), 7.11 (pseudo t, J=7.9 and 7.8 Hz, 1H, H-5"), 7.36 (d, J=7.8 Hz, 1H, H-4" or -6"), 7.58 (d, J=7.8 Hz, 1H, H-4" or -6"), 7.70 (s, 1H, H-2"), 7.94 (s, 1H, H-8).

Example 44

This example describes the synthesis of 2-chloro-$N^6$-(3-iodobenzyl)-9-[5-(methylamido)-β-D-ribofuranosyl]-adenine.

A mixture of 2-chloro-$N^6$-(3-iodobenzyl)-9-[5-(methylamido)-2,3-di-O-benzoyl-β-D-ribofuranosyl]-adenine (27 mg, 0.036 mmol) and $NH_3$/MeOH (15 ml) was stirred for 16 h at room temperature. After rotary evaporation of the volatiles, the residue was purified on a silica gel column chromatography ($CHCl_3$—MeOH, 20:1→10:1) to yield 2-chloro-$N^6$-(3-iodobenzyl)-9-[5-(methylamido)-β-D-ribofuranosyl]-adenine (13.4 mg, 68.7%) as a colorless solid: m.p. 206°–207° C.; $^1H$ NMR (DMSO-$d_6$) d 2.72 (d, J=4.3 Hz, 3H, —NH$CH_3$), 4.17 (br s, 1H, H-3'), 4.32 (s, 1H, H-4'), 5.55 (m, 1H, H-2'), 4.61 (br d, J=5.5 Hz, 2 Hz, $CH_2$), 5.56 (d, J=6.4 Hz, 1H, exchangeable with $D_2O$, 2'-OH), 5.72 (d, J=4.3 Hz, 1H, exchangeable with $D_2O$, 3'-OH), 5.92 (d, J=7.2 Hz, 1H, H-1'), 7.13 (pseudo t, J=7.9 and 7.6 Hz, 1H, H-5"), 7.36 (d, J=7.5 Hz, 1H, H-4" or -6"), 7.61 (d, J=7.8 Hz, 1H, H-4" or -6"), 7.75 (s, 1H, H-2"), 8.27 (br d, J=4.3 Hz, 1H, exchangeable with $D_2O$, NH), 8.49 (s, 1H, H-8), 9.02 (br t, J=6.2 and 5.7 Hz, 1H, exchangeable with $D_2O$, $N^6H$).

Example 45

This example describes the synthesis of $N^6$-(3-iodobenzyl)-2-methylamino-9-[5-(methylamido)-β-D-ribofuranosyl]-adenine.

A solution of 2-chloro-$N^6$-(3-iodobenzyl)-9-[5-(methylamido)-β-D-ribofuranosyl]-adenine (10 mg, 0.018 mmol) in 2N $CH_3NH_2$/THF (1.5 ml) was heated for 3 days at 90° C. After the reaction mixture was concentrated to dryness, the residue was purified on a preparative TLC ($CHCl_3$—MeOH, 10:1) to yield $N^6$-(3-iodobenzyl)-2-methylamino-9-[5-(methylamido)-β-D-ribofuranosyl]-adenine (7 mg, 70%) as a colorless solid: m.p. 190° C.; $^1H$ NMR (DMSO-$d_6$) d 2.66 (d, J=4.7 Hz, 3H, —NH$CH_3$), 2.76 (d, J=4.3 Hz, 3H, —NH$CH_3$), 4.18 (m, 1H, H-3'), 4.25 (s, 1H, H-4'), 4.57 (br s, 2H, $CH_2$), 4.69 (m, 1H, H-2'), 5.47 (d, J=6.5 Hz, 1H, exchangeable with $D_2O$, 2'-OH), 5.59 (d, J=4.6 Hz, 1H, exchangeable with $D_2O$, 3'-OH), 5.84 (d, J=7.2 Hz, 1H, H-1'), 6.28 (br d, J=4.4 Hz, exchangeable with $D_2O$, NH), 7.11 (pseudo t, J=8.0 and 7.8 Hz, 1H, H-5"), 7.38 (d, J=7.9 Hz, 1H, H-4" or -6"), 7.58 (d, J=7.9 Hz, 1H, H-4" or -6"), 7.70 (m, 1H, exchangeable with $D_2O$, NH), 7.76 (s, 1H, H-2"), 8.02 (s, 1H, H-8), 8.05 (br s, 1H, exchangeable with $D_2O$, NH). High resolution MS calcd. for $C_{19}H_{22}N_7O_4I_1$: 539.3362; Found: 540.0867.

Example 46

This example describes the synthesis of $N^6$-(3-iodobenzyl)-2-methylthio-9-[5-(methylamido)-β-D-ribofuranosyl]-adenine.

A solution of 2-chloro-$N^6$-(3-iodobenzyl)-9-[5-(methylamido)-β-D-ribofuranosyl]-adenine (15 mg, 0.029 mmol) and sodium thiomethoxide (4.0 mg, 0.057 mmol) in anhydrous ethylene glycol dimethyl ether (2 ml) was heated at 80° C., under nitrogen atmosphere, for 3 days. After cooling to room temperature, the reaction mixture was neutralized with glacial acetic acid and evaporated to dryness. The residue was purified on a preparative TLC ($CH_2Cl_2$—MeOH, 9.5:0.5) to yield $N^6$-(3-iodobenzyl)-2-methylthio-9-[5-(methylamido)-β-D-ribofuranosyl]-adenine (5.6 mg, 36.5%) as a yellow solid: m.p. 179° C.; $^1H$ NMR (DMSO-$d_6$) d 2.43 (s, 3H, —$SH_3$), 2.74 (d, J=4.3 Hz, 3H, —NH$CH_3$), 3.48 (br s, 2H, 2×OH), 4.19 (m, 1H, H-3'), 4.31 (s, 1H, H-4'), 4.62 (br s, 3H, $CH_2$ & H-2'), 5.87 (d, J=7.9 Hz, 1H, H-1'), 7.11 (pseudo t, J=8.0 and 7.8 Hz, 1H, H-5"), 7.90 (d, J=7.9 Hz, 1H, H-4" or -6"), 7.58 (d, J=7.9 Hz, 1H, H-4" or -6"), 7.76 (s, 1H, H-2"), 8.24 (br s, 1H, NH), 8.35 (s, 1H, h-8), 8.68 (br s, 1H, NH). High resolution mass (measured as ppm) in FAB mode, Calcd for $C_{19}H_{21}IN_6O_4S$: 557.0468; Found: 557.0482.

Example 47

This example describes the synthesis of 1-O-methyl 5-(t-butyldiphenylsilyl)-β-D-ribofuranoside.

To a mixture of methyl β-D-ribofuranoside (Sigma Chemical Co., 460 mg, 2.8 mmol) and anhydrous methylene chloride (20 ml) were added triethylamine (0.468 ml, 3.36 mmol), t-butyldiphenylchlorosilane (0.9 ml, 3.46 mmol), and DMAP (13.7 mg, 0.112 mmol) successively at room temperature. The reaction mixture was stirred for 18 h at room temperature under nitrogen. The reaction mixture was washed with water (20 ml), saturated ammonium chloride (20 ml), and brine (20 ml), dried over anhydrous $MgSO_4$, filtered, and concentrated to dryness. The residue was separated by silica gel column chromatography ($CHCl_3$—MeOH, 50:1) to yield 1-O-methyl 5-(t-butyldiphenylsilyl)-β-D-ribofuranoside [$R_f$=0.48 ($CHCl_3$—MeOH, 10:1), 618 mg, 54.8%] as a thick syrup. $^1H$ NMR (DMSO-$d_6$) d 0.96 (s, 9H, t-Bu), 3.22 (s, 3H, —$OCH_3$), 3.61 (dd, J=11.0 and 5.3 Hz, 1H), 3.74 (d, J=4.4 Hz, 1H), 3.81 (dd, J=11.0 and 2.7 Hz, 1H), 3.90 (m, 1H), 4.00 (m, 1H), 4.68 (s, 1H, H-1'), 4.84 (br s, 1H, exchangeable with $D_2O$, OH), 5.05 (br s, 1H, exchangeable with $D_2O$, OH), 7.45 and 7.67 (m, 10H, $Ph_2$). Anal. Calcd for $C_{22}H_{30}O_5Si$: C, 65.64; H, 7.51; Found: C, 65.73; H, 7.55.

Example 48

This example describes the synthesis of 1-O-methyl 5-(t-butyldiphenylsilyl)-2,3-dibenzoyl-β-D-ribofuranoside.

To a solution of 1-O-methyl 5-(t-butyldiphenylsilyl)-β-D-ribofuranoside (579 mg, 1.44 mmol) in methylene chloride-pyridine (4:1, 12.5 ml) was added dropwise benzoyl chloride (0.367 ml, 3.16 mmol) at 0° C. The reaction mixture was stirred for 2.5 h at 0° C. and for 14.5 h at room temperature. Ice was added to quench the reaction and the mixture was stirred for 1 h. Methylene chloride (100 ml) was added and two phases were separated. Organic layer was washed with water, saturated ammonium chloride, and brine, dried over anhydrous $MgSO_4$, filtered, and concentrated to dryness to yield 1-O-methyl 5-(t-butyldiphenylsilyl)-2,3-dibenzoyl-β-D-ribofuranoside in crude form, which was then purified by silica gel column chromatography (Hx-EtOAc, 5:1→1:1) to yield 1-O-methyl 5-(t-butyldiphenylsilyl)-2,3-dibenzoyl-β-D-ribofuranoside in more pure form [$R_f$=0.75 ($CHCl_3$—MeOH, 10:1), 869 mg, 99%] as a thick syrup. $^1H$ NMR ($CDCl_3$) d 1.05 (s, 9H, t-Bu), 3.42 (s, 3H, —$OCH_3$), 3.86 (dd, J=11.1 and 4.8 Hz, 1H, H-5a), 3.92 (dd, J=11.1 and 4.7 Hz, 1H, H-5b), 4.48 (dd, J=10.6 and 4.6 Hz, 1H), 5.15 (s, 1H), 5.63 (d, J=5.0 Hz, 1H), 5.82 (pseudo t, J=5.8 and 5.4 Hz, 1H), 7,29–8.18 (m, 20H, Ar). Anal. Calcd for $C_{36}H_{38}O_7Si_1$: C, 70.79; H, 6.27; Found: C, 71.01; H, 6.20.

Example 49

This example describes the synthesis of 1-O-methyl 2,3-dibenzoyl-β-D-ribofuranoside.

A solution of 1-O-methyl 5-(t-butyldiphenylsilyl)-2,3-dibenzoyl-β-D-ribofuranoside (849 mg, 1.39 mmol) and 1.0M tetrabutylammonium fluoride in THF (1.53 ml, 1.53 mmol) was stirred for 2 h at room temperature. After evaporation of the solvent, the residue was purified by silica gel column chromatography (Hx-EtOAc, 1:1) to yield 1-O-methyl 2,3-dibenzoyl-β-D-ribofuranoside [$R_f$=0.50 (Hx-EtOAc, 1:1), 461 mg, 89%] as thick syrup. $^1H$ NMR (DMSO-$d_6$) d 3.38 (s, 3H, —OCH$_3$), 3.62 (m, 2H, H-5), 4.37 (q, J=5.2 Hz, 1H, H-4), 5.02 (pseudo t, J=6.0 and 5.3 Hz, 1H, exchangeable with D$_2$O, 5-OH), 5.18 (s, 1H, H-1), 5.45 (m, 1H, H-2), 5.53 (t, J=5.2 Hz, 1H, H-3), 7.42–7.88 (m, 10H, Ar). Anal. Calcd for C$_{20}$H$_{20}$O$_7$: C, 64.51; H, 5.41; Found: C, 64.37; H, 5.47.

Example 50

This example describes the synthesis of 1-O-methyl-2,3-dibenzoyl-β-D-ribofuronic acid.

A mixture of 1-O-methyl 2,3-dibenzoyl-β-D-ribofuranoside (374.8 mg, 1.01 mmol), ruthenium (IV) oxide (10 mg), and sodium periodate (1161 mg, 5.43 mmol) in CHCl$_3$:CH$_3$CN:H$_2$O (2:2:3, 14 ml) was stirred vigorously for 2.5 h at room temperature. Chloroform (20 ml) was added and semisolid was removed by filtration. The two layers of filtrate were separated and aqueous layer was extracted with chloroform (2×40 ml). Combined organic layer and extracts were washed with brine, dried over anhydrous MgSO$_4$, filtered, and concentrated to dryness. After drying in vacuo overnight, 1-O-methyl-2,3-dibenzoyl-β-D-ribofuronic acid (340 mg, 89.5%) was obtained as a thick syrup. $^1$H NMR (CDCl$_3$) d 3.56 (s, 3H, —OCH$_3$), 4.90 (d, J=6.1 Hz, 1H, H-4), 5.25 (s, 1H, H-1), 5.66 (d, J=5.0 Hz, 1H, H-2), 6.00 (pseudo t, J=5.7 and 5.4 Hz, 1H, H-3), 7.32–7.99 (m, 10H, Ar). Anal. Calcd for C$_{20}$H$_{18}$O$_8$_0.63H$_2$O: C, 58.35; H, 4.71; Found: C, 58.36; H, 4.54.

Example 51

This example describes the synthesis of methyl 1-O-methyl-2,3-dibenzoyl-β-D-ribofuronate.

N-Ethyl-N'-diaminopropyl-carbodiimide (EDAC, 198 mg, 1.04 mmol) was added to a solution of 1-O-methyl-2,3-dibenzoyl-β-D-ribofuronic acid (0.16 g, 0.414 mmol) in MeOH (3 ml) and the reaction mixture was stirred for 3 h at room temperature. After the solvent was removed by rotary evaporation, the residue was dissolved in chloroform (50 ml), washed with water (30 ml) and brine (30 ml), dried over anhydrous MgSO$_4$, filtered, and concentrated to dryness. The residue was purified on a preparative TLC (Hx-EtOAc, 1:1) to yield methyl 1-O-methyl-2,3-dibenzoyl-β-D-ribofuronate [R$_f$=0.77 (Hx-EtOAc, 1:1), 120 mg, 72.3%] as a colorless solid: m.p. 92.2°–93.7° C.; $^1$H NMR (CDCl$_3$) d 3.52 (s, 3H, 1-OCH$_3$), 3.82 (2, 3H, 5-OCH$_3$), 4.84 (d, J=6.2 Hz, 1H, H-4), 5.21 (s, 1H, H-1), 5.62 (d, J=4.8 Hz, 1H, H-2), 6.01 (pseudo t, J=5.7 and 5.5 Hz, 1H, H-3), 7.32–7.99 (m, 10H, Ar). Anal. Calcd for C$_{21}$H$_{20}$O$_8$: C, 63.00; H, 5.03. Found: C, 63.05; H, 5.03.

Example 52

This example describes the synthesis of N-methyl 1-O-methyl-2,3-dibenzoyl-β-D-ribofuronamide.

A mixture of methyl 1-O-methyl-2,3-dibenzoyl-β-D-ribofuronate (35 mg, 0.087 mmol) and 2.0M methylamine in THF (3 ml) was heated for 15 h at 50° C. in a sealed tube. The volatiles were removed by evaporation and the residue was reacted with benzoyl chloride (0.15 ml, 1.29 mmol) in methylene chloride-pyridine (2:1, 6 ml) for 3 h at room temperature. After a workup similar to that for the compound of Example 48, the residue was separated by preparative TLC (Hx-EtOAc, 1:1) to yield N-methyl 1-O-methyl-2,3-dibenzoyl-β-D-ribofuronamide [R$_f$=0.28 (Hx-EtOAc, 1:1) or 0.77 (CHCl$_3$—MeOH, 10:1), 25 mg, 72%] as a syrup. $^1$H NMR (CDCl$_3$) d 2.92 (d, J=5.0 Hz, 3H, —NHCH$_3$), 3.58 (s, 3H, 1-OCH$_3$), 4.82 (d, J=5.5 Hz, 1H, H-4), 5.24 (s, 1H, H-1), 5.60 (m, 1H, H-2), 5.87 (t, J=5.1 Hz, 1H, H-3), 6.68 (br m, 1H, —NH), 7.33–7.99 (m, 10H, Ar). Anal. Calcd for C$_{21}$H$_{21}$NO$_7$_0.5H$_2$O: C, 61.76; H, 5.43; N, 3.43; Found: C, 61.76; H, 5.24; N, 3.41.

Example 53

This example describes the synthesis of N-methyl 1-O-acetyl-2,3-dibenzoyl-α-D-ribofuronamide and N-methyl 1-O-acetyl-2,3-dibenzoyl-α-D-ribofuronamide.

To a solution of N-methyl 1-O-methyl-2,3-dibenzoyl-β-D-ribofuronamide (1.533 g, 3.84 mmol) and acetic anhydride (3.8 ml, 40.3 mmol) in glacial acetic acid (19 ml) was added dropwise c-H$_2$SO$_4$ (1.125 ml, 21.1 mmol) and the reaction mixture was stirred for 15 h at room temperature. After water (30 ml) was added slowly, the mixture was extracted with methylene chloride (150 ml×3), and the organic layer was washed with saturated NaHCO$_3$ and brine, dried over anhydrous MgSO$_4$, filtered, and concentrated to dryness. The residue was purified on a silica gel column chromatography (CHCl$_3$_MeOH, 20:1) to yield a mixture of (a) N-methyl 1-O-acetyl-2,3-dibenzoyl-α-D-ribofuronamide and (b) N-methyl 1-O-acetyl-2,3-dibenzoyl-β-D-ribofuronamide [R$_f$=0.71 and 0.76 (CHCl$_3$—MeOH, 20:1), respectively, 0.55 g, 33.5%] as a foam.

Analytical samples were separated on a preparative TLC (CHCl$_3$—MeOH, 20:1). $^1$H NMR (CDCl$_3$). Compound A: d 2.10 (s, 3H, —OAc), 2.91 (d, J=4.9 Hz, 3H, —NHCH$_3$), 4.96 (s, 1H, H-4), 5.45 (pseudo t, J=5.5 and 5.0 Hz, 1H, H-2), 6.08 (d, J=5.9 Hz, 1H, H-3), 6.71 (d, J=4.7 Hz, 1H, H-1), 6.72 (br s, 1H, —NH), 7.28 (pseudo t, J=7.8 and 7.7 Hz, 2H, Ar), 7.48 (q, J=7.8 Hz, 3H, Ar), 7.62 (pseudo t, J=7.7 and 6.9 Hz, 1H, Ar), 7.79 (d, J=7.4 Hz, 2H, Ar), 8.13 (d, J=7.8 Hz, 2H, Ar). Compound B: d 2.17 (s, 3H, —OAc), 2.90 (d, J=4.9 Hz, 3H, —NHCH$_3$), 4.89 (d, J=6.2 Hz, 1H, H-4), 5.73 (d J=4.9 Hz, 1H, H-2), 5.96 (t, J=5.9 Hz, 1H, H-3), 6.43 (s, 1H, H-1), 6.50 (br s, 1H, —NH), 7.37 (pseudo t, J=7.8 and 7.6 Hz, 4H, Ar), 7.48–7.58 (m, 2H, Ar), 7.93 (d, J=8.1 Hz, 2H, Ar), 7.98 (d, J=7.3 Hz, 2H, Ar).

Anal. Calcd for C$_{22}$H$_{21}$N$_1$O$_8$_0.3H$_2$O: C, 61.05; H, 5.03; N, 3.24; Found: C, 61.09; H, 5.05; N, 3.63.

Example 54

This example describes the synthesis of 2-chloro-N$^6$-(3-iodobenzyl)adenine.

A solution of 2,6-dichloropurine (Aldrich Chemical Co., 1 g, 5.3 mmol), 3-iodobenzylamine hydrochloride (1.7 g, 5.8 mmol), and triethylamine (2.2 ml, 15.35 mmol) in ethanol (10 ml) was stirred for 5 days at room temperature. The colorless solid formed was collected by suction, washed with small amount of cold ethanol, and dried to yield 2-chloro-N$^6$-(3-iodobenzyl)adenine (1.16 g, 60%): m.p. 222°–224° C.; mass (EI) 385: $^1$H NMR (DMSO-$d_6$ d 4.59 (br s, 2H, —CH$_2$), 7.13 (pseudo t, J=8.2 and 7.5 Hz, 1H, Bn), 7.36 (d, J=7.5 Hz, 1H, Bn), 7.61 (d, J=7.5 Hz, 1H, Bn), 7.74 (s, 1H, Bn), 8.14 (s, 1H, H-8), 8.76 (br s, 1H, exchangeable with D$_2$O, NH), 13.14 (br s, 1H, exchangeable with D$_2$O, NH). UV (MeOH) 1$_{max}$ 281.7, 257.5, 232.5 nm.

Example 55

This example describes the synthesis of 2-chloro-N$^6$-(3-iodobenzyl)-9-[5-(methylamido)-2,3-di-O-benzoyl-β-D-ribofuranosyl]-adenine.

A mixture of 2-chloro-N$^6$-(3-iodobenzyl)adenine (165 mg, 0.43 mmol), ammonium sulfate (catalytic amount), and HMDS (15 ml) was refluxed for 4 h under nitrogen to provide the silylated derivative. The clear solution was concentrated to dryness in vacuo with exclusion of moisture and the residue was dissolved in dry dichloroethane (6 ml). A solution of N-methyl 1-O-acetyl-2,3-dibenzoyl-α-D-ribofuronamide and N-methyl 1-O-acetyl-2,3-dibenzoyl-β-D-ribofuronamide (141 mg, 0.33 mmol) in dry dichloroethane (6 ml) and TMSOTf (83 ml, 0.43 mmol) was added, and the reaction mixture was stirred for 0.5 h at room temperature and refluxed for 62 h under nitrogen. Saturated NaHCO$_3$ (10 ml) was added, and the mixture was stirred for 15 min. Two layers were separated and the aqueous layer was extracted with methylene chloride (50 ml×3), washed with brine, dried over anhydrous MgSO$_4$, filtered, and concentrated to dryness. The residue was purified on a preparative TLC (CHCl$_3$—MeOH, 20:1) to yield 2-chloro-N$^6$-(3-iodobenzyl)-9-[5-(methylamido)-2,3-di-O-benzoyl-β-D-ribofuranosyl]-adenine [R$_f$=0.58 (CHCl$_3$—MeOH, 20:1), 83 mg, 33%] as a foam. $^1$H NMR (CDCl$_3$) d 3.10 (d, J=4.6 Hz, 3H, —NHCH$_3$), 4.79 (br s, 2H, CH$_2$), 4.97 (s, 1H, H-4'), 6.08 (m, 1H, H-3'), 6.15–6.25 (m, 3H, H-2', 1', NH), 7.06–8.06 (m, 15H, Ar), 8.52 (br s, 1H, NH).

Example 56

This example describes the synthesis of 2-chloro-N$^6$-(3-iodobenzyl)-9-[2,3,5-tri-O-benzoyl-β-D-ribofuranosyl]-adenine.

A mixture of 2-chloro-N$^6$-(3-iodobenzyl)adenine (0.84 g, 2.18 mmol), ammonium sulfate (catalytic amount), and HMDS (20 ml) was refluxed for 5 h under nitrogen to provide the silylated derivative. The clear solution was concentrated to dryness in vacuo with exclusion of moisture and the residue was dissolved in dry dichloroethane (6 ml). A solution of 1-O-acetyl-2,3,5-tri-O-benzoyl-β-D-ribofuranoside (Janssen Chimica Chemical Co., 1 g, 1.98 mmol) in dry dichloroethane (12 ml) and TMSOTf (0.42 ml, 2.18 mmol) was added, and the reaction mixture was stirred for 20 min at room temperature and refluxed for 14 h under nitrogen. After a workup similar to that for the compound of Example 55, the residue was purified on a silica gel column chromatography (Hx-EtOAc, 2:1) to yield 2-chloro-N$^6$-(3-iodobenzyl)-9-[2,3,5-tri-O-benzoyl-β-D-ribofuranosyl]-adenine [R$_f$=0.11 (Hx-EtOAc, 3:1), 1.495 g, 91%] as a colorless foam. $^1$H NMR (CDCl$_3$) d 4.69–4.92 (m, 5H, CH$_2$, H-4', H-5'), 6.15 (m, 3H, H-2', H-3', NH), 6.45 (d, J=4.3 Hz, 1H, H-1'), 7.07 (pseudo t, 1H, Bn), 7.31–8.10 (m, 20H, Ar).

Example 57

This example describes a radioligand binding assay used to study the structure activity relationship (SAR) at the A$_3$ receptor in a manner similar to that set forth in Example 35.

Adenosine analogues were tested in radioligand binding assays (Olah et al., Mol. Pharmacol., 45, 978–982 (1994); Schwabe et al., Naunyn-Schmiedeberg's Arch. Pharmacol., 313, 179–187 (1980); Jarvis et al., J. Pharmacol. Exp. Therap., 251, 888–893 (1989)) for affinity at rat brain A$_1$, A$_{2a}$, and A$_3$ adenosine receptors. The compounds were assayed as follows: at A$_1$ receptors in rat cortical membranes using [$^3$H]N$^6$-R-phenylisopropyladenosine (Schwabe et al., supra); at A$_{2a}$ receptors in rat striatal membranes using [$^3$H]CGS 21680 (Jarvis et al., supra); at A$_3$ receptors using [$^{125}$I]AB-MECA (Olah et al., supra) in membranes of CHO cells stably transfected with cDNA for rat brain A$_3$ receptors (Zhou et al., Proc. Natl. Acad. Sci. U.S.A., 89, 7432–7436 (1992)).

The preparation of rat brain membranes and CHO cell membranes was carried out essentially as described in van Galen et al., Mol. Pharmacol., 45, 1101–1111 (1994), van Bergen et al., ACS 206th National Meeting, Chicago, Ill., Abstract MEDI217 (August 1993), Gallo-Rodriguez et al.,J. Med. Chem., 37, 636–646 (1994), Olah et al., Mol. Pharmacol., 45, 978–982 (1994). Adenosine deaminase (ADA) was from Boehringer Mannheim (Indianapolis, Ind.). [$^3$H]R-PIA was from Amersham (Arlington Heights, Ill.), and [$^3$H]CGS 21680 was from DuPont NEN (Boston, Mass.). [$^{125}$I]AB-MECA was prepared as described by Olah et al., supra.

Binding of [$^{125}$I]AB-MECA to CHO cells stably transfected with the A$_3$ receptor clone was performed essentially as described in Gallo-Rodriguez et al., supra, and Olah et al., supra. Assays were performed in 50 mM Tris/10 mM MgCl$_2$/1 mM EDTA buffer (adjusted to pH 8.26 at 5° C.) in glass tubes and contained 100 μl of the membrane suspension, 50 μl of [$^{125}$I]AB-MECA (final concentration 0.3 nM), and 50 μl of inhibitor. Inhibitors were routinely dissolved in DMSO and were then diluted with buffer. The final DMSO concentrations never exceeded 1%; this concentration did not influence [$^{125}$I]AB-MECA binding. Incubations were carried out in duplicate for 1 hour at 37° C., and were terminated by rapid filtration over Whatman GF/B filters, using a Brandell cell harvester (Brandell, Gaithersburg, Md.). Tubes were washed three times with 3 mL of buffer. Radioactivity was determined in a Beckman gamma 5500B g-counter. Non-specific binding was determined in the presence of 200 μM NECA. K$_i$-values were calculated according to Cheng-Prusoff (Cheng et al., supra), assuming a K$_d$ for [$^{125}$I]AB-MECA of 1.48 nM (Fozard et al., Br. J. Pharmacol., 109, 3–5 (1993).

Binding of [$^3$H]PIA to A$_1$ receptors from rat cortical membranes and of [$^3$H]CGS 21680 to A$_2$ receptors from rat striatal membranes was performed as described previously (Gallo-Rodriguez et al., supra).

Competition for binding of [$^3$H]NBTI was carried out by a modification of the procedure of Marangos et al., J. Neurochem., 39, 184–191 (1982). Rat striatal membranes, prepared as above, were subjected to incubation for 30 min at 23° C. with 0.3 nM [$^3$H]NBTI and varying concentrations of the nucleoside derivative in Tris buffer, pH 7.4 in a total of 0.5 ml. For non-specific binding, 5 μM S-(p-nitrobenzyl)-6-thioguansine (Sigma, St. Louis, Mo.) was added, and specific binding was 95% of total. A K$_d$ value of 0.15 nM was used in the calculation of K$_i$ values (Marangos et al., supra). Specific binding was 95% of total.

Adenylate cyclase was assayed in membranes from CHO cells stably expressing the rat A$_3$ receptor, prepared as above, using the previously reported method described in van Galen et al., Mol. Pharmacol., 45, 1101–1111 (1994), van Bergen et al., ACS 206th National Meeting, Chicago, Ill., Abstract MEDI217 (August 1993). The method involved the addition of [a-$^{32}$P]ATP to membranes in the presence of forskolin to stimulate adenylate cyclase and papaverine as a phosphodiesterase inhibitor. The reaction was terminated by addition of a stop solution containing 20,000 cpm/ml [$^3$H]cyclic AMP. The total radiolabeled cyclic AMP was isolated on columns of Dowex 50 ion exchange resin and alumina. Maximal inhibition of adenylate cyclase activity corresponded to ~40% of total activity under conditions of stimulation (typically by 6–8 fold) in the presence of 1 μM forskolin.

TABLE 2

Affinities of 5'-uronamide derivatives in radioligand binding assays at rat brain $A_1$, $A_2$, and $A_3$ receptors[a–c]

| Compound | $K_i(A_1)$ | $K_i(A_2)$ | $K_i(A_3)$ | $A_1/A_3$ | $A_2/A_3$ |
|---|---|---|---|---|---|
| IB-MECA[d] | 54 | 56 | 1.1 | 49 | 51 |
| [$^{125}$I]AB-MECA[d] | 18 | 197 | 1.3 | 14 | 160 |
| APNEA | 14[f] | 172 ± 50 | 116 ± 18 | 0.16 | 1.5 |
| [$^{125}$I]APNEA | 2.1[f] | — | 15.5[g] | 0.14 | — |
| CGS 21680[e] | 2600 | 15 | 584 | 4.4 | 0.026 |
| APEC | 400 | 5.7 | 50 ± 24 | 8 | 0.11 |
| 2 chloro-adenosine[e] | 9.3 | 63 | 1890 | 0.0049 | 0.033 |
| $N^6$-cyclopentyladenosine[d] | 0.59 | 462 | 240 | 0.0025 | 1.9 |
| 2-chloro-$N^6$-cyclopentyladenosine[d] | 0.6 | 950 | 237 | 0.0025 | 4.0 |
| $N^6$-(3-iodobenzyl)-adenosine [Example 41] | 20.0 ± 8.5 | 17.5 ± 0.5 | 9.5 ± 1.4 | 2.1 | 1.8 |
| 2-chloro-$N^6$-(3-iodobenzyl)-adenosine [Example 42] | 18.5 ± 4.7 | 38.5 ± 2.0 | 1.41 ± 0.17 | 13 | 27 |
| 2-amino-$N^6$-(3-iodobenzyl)-adenosine [Example 43] | 63.8 ± 15.1 | 117 ± 15 | 181 ± 30 | 0.35 | 0.65 |
| 2-chloro-$N^6$-(3-iodobenzyl)-9-[5-(methylamido)-β-D-ribofuranosyl]-adenine [Example 44] | 820 ± 570 | 470 ± 365 | 0.23 ± 0.11 | 3600 | 2000 |
| $N^6$-(3-iodobenzyl)-2-methylamino-9-[5-(methylamido)-β-D-ribofuranosyl]-adenine [Example 45] | 4890 ± 2580 | 4120 ± 210 | 3.12 ± 0.64 | 1600 | 1300 |
| $N^6$-(3-iodobenzyl)-2-methylthio-9-[5-(methylamido)-β-D-ribofuranosyl]-adenine [Example 46] | 2140 ± 100 | 3210 ± 1360 | 2.30 ± 0.96 | 930 | 1400 |

[a]Displacement of specific [$^3$H]PIA binding, unless noted, in rat brain membranes, expressed as $K_i$ ± S.E.M. in nM (n = 3–6).
[b]Displacement of specific [$^3$H]CGS 21680 binding, unless noted, in rat striatal membranes, expressed as $K_i$ ± S.E.M. in nM (n = 3–6).
[c]Displacement of specific binding of [$^{125}$I]4-amino-3-iodobenzyladenosine-5'-N-methyluronamide from membranes of CHO cells stably transfected with the rat $A_3$-cDNA, expressed as $K_i$ ± S.E.M. in nM (n = 3–7).
[d]Values are from Gallo-Rodriguez et al., J. Med. Chem., 37, 636–646 (1994).
[e]Values are from van Galen et al., Mol. Pharmacol., 45, 1101–1111 (1994). $A_3$ affinity measured by displacement of specific binding of [$^{125}$I]APNEA in membranes of CHO cells stably transfected with the rat $A_3$-cDNA. $K_i$ values at $A_1$ receptors are vs. specific binding of [$^3$H]$N^6$-cyclohexyladenosine or [$^3$H]R-PIA. $K_i$ values at $A_{2a}$ receptors are vs. specific binding of [$^3$H]NECA in the presence of 50 nM CPA or vs. specific binding of [$^3$H]CGS 21680 in rat striatal membranes.
[f]$IC_{50}$ values (nM) vs. displacement of specific binding of [$^{125}$I]APNEA in rat brain membranes.
[g]$K_d$ value (nM) from saturation of binding of [$^{125}$I]APNEA in membranes of CHO cells stably transfected with the rat $A_3$-cDNA.

As is apparent from the results set forth in Table 2, although the [$^{125}$I]AB-MECA is of nanomolar potency at $A_3$ receptors and more potent than [$^{125}$I]APNEA, it is not very selective for $A_3$ vs. $A_1$ or $A_{2a}$ receptors. The presence of the 4-amino group of [$^{125}$I]AB-MECA decreases selectivity in comparison to moderately $A_3$ selective agonist IB-MECA. The $N^6$-derivative of adenosine, APNEA, has been used recently in pharmacological studies (Fozard et al., supra) to stimulate $A_3$ receptors, although it is actually $A_1$-selective. Until present, no mono-substituted adenosine derivatives have been reported to be selective for $A_3$ receptors. Among high affinity 5',$N^6$-disubstituted adenosine derivatives, only 50 to 70-fold selectivity for $A_3$ vs. $A_1$ receptors has been achieved.

Substitution at the 2-position is often associated with selectivity of adenosine agonists for $A_{2a}$ vs. $A_1$ receptors. For example, CGS 21680 and APEC, both having sterically bulky 2-substituents, were reported to be highly selective for $A_{2a}$ receptors in models of adenylate cyclase (Hide et al., Mol Pharmacol., 41, 352–359 (1992)). APEC was more potent at all three adenosine receptor subtypes than CGS 21680, and both compounds displayed a potency order of $A_{2a}>A_3>A_1$, consistent with the findings of van Galen et al., supra, that 2-substitution of adenosine is well-tolerated in binding to $A_3$ receptors. Among mono-substituted derivatives of adenosine, 2-phenylamino- and 2-chloro-adenosine have $K_i$ values for inhibition of binding of [$^{125}$I]APNEA ($N^6$-[2-(4-aminophenyl)ethyl]-adenosine) at rat $A_3$ receptors of 4.4 and 1.9 μM, respectively. Substitution at the 2-position is also compatible with $N^6$-substitution for affinity at $A_3$ receptors. For example, 2-chloro-$N^6$-cyclopentyladenosine is nearly identical in its receptor binding profile to $N^6$-cyclopentyladenosine.

$N^6$-(3-Iodobenzyl)-adenosine was 2-fold selective for $A_3$ vs. $A_1$ or $A_{2a}$ receptors, making it is the first mono-substituted adenosine analogue with any selectivity for $A_3$-receptors. 2-Chloro-$N^6$-(3-iodobenzyl)-adenosine was 7-fold more potent than $N^6$-(3-Iodobenzyl)-adenosine at $A_3$ receptors and of moderate selectivity. 2-Amino substitution of adenosine analogues is also compatible with $N^6$-substitution in $A_3$ receptor binding, but is not as favorable as 2-chloro for potency and selectivity. For example, 2-amino-$N^6$-(3-iodobenzyl)adenosine was less potent than the 2-H analogue, $N^6$-(3-Iodobenzyl)-adenosine, by factors of: 3.2 ($A_1$ receptors); 6.7 ($A_{2a}$ receptors); and 19 ($A_3$ receptors).

The combination of 2-substitution with the substituent groups of IB-MECA resulted in very high potency and selectivity for $A_3$ receptors. The $A_3$ affinity of the 2-chloro analogue, 2-chloro-$N^6$-(3-iodobenzyl)-adenosine-5'-N-methyluronamide, was 5-fold greater than for IB-MECA. The affinity at $A_1$ and $A_{2a}$ receptors was diminished relative to IB-MECA by 15- and 9-fold, respectively. Thus, selectivities of approximately 3600-fold vs. $A_1$ receptors and 2000-fold vs. $A_{2a}$ receptors were achieved. 2-Methylamino-$N^6$-(3-iodobenzyl)adenosine-5'-N-methyluronamide was less potent ($K_i$ value 3 nM), but still highly selective for $A_3$ receptors. 2-Methylthio-$N^6$-(3-iodobenzyl)adenosine-5'-N-methyluronamide was also highly selective for $A_3$ receptors.

Example 58

The selectivity of several of the adenosine derivatives vs. a nucleoside transporter previously characterized in brain, namely [$^3$H]$N^6$-(4-nitrobenzyl)thioinosine (NBTI), was probed. These experiments were carried out because of the structural similarity of the present adenosine derivatives to various 6-benzylethers or thioether derivatives of purine ribosides, known to be high affinity antagonists of adenosine uptake via this transporter. The obtained results are reflected in Table 3 below.

TABLE 3

Inhibition of specific binding of NBTI binding at adenosine uptake sites in rat brain membranes and the selectivity ratio for affinity at cloned rat $A_3$ receptors

| Compound | $K_i$ (NBTI)[a] | Ratio of $K_i$ (NBTI)/ $K_i$ ([$^{125}$I] AB-MECA |
|---|---|---|
| $N^6$-benzyl-adenosine | 203 ± 93 | 1.69 |
| IB-MECA | 28,200 ± 10,700 | 22,000 |
| 2-chloro-$N^6$-(3-iodobenzyl)-9-[5-(methylamido)-β-D-ribofuranosyl]-adenine [Example 44] | 15,200 ± 5,200 | 66,000 |
| $N^6$-(3-iodobenzyl)-2-methylthio-9-[5-(methylamido)-β-D-ribofuranosyl]-adenine [Example 46] | 49,500 ± 633 | 22,000 |

[a]$K_i$ values are expressed in nM as $K_i$ ± S.E.M. for 3–4 determinations (each done in triplicate). Rat striatal membranes were incubated for 30 min at 23° C. with 0.3 nM [$^3$H]NBTI and varying concentrations of the nucleoside derivative in Tris buffer, pH 7.4, in a total of 0.5 ml. Nonspecific binding was determined in the presence of 5 μM S-(p-nitrobenzyl)-6-thioguansine.

As is apparent from the resulting data set out in Table 3, the simple $N^6$-benzyl derivative of adenosine was found not to be selective for the receptors vs. the adenosine transporter. In contrast, 2-chloro-$N^6$-(3-iodobenzyl)-adenosine-5'-N-methyluronamide was 66,000-fold selective for $A_3$ receptors vs. the $Na^+$-independent adenosine transporter, as indicated in displacement of [$^3$H]$N^6$-(4-nitrobenzyl)thioinosine binding in rat brain membranes. Thus, in this series of 2,6,5'-trisubstituted adenosine derivatives there was a high degree of selectivity for $A_3$ receptors vs. potential antagonism of adenosine uptake.

The agonist properties of the selective ligands were also examined. In a functional assay using membranes from CHO cells stably transfected with rat $A_3$ receptors, 2-chloro-$N^6$-(3-iodobenzyl)-adenosine-5'-N-methyluronamide inhibited adenylate cyclase with an $IC_{50}$ of $10^{-8}$M. It was a full agonist.

Example 59

This example describes the synthesis of 8-methoxytheophylline-7-β-D-ribofuranoside.

A mixture of 8-chlorotheophylline (276 mg, 1.29 mmol) and N,O-bis(trimethylsilyl)acetamide (1 ml) in dry dichloromethane (6 ml) was stirred for 40 min at room temperature under nitrogen. Solvent was removed by rotary evaporation in vacuo with exclusion of moisture. The residue was suspended in dry acetonitrile (9 ml). 1-O-Acetyl-2,3,5-tri-O-benzoyl-β-D-ribofuranoside (500 mg, 1.0 mmol), potassium nonaflate (1.0 g, 2.96 mmol), and trichlorosilane (0.38 ml, 2.8 mmol) were added and the reaction mixture was refluxed for 4 h under nitrogen. Aqueous saturated sodium bicarbonate (30 ml) and dichloromethane (30 ml) were added. After stirring for 15 min, two layers were separated and aqueous layer was extracted with dichloromethane (3×30 ml). The combined organic layer and extracts were washed with brine, dried over anhydrous $MgSO_4$, filtered, and concentrated to dryness. The residue was crystalized from ethyl acetate-hexanes to yield the compound depicted as intermediate h in Reaction Scheme J above (424 mg). Purification of the filtrate on silica gel column chromatography (hexanes-ethyl acetate, 3:1→1:1) yielded additional intermediate h (59.1 mg, 76%) as a solid: m.p. shrinks at 179°–180° C. and decomposed at 258° C. $^1$H NMR ($CDCl_3$) d 3.38 (s, 3H, N—C$\underline{H}_3$), 3.57 (s, 3H, N—C$\underline{H}_3$), 4.72–4.77 (m, 2H), 4.90 (m, 1H), 6.17 (m, 2H, H-5'), 6.36 (d, J=4.6 Hz, 1H, H-1'), 7.25–8.11 (m, 15H, Ar).

A mixture of the compound depicted as intermediate h in Reaction Scheme J above (212 mg, 0.33 mmol) and $NH_3$/MeOH (20 ml) was stirred for 4 days at room temperature. After the reaction mixture was concentrated to dryness, the residue was purified on silica gel column chromatography ($CHCl_3$—MeOH, 20:1) to yield 8-methoxytheophylline-7-β-D-ribofuranoside (33 mg, 29%) as a soft solid. $^1$H NMR (DMSO-$d_6$) d 3.21 (s, 3H, $NCH_3$), 3.43 (s, 3H, $NCH_3$), 3.45 (m, 1H, H-5'a), 3.60 (dd, J=11.7 and 5.2 Hz, 1H, H-5'b), 3.79 (m, 1H), 4.02 (m, 1H), 4.11 (s, 4H, $OCH_3$), 4.59 (t, J=5.9 Hz, 1H), 4.78 (t, J=5.4 Hz, 1H, exchangeable with $D_2O$, 5'-OH), 5.08 (d, J=4.8 Hz, 1H, exchangeable with $D_2O$, OH), 5.25 (d, J=6.4 Hz, 1H, exchangeable with $D_2O$, OH), 5.89 (d, J=6.5 Hz, 1H, H-1').

Example 60

This example describes the synthesis of 1,3-di-n-butylxanthine-7-β-D-ribofuranoside.

A mixture of 1,3-di-n-butylxanthine (3 g, 11.35 mmol), ammonium sulfate (5 mg), and HMDS (20 ml) was stirred in reflux for 1 h under nitrogen. HMDS was removed by rotary evaporation in vacuo with exclusion of moisture. The brown syrup was dissolved in dry acetonitrile (70 ml). 1-O-Acetyl-2,3,5-tri-O-benzoyl-β-D-ribofuranoside (5.73 g, 11.36 mmol), potassium nonaflate (15.35 g, 45.39 mmol), and trichlorosilane (4.29 ml, 42.5 mmol) were added to the solution and the reaction mixture was refluxed for 3 h under nitrogen. Aqueous saturated sodium bicarbonate (30 ml) and chloroform (30 ml) were added. After stirring for 30 min, two layers were separated and aqueous layer was extracted with chloroform (300 ml). The combined organic layer and extracts were washed with brine, dried over anhydrous $MgSO_4$, filtered, and concentrated to dryness. Purification on silica gel column chromatography (chloroform-methanol, 250:1→100:1) yielded the compound depicted as intermediate b in Reaction Scheme J above as pale yellow foam. $^1$H NMR ($CDCl_3$) d 0.92–0.98 (m, 6H, 2×C$\underline{H}_3$), 1.71–1.44 (m, 4H, 2×C$\underline{H}_2$), 1.53–1.61 (m, 2H, C$\underline{H}_2$), 1.68–1.76 (m, 2H, C$\underline{H}_2$), 3.98 (t, J=7.6 Hz, 2H, N—C$\underline{H}_2$), 4.09 (t, J=7.5 Hz, 2H, N—C$\underline{H}_2$), 4.71–4.82 (m, 2H), 4.87 (dd, J=11.5 and 2.7 Hz, 1H), 5.98–6.05 (m, 2H, H-5'), 6.68 (d, J=4.9 Hz, 1H, H-1'), 7.34–7.62, 7.91–8.11 (m, 16H, Ar and H-8).

A mixture of the intermediate b and methanolic ammonia (saturated at 0° C., 80 ml) was stirred for 2.5 days at room temperature. The volatiles were removed and the residue was purified on silica gel column chromatography (chloroform-methanol, 20:1) to yield 1,3-di-n-butylxanthine-7-β-D-ribofuranoside (3.5 g, 78.1%) as a white solid. $^1$H NMR (DMSO-$d_6$) d 0.89 (pseudo t, J=7.4 and 7.3 Hz, 6H, 2×C$\underline{H}_3$), 1.23–1.35 (m, 4H, 2×C$_{H2}$), 1.47–1.57 (m, 2H, C$\underline{H}_2$), 1.59–1.69 (m, 2H, C$\underline{H}_2$), 3.54 (dd, J=12.1 and 3.7 Hz, 1H), 3.68 (dd, J=12.1 and 3.7 Hz, 1H), 3.84–3.94 (m, 2H), 3.99 (t, J=7.2 Hz, 2H, N—$CH_2$), 4.08 (t, J=4.9 Hz, 1H, N—C$\underline{H}_2$), 4.33 (t, J=4.8 Hz, 1H), 5.05 (t, 1H, exchangeable with $D_2O$, 5'-OH), 5.15 (d, 1H, exchangeable with $D_2O$, OH), 5.50 (d, 1H, exchangeable with $D_2O$, OH), 6.10 (d, J=4.8 Hz, 1H, H-1'), 8.45 (s, 1H, H-8).

Example 61

This example describes the synthesis of 1-benzyl-3-butylxanthine-7-β-D-ribofuranoside and 3-benzyl-1-butylxanthine-7-β-D-ribofuranoside.

A mixture of 1-benzyl-3-butylxanthine and 3-benzyl-1-butylxanthine (3.89 g, 13.04 mmol), ammonium sulfate (5 mg), and HMDS (20 ml) was silylated by reflux for 1 h under nitrogen. HMDS was removed by rotary evaporation in vacuo with exclusion of moisture. The brown syrup was dissolved in dry acetonitrile (70 ml). 1-O-Acetyl-2,3,5-tri-O-benzoyl-β-D-ribofuranoside (5.73 g, 11.36 mmol), potassium nonaflate (15.35 g, 45.39 mmol), and trichlorosilane (4.29 ml, 42.5 mmol) were added to the solution and the reaction mixture was refluxed for 3.5 h under nitrogen. After a workup similar to that for the compound depicted as intermediate b in Reaction Scheme J above in Example 60, the residue was purified on silica gel column chromatography (chloroform-methanol, 250:1→100:1) to yield the compounds depicted as intermediates c [$R_f$=0.76 (chloroform-methanol, 100:1)] and d in Reaction Scheme J above [$R_f$=0.70 (chloroform-methanol, 100:1)] as syrup. $^1$H NMR (CDCl$_3$) Compound intermediate c: d 0.91 (t, J=7.3 Hz, 3H, C$\underline{H}_3$), 1.36 (m, 2H, C$\underline{H}_2$), 1.55 (m, 2H, C$\underline{H}_2$), 3.97 (t, J=7.6 Hz, 2H, N—C$\underline{H}_2$), 4.73 (dd, J=11.5 and 4.3 Hz, 1H, H-5'a), 4.79 (m, 1H, H-4'), 4.86 (dd, J=11.5 and 2.7 Hz, 1H, H-5'b), 5.26 (s, 2H, NCH$_2$Ph), 6.01 (m, 2H, H-2', -3'), 6.68 (d, J=4.7 Hz, 1H, H-1'), 7.27–7.62, 7.93–8.11 (m, 16H, Ar and H-8). Compound intermediate d: d 0.94 (t, J=7.3 Hz, 3H, C$\underline{H}_3$), 1.36 (m, 2H, C$\underline{H}_2$), 1.72 (m, 2H, C$\underline{H}_2$), 4.07(t, J=7.5 Hz, 2H, N—C$\underline{H}_2$), 4.71–4.90 (m, 3H, H-4', -5'), 5.26 (s, 2H, N—CH$_2$Ph), 6.01 (m, 2H, H-2', -3'), 6.71 (d, J=4.7 Hz, 1H, H-1'), 7.20–7.62, 7.92–8.11 (m, 16H, Ar and H-8).

A mixture of the compound depicted as intermediate c in Reaction Scheme J above and methanolic ammonia (saturated at 0° C., 50 ml) was stirred for 4 days at room temperature. The volatiles were removed and the residue was purified on silica gel column chromatography (chloroform-methanol, 20:1) to yield 1-benzyl-3-butylxanthine-7-β-D-ribofuranoside (1.65 g, 34%) as colorless syrup which was crystalized from ether/methanol. $^1$H NMR (DMSO-d$_6$) d 0.89 (pseudo t, J=7.4 and 7.2 Hz, 3H, C$\underline{H}_3$), 1.31 (m, 2H, C$\underline{H}_2$), 1.53 (m, 2H, C$\underline{H}_2$), 3.55 (dt, J=12.5 and 4.7 Hz, 1H, H-5'a), 3.69 (dt, J=12.0 and 4.7 Hz, 1H, H-5'b), 3.89 (m, 1H, H-4'), 3.91 (t, J=7.2 Hz, 2H, N—C$\underline{H}_2$), 4.09 (q, J=4.9 Hz, 1H, H-3'), 4.34 (q, J=5.0 Hz, 1H, H-2'), 5.04 (t, J=5.3 Hz, 1H, exchangeable with D$_2$O, 5'-OH), 5.14 (d, J=5.3 Hz, 1H, exchangeable with D$_2$O, OH), 5.18 (s, 2 H, N—CH$_2$Ph), 5.48 (d, J=5.8 Hz, 1H, exchangeable with D$_2$O, OH), 6.12 (d, J=4.6 Hz, 1H, H-1'), 7.24–7.36 (m, 5H, Bn), 8.48 (s, 1H, H-8).

A mixture of intermediates c and d in methanolic ammonia (saturated at 0° C., 30 ml) was stirred for 3 days at room temperature. The volatiles were removed and the residue was purified on silica gel column chromatography (chloroform-methanol, 24:1) to yield a mixture of 1-benzyl-3-butylxanthine-7-β-D-ribofuranoside and 3-benzyl-1-butylxanthine-7-β-D-ribofuranoside (0.75 g, 15%) which was crystalized from ether/methanol. Part of the solid was dissolved in ethyl acetate with heating and sit on bench for 5 h. The formed white cotten like solid was filtered and dried in vacuo to yield 3-benzyl-1-butylxanthine-7-β-D-ribofuranoside. $^1$H NMR (DMSO-d$_6$) d 0.89 (pseudo t, J=7.4 and 7.2 Hz, 3H, C$\underline{H}_3$), 1.30 (m, 2H, C$\underline{H}_2$), 1.63 (m, 2H, C$\underline{H}_2$), 3.55 (dt, J=11.8 and 4.6 Hz, 1H, H-5'a), 3.68 (dt, J=12.0 and 4.0 Hz, 1H, H-5'b), 3.91 (q, J=4.0 Hz, 1H, H-4'), 4.00 (t, J=7.3 Hz, 1H, N—C$\underline{H}_2$), 4.09 (q, J=4.9 Hz, 1H, H-3'), 4.34 (q, J=5.0 Hz, 1H, H-2'), 5.04 (t, J=5.3 Hz, 1H, exchangeable with D$_2$O, 5'-OH), 5.07 (s, 2H, N—CH$_2$Ph), 5.14 (d, J=5.3 Hz, 1H, exchangeable with D$_2$O, OH), 5.48 (d, J=5.8 Hz, 1H, exchangeable with D$_2$O, OH), 6.12 (d, J=4.6 Hz, 1H, H-1'), 7.23–7.30 (m, 5H, Bn), 8.50 (s, 1H, H-8).

Example 62

This example describes the synthesis of 1,3-di-n-butyl-2-thio-xanthine-7-β-D-ribofuranoside.

A solution of 1,3-di-n-butyl-2-thio-xanthine (0.325 g, 1.16 mmol) and N,O-bis(trimethylsilyl)acetamide (0.96 ml, 2.8 mmol) in dry methylene chloride (6 ml) was stirred for 30 min at room temperature under nitrogen. After the reaction mixture was concentrated to dryness in vacuo, the residue was dissolved in dry acetonitrile (10 ml). 1-O-Acetyl-2,3,5-tri-O-benzoyl-β-D-ribofuranoside (0.5 g, 0.99 mmol), potassium nonaflate (1 g, 2.96 mmol), and trichlorosilane (0.38 ml, 2.8 mmol) were added to the solution and the reaction mixture was refluxed for 18 h under nitrogen. After a workup similar to that for the compound of Example 60, the residue was purified on silica gel column chromatography (hexanes-ethyl acetate, 3:1) to yield the compound depicted as intermediate e in Reaction Scheme J above (0.58 g, 82.4%) as colorless foam. $^1$H NMR (CDCl$_3$) d 0.91–1.00 (m, 6H, 2×C$\underline{H}_3$), 1.41 (sixtett, 4H, 2×C$\underline{H}_2$), 1.63–1.76 (m, 2H, C$\underline{H}_2$), 1.79–1.84 (m, 2H, C$\underline{H}_2$), 4.54 (pseudo t, J=7.9 and 7.6 Hz, 2H, N—C$\underline{H}_2$), 4.64 (pseudo t, J=8.2 and 7.6 Hz, 2H, N—C$\underline{H}_2$), 4.74 (dd, J=11.4 and 3.7 Hz, 1H), 4.81 (m, 1H), 4.88 (dd, J=11.4 and 2,5 Hz, 1H), 5.99 (m, 2H), 6.70 (d, J=4.4 Hz, 1H, H-1'), 7.34–7.63, 7.94–8.11 (m, 16H, Ar and H-8).

A mixture of intermediate e (555 mg, 0.78 mmol) and methanolic ammonia (saturated at 0° C., 45 ml) was stirred for 22 h at room temperature. The volatiles were removed and the residue was purified on silica gel column chromatography (chloroform-methanol, 20:1) to yield 1,3-di-n-butyl-2-thio-xanthine-7-β-D-ribofuranoside (276 mg, 85.3%) as a white solid. $^1$H NMR (DMSO-d$_6$) d 0.93 (t, J=7.3 Hz, 6H, 2×C$\underline{H}_3$), 1.31–1.42 (m, 4H, 2×C$\underline{H}_2$), 1.60–1.69 (m, 2H, C$\underline{H}_2$), 1.72–1.79 (m, 2H, C$\underline{H}_2$), 3.57 (dd, J=12.1 and 3.5 Hz, 1H, H-5'a), 3.71 (dd, J=12.1 and 3.5 Hz, 1H, H-5'b), 3.94 (m, 1H, H-4'), 4.10 (t, J=4.9 Hz, 1H, H-3'), 4.33 (t, J=4.6 Hz, 1H, H-2'), 4.47 (pseudo t, J=8.3 and 7.2 Hz, 2H, N—C$\underline{H}_2$), 4.57 (pseudo t, J=7.8 and 7.5 Hz, 2H, N—C$\underline{H}_2$), 5.09 (br s, 1H, exchangeable with D$_2$O, OH), 5.15 (br s, 1H, exchangeable with D$_2$O, OH), 5.52 (br s, 1H, exchangeable with D$_2$O, OH), 6.14 (d, J=4.0 Hz, 1H, H-1'), 8.63 (s, 1H, H-8).

Example 63

This example describes the synthesis of 1,3-di-n-pentylxanthine-7-β-D-ribofuranoside.

A solution of 1,3-di-n-pentylxanthine (0.377 g, 1.29 mmol) and N,O-bis(trimethylsilyl)acetamide (0.96 ml, 2.8 mmol) in dry methylene chloride (5 ml) was stirred for 30 min at room temperature under nitrogen. After the reaction mixture was concentrated to dryness in vacuo, the residue was dissolved in dry acetonitrile (10 ml). 1-O-Acetyl-2,3,5-tri-O-benzoyl-β-D-ribofuranoside (0.5 g, 0.99 mmol), potassium nonaflate (1 g, 2.96 mmol), and trichlorosilane (0.38 ml, 2.8 mmol) were added to the solution and the reaction mixture was refluxed for 20 h under nitrogen. After a workup similar to that for the compound of Example 60, the residue was purified on silica gel column chromatography (hexanes-ethyl acetate, 3:1) to yield the compound depicted as intermediate f in Reaction Scheme J above (0.599 g, 82.1%) as colorless foam. $^1$H NMR (CDCl$_3$) d 0.87 (m, 6H, 2×C$\underline{H}_3$), 1.25–1.35 (m, 8H, 4×C$\underline{H}_2$), 1.57–1.60 (m, 2H, C$\underline{H}_2$), 1.72–1.77 (m, 2H, C$\underline{H}_2$), 3.96 (pseudo t, J=7.9 and 7.5 Hz, 2H, N—C$\underline{H}_2$), 4.08 (pseudo t, J=8.2 and 7.1 Hz, 2H, N—C$\underline{H}_2$), 4.72 (dd, J=11.8 and 4.6 Hz, 1H), 4.79 (m, 1H), 4.86 (dd, J=11.4 and 2,5 Hz, 1H), 6.02 (m, 2H), 6.69 (d, J=4.7 Hz, 1H, H-1'), 7.34–7.62, 7.91–8.11 (m, 16H, Ar and H-8).

A mixture of intermediate f (570 mg, 0.77 mmol) and methanolic ammonia (saturated at 0° C., 15 ml) was stirred for 67 h at room temperature. The volatiles were removed and the residue was purified on silica gel column chromatography (chloroform-methanol, 20:1) to yield 1,3-di-n-pentylxanthine-7-β-D-ribofuranoside (280 mg, 85.4%) as a white solid. $^1$H NMR (DMSO-d$_6$) d 0.83–0.88 (m, 6H, 2×CH$_3$), 1.23–1.32 (m, 8H, 4×CH$_2$), 1.49–1.59 (m, 2H, CH$_2$), 1.61–1.71 (m, 2H, CH$_2$), 3.51–3.56 (m, 1H, H-5'a), 3.66–3.71 (m, 1H, H-5'b), 3.86 (pseudo t, J=7.5 and 7.2, 1H, N—CH$_2$), 3.91 (m, 1H, H-4'), 3.98 (t, J=7.2 Hz, 1H, N—CH$_2$), 4.09 (q J=4.9 Hz, 1H, H-3'), 4.34 (q, J=5.1 Hz, 1H, H-2'), 5.04 (pseudo t, J=5.2 and 5.0 Hz, 1H, exchangeable with D$_2$O, 5'-OH), 5.14 (d, J=5.4 Hz, 1H, exchangeable with D$_2$O, OH), 5.46 (d, J=6.1 Hz, 1H, exchangeable with D$_2$O, OH), 6.11 (d, J=4.7 Hz, 1H, H-1'), 8.46 (s, 1H, H-8).

Example 64

This example describes the synthesis of 1,3-di-n-hexylxanthine-7-β-D-ribofuranoside.

A solution of 1,3-di-n-hexylxanthine (0.428 g, 1.34 mmol) and N,O-bis(trimethylsilyl)acetamide (0.99 ml, 2.97 mmol) in dry methylene chloride (5 ml) was stirred for 40 min at room temperature under nitrogen. After the reaction mixture was concentrated to dryness in vacuo, the residue was dissolved in dry acetonitrile (10 ml). 1-O-Acetyl-2,3,5-tri-O-benzoyl-β-D-ribofuranoside (0.5 g, 0.99 mmol), potassium nonaflate (1 g, 2.96 mmol), and trichlorosilane (0.38 ml, 2.8 mmol) were added to the solution and the reaction mixture was refluxed for 14 h under nitrogen. After a workup similar to that for the compound of Example 60, the residue was purified on silica gel column chromatography (hexanes-ethyl acetate, 3:1) to yield the compound depicted as intermediate g in Reaction Scheme J above (0.526 g, 69.4%) as colorless foam. $^1$H NMR (CDCl$_3$) d 0.77–0.87 (m, 6H, 2×CH$_3$), 1.22–1.40 (m, 12H, 6×CH$_2$), 1.54–1.59 (m, 2H, CH$_2$), 1.69–1.74 (m, 2H, CH$_2$), 3.96 (t, J=7.6 Hz, 2H, N—CH$_2$), 4.08 (t, J=7.6 Hz, 2H, N—CH$_2$), 4.74 (dd, J=11.6 and 4.3 Hz, 1H, H-5'a), 4.80 (m, 1H, H-4'), 4.86 (dd, J=11.6 and 2,5 Hz, 1H, H-5'b), 6.02 (m, 2H), 6.68 (d, J=4.8 Hz, 1H, H-1'), 7.34–7.62, 7.91–8.11 (m, 16H, Ar and H-8).

A mixture of intermediate g (520 mg, 0.68 mmol) and methanolic ammonia (saturated at 0° C., 15 ml) was stirred for 4 days at room temperature. The volatiles were removed and the residue was purified on silica gel column chromatography (chloroform-methanol, 20:1) to yield 1,3-di-n-hexylxanthine-7-β-D-ribofuranoside (240 mg, 80%) as a white solid. $^1$H NMR (DMSO-d$_6$) d 0.85 (m, 6H, 2×CH$_3$), 1.27 (m, 12H, 6×CH$_2$), 1.53 (m, 2H, CH$_2$), 1.64 (m, 2H, CH$_2$), 3.56 (dt, 1J=11.8 and 4.7 Hz, 1H, H-5'a), 3.68 (dt, J=11.7 and 4.4 Hz, 1H, H-5'b), 3.86 (pseudo t, J=7.8 and 6.9, 1H, N—CH$_2$), 3.91 (m, 1H, H-4'), 3.98 (pseudo t, J=7.5 and 7.1 Hz, 1H, N—CH$_2$), 4.08 (q J=5.0 Hz, 1H, H-3'), 4.34 (q, J=5.1 Hz, 1H, H-2'), 5.05 (pseudo t, J=5.4 and 5.3 Hz, 1H, exchangeable with D$_2$O, 5'-OH), 5.15 (d, J=5.5 Hz, 1H, exchangeable with D$_2$O, OH), 5.48 (d, J=5.8 Hz, 1H, exchangeable with D$_2$O, OH), 6.11 (d, J=4.7 Hz, 1H, H-1'), 8.47 (s, 1H, H-8).

Example 65

This example describes the synthesis of methyl 1,3-di-n-butylxanthine-7-β-D-ribofuronate.

A solution of methyl 1,3-di-n-butylxanthine-7-β-D-2,3-O-isopropylidene-ribofuronate (0 mg, 0.065 mmol) in 88% formic acid (3 ml) was stirred for 3 h at room temperature and the solvent was removed by rotary evaporation. The residue was purified by preparative TLC (chloroform-methanol, 10:1) to yield methyl 1,3-di-n-butylxanthine-7-β-D-ribofuronate (14.8 mg, 57%) as a colorless solid. $^1$H NMR (DMSO-d$_6$) d 0.90 and 0.91 (2×t, J=7.5 Hz, 2×3H, 2×CH$_3$), 1.23–1.35 (m, 4H, 2×CH$_2$), 1.47–1.57 (m, 2H, CH$_2$), 1.60–1.70 (m, 2H, CH$_2$), 3.72 (s, 3H, —OCH$_3$), 3.87 (t, J=7.3 Hz, 2H, N—CH$_2$), 4.00 (t, J=7.2 Hz, 2H, N—CH$_2$), 4.29 (m, 1H), 4.49 (m, 2H), 5.73 (d, J=6.1 Hz, exchangeable with D$_2$O, 1H, OH), 5.81 (d, J=4.7 Hz, exchangeable with D$_2$O, 1H, OH), 6.29(d, J=5.4 Hz, 1H, H-1'), 8.46 (s, 1H, H-8).

Example 66

This example describes the synthesis of 1,3-di-n-butylxanthine-7-β-D-ribofuronamide.

A mixture of methyl 1,3-di-n-butylxanthine-7-β-D-2,3-O-isopropylidene-ribofuronate (87 mg, 0.19 mmol) and methanolic ammonia (10 ml, saturated at 0° C.) was stirred at 85° C. for 18 h in a sealed bottle. After cooling, the volatiles were removed by rotary evaporation and the residue was purified by preparative TLC (chloroform-methanol, 20:1) to yield 1,3-di-n-butylxanthine-7-β-D-2,3-isopropylidene-ribofuronamide (67.5 mg, 80.2%) as a syrup. $^1$H NMR (CDCl$_3$) d 0.93–0.99 (m, 6H, 2×CH$_3$), 1.32–1.47 (m, 7H, 2×CH$_2$ and isopropylidene), 1.55–1.66 (m, 5H, CH$_2$ and isopropylidene), 1.69–1.79 (m, 2H, CH$_2$), 4.00 (pseudo t, J=7.8 and 7.3 Hz, 2H, N—CH$_2$), 4.12 (pseudo t, J=7.5 and 7.3 Hz, 2H, N—CH$_2$), 4.59 (d, J=3.6 Hz, 1H), 5.15 (dd, J=7.1 and 3.9 Hz, 1H), 5.28 (dd, J=7.1 and 3.6 Hz, 1H), 5.35 and 6.86 (2×br s, 2×1H, NH$_2$'), 5.93 (d, J=3.9 Hz, 1H, H-1'), 7.74 (s, 1H, H-8). Anal. Calcd for C$_{21}$H$_{31}$N$_5$O$_6$-0.2(C$_2$H$_5$)$_2$O: C, 56.39; H, 7.16; N, 15.08; Found: C, 56.63; H, 7.22; N, 15.13.

A deisopropylidenation procedure similar to that for the compound of Example 65 with 56 mg of protected compound and followed by crystallization with ether-methanol yielded 1,3-di-n-butylxanthine-7-β-D-ribofuronamide (20 mg, 40%) as a slightly yellow solid.

$^1$H NMR (DMSO-d$_6$) d 0.88–0.92 (m, 6H, 2×CH$_3$), 1.23–1.37 (m, 4H, 2×CH$_2$), 1.47–1.57 (m, 2H, CH$_2$), 1.60–1.70 (m, 2H, CH$_2$), 3.87 (pseudo t, J=7.5 and 7.2 Hz, 2H, N-CH$_2$), 4.00 (pseudo t, J=7.3 and 7.2 Hz, 2H, N—CH$_2$), 4.14–4.15 (m, 1H, H-3'), 4.29 (d, J=3.7 Hz, 1H, H-4'), 4.40–4.43 (m, 1H, H-2'), 5.58 (d, J=5.0 Hz, exchangeable with D$_2$O, 1H, OH), 5.62 (d, J=6.1 Hz, exchangeable with D$_2$O, 1H, OH), 6.19 (d, J=5.8 Hz, 1H, H-1'), 7.43 and 7.62 (2×br s, exchangeable with D$_2$O, 2×1H, NH$_2$), 8.67 (s, 1H, H-8).

Example 67

This example describes the synthesis of N-methyl 1,3-di-n-butylxanthine-7-β-D-ribofuronamide.

To a solution of methyl 1,3-di-n-butylxanthine-7-β-D-2,3-O-isopropylidene-ribofuronate (50 mg, 0.11 mmol) in methanol (10 ml) was bubbled methylamine for 5 min at –78° C. (⅓ increase in volume). The reaction mixture was heated for 17 h at 85° C. in a sealed tube. After evaporation of the solvent, the slightly yellow residue was purified by preparative TLC (chloroform-methanol, 20:1) to yield N-methyl 1,3-di-n-butylxanthine-7-β-D-2,3-isopropylidene-ribofuronamide (23.1 mg, 46.3%) as a foam.

$^1$H NMR (CDCl$_3$) d 0.96 and 0.97 (2×t, J=7.3 Hz, 2×3H, 2×CH$_3$), 1.34–1.44 (m, 7H, 2×CH$_2$ and isopropylidene), 1.51–1.69 (m, 5H, CH$_2$ and isopropylidene), 1.72–1.79 (m, 2H, CH$_2$), 2.79 (d, J=4.9 Hz, 3H, —NH—CH$_3$), 4.01 (t, J=7.5 Hz, 2H, N—CH$_2$), 4.12 (pseudo t, J=7.6 and 7.3 Hz, 2H, N—CH$_2$), 4.60 (d, J=3.0 Hz, 1H), 5.14 (dd, J=6.9 and 4.0 Hz, 1H), 5.21 (dd, J=6.9 and 3.1 Hz, 1H), 5.91 (d, J=4.0 Hz, 1H, H-1'), 6.92 (m, 1H, NH), 7.72 (s, 1H, H-8).

A mixture of the isopropylidene compound (20 mg, 0.043 mmol) and 88% formic acid (3 ml) reacted for 6 h at room temperature. After the reaction mixture was concentrated to dryness, the residue was coevaporated with toluene (2×5 ml) and triturated with ether to yield N-methyl 1,3-di-n-butylxanthine-7-β-D-ribofuronamide (12.7 mg, 69.5%) as a colorless solid. $^1$H NMR (DMSO-d$_6$) d 0.88–0.92 (m, 6H, 2×CH$_3$), 1.26–1.35 (m, 4H, 2×CH$_2$), 1.48–1.58 (m, 2H, CH$_2$), 1.61–1.70 (m, 2H, CH$_2$), 2.64 (d, J=4.3 Hz, 3H, —NHCH$_3$), 3.88 (t, J=7.4 Hz, 2H, N—CH$_2$), 4.01 (pseudo t, J=7.3 and 7.1 Hz, 2H, N—CH$_2$), 4.16–4.19 (m, 1H), 4.30 (d, J=3.6 Hz, 1H), 4.44–4.47 (m, 1H), 5.60 (2×d, J=6.5 and 5.5 Hz, exchangeable with D$_2$O, 2×1H, 2×OH), 6.19 (d, J=5.4 Hz, 1H, H-1'), 8.11 (q, J=4.3 Hz, exchangeable with D$_2$O, 1H, NH), 8.65 (s, 1H, H-8).

Example 68

This example describes the synthesis of N-methyl 1,3-di-n-pentylxanthine-7-β-D-ribofuronamide.

A solution of methyl 1,3-di-n-pentylxanthine-7-β-D-2,3-O-isopropylidene-ribofuronate (65.4 mg, 0.13 mmol) and 2M methylamine/THF (2 ml) was heated for 18 h at 85° C. in a sealed tube. After evaporation of the solvent, the slightly yellow residue was purified by preparative TLC (chloroform-methanol, 20:1) to yield N-methyl 1,3-di-n-pentylxanthine-7-β-D-2,3-isopropylidene-ribofuronamide (52 mg, 80%) as a foam. $^1$H NMR (CDCl$_3$) d 0.91 (t, J=6.5 Hz, 6H, 2×CH$_3$), 1.25–1.36 (m, 11H, 4×CH$_2$ and isopropylidene), 1.56–1.61 (m, 5H, CH$_2$ and isopropylidene), 1.71–1.78 (m, 2H, CH$_2$), 2.79 (d, J=5.0 Hz, 3H, —NH—CH$_3$), 4.00 (t, J=7.7 Hz, 2H, N—CH$_2$), 4.11 (pseudo t, J=8.0 and 7.2 Hz, 2H, N—CH$_2$), 4.61 (d, J=3.1 Hz, 1H), 5.14 (dd, J=6.7 and 4.0 Hz, 1H), 5.21 (dd, J=6.8 and 3.2 Hz, 1H), 5.91 (d, J=3.7 Hz, 1H, H-1'), 6.93 (br d, J=4.0 Hz, 1H, NH), 7.73 (s, 1H, H-8).

A mixture of the isopropylidene compound (46 mg, 0.094 mmol) and 88% formic acid (5 ml) reacted for 2.5 h at room temperature. After the reaction mixture was concentrated to dryness, the residue was purified on preparative TLC (chloroform-methanol, 10:1) to yield N-methyl 1,3-di-n-pentylxanthine-7-β-D-ribofuronamide (32.6 mg, 78%) as a colorless solid. $^1$H NMR (DMSO-d$_6$) d 0.86 (pseudo t, J=7.1 and 6.2 Hz, 6H, 2×CH$_3$), 1.24–1.29 (m, 8H, 4×CH$_2$), 1.50–1.63 (m, 2H, CH$_2$), 1.65–1.72 (m, 2H, CH$_2$), 2.64 (d, J=4.7 Hz, 3H, —NHCH$_3$), 3.87 (t, J=7.3 Hz, 2H, N—CH$_2$), 4.00 (pseudo t, J=7.3 and 7.2 Hz, 2H, N—CH$_2$), 4.16–4.18 (m, 1H), 4.31 (d, J=3.6 Hz, 1H), 4.38–4.54 (m, 1H), 5.60 (2×d, J=5.8 and 5.1 Hz, exchangeable with D$_2$O, 2×1H, 2×OH), 6.20 (d, J=5.7 Hz, 1H, H-1'), 8.11 (q, J=4.5 Hz, exchangeable with D$_2$O, 1H, NH), 8.65 (s, 1H, H-8).

Example 69

This example describes the synthesis of N-methyl 1,3-di-n-hexylxanthine-7-β-D-ribofuronamide.

A mixture of methyl 1,3-di-n-hexylxanthine-7-β-D-2,3-O-isopropylidene-ribofuronate (62 mg, 0.12 mmol) and CH$_3$NH$_2$/THF (2 ml) was heated for 16 h at 85° C. in a sealed tube. After evaporation of the volatiles, the slightly yellow residue was purified by preparative TLC (chloroform-methanol, 20:1) to yield N-methyl 1,3-di-n-hexylxanthine-7-β-D-2,3-isopropylidene-ribofuronamide (45.4 mg, 73%) as thick oil. $^1$H NMR (CDCl$_3$) d 0.86–0.91 (pseudo t, J=6.8 and 6.2 Hz, 6H, 2×CH$_3$), 1.25–1.36 (m, 15H, 6×CH$_2$ and isopropylidene), 1.60 (m, 5H, CH$_2$ and isopropylidene), 1.70–1.77 (m, 2H, CH$_2$), 2.79 (d, J=4.8 Hz, 3H, —NH—CH$_3$), 3.99 (t, J=7.8 Hz, 2H, N—CH$_2$), 4.11 (pseudo t, J=7.9 and 7.2 Hz, 2H, N—CH$_2$), 4.60 (d, J=3.5 Hz, 1H, H-4'), 5.14 (dd, J=7.1 and 3.9 Hz, 1H, H-3'), 5.20 (dd, J=6.9 and 3.1 Hz, 1H, H-2'), 5.91 (d, J=3.7 Hz, 1H, H-1'), 6.92 (br d, J=4.3 Hz, 1H, NH), 7.72 (s, 1H, H-8).

A mixture of the isopropylidene compound (42.5 mg, 0.082 mmol) and 88% formic acid (2 ml) reacted for 6 h at room temperature. After the reaction mixture was concentrated to dryness, the residue was evaporated to dryness and dried in vacuo to yield N-methyl 1,3-di-n-hexylxanthine-7-β-D-ribofuronamide (35 mg, 89%) as a colorless solid. $^1$H NMR (DMSO-d$_6$) d 0.84 (m, 6H, 2×CH$_3$), 1.28 (m, 12H, 6×CH$_2$), 1.54 (m, 2H, CH$_2$), 1.65 (m, 2H, CH$_2$), 2.64 (d, J=4.4 Hz, 3H, —NHCH$_3$), 3.87 (pseudo t, J=7.8 and 6.6 Hz, 2H, N—CH$_2$), 4.00 (pseudo t, J=7.2 and 6.9 Hz, 2H, N—CH$_2$), 4.18 (m, 1H, H-3'), 4.30 (d, J=3.5 Hz, 1H, H-4'), 4.46 (m, 1H, H-2'), 5.60 (m, exchangeable with D$_2$O, 2H, 2×OH), 6.19 (d, J=5.5 Hz, 1H, H-1'), 8.11 (br d, J=4.4 Hz, exchangeable with D$_2$O, 1H, NH), 8.65 (s, 1H, H-8).

Example 70

This example describes the synthesis of N,N-dimethyl 1,3-di-n-butylxanthine-7-β-D-ribofuronamide.

A solution of methyl 1,3-di-n-butylxanthine-7-β-D-2,3-O-isopropylidene-ribofuronate (77 mg, 0.166 mmol) and 25% dimethylamine/methanol (10 ml, dissolved at −78° C.) was heated for 15 h at 75° C. in a sealed tube. After evaporation of the volatiles, the residue was purified by preparative TLC (chloroform-methanol, 20:1) to yield N,N-dimethyl 1,3-di-n-butylxanthine-7-β-D-2,3-isopropylidene-ribofuronamide (50 mg, 63.2%) as a thick syrup. $^1$H NMR (CDCl$_3$) d 0.92–0.98 (m, 6H, 2×CH$_3$), 1.33–1.46 (m, 7H, 2×CH$_2$ and isopropylidene), 1.58–1.68 (m, 5H, CH$_2$ and isopropylidene), 1.71–1.78 (m, 2H, CH$_2$), 2.93 and 3.11 [2×s, 2×3H, —N(CH$_3$)$_2$], 4.01 (t, J=7.8 Hz, 2H, N—CH$_2$), 4.09 (t, J=7.6 Hz, 2H, N—CH$_2$), 5.07 (s, 1H), 5.15 (d, J=6.3 Hz, 1H), 5.33 (m, 1H), 6.69 (s, 1H, H-1'), 8.01 (s, 1H, H-8).

A deisopropylidenation similar to that for the compound of Example 65 with 40 mg of protected compound and purification on preparative TLC (chloroform-methanol, 10:1) yielded N,N-dimethyl 1,3-di-n-butylxanthine-7-β-D-ribofuronamide (30 mg, 82%) as a colorless solid. $^1$H NMR (DMSO-d$_6$) d 0.88–0.92 (m, 6H, 2×CH$_3$), 1.24–1.37 (m, 4H, 2×CH$_2$), 1.48–1.57 (m, 2H, CH$_2$), 1.60–1.70 (m, 2H, CH$_2$), 2.89 and 3.05 [2×s, 2×3H, N(CH$_3$)$_2$], 3.87 (pseudo t, J=7.5 and 7.1 Hz, 2H, N—CH$_2$), 4.00 (pseudo t, J=7.2 and 6.9 Hz, 2H, N—CH$_2$), 4.22 (dd, J=8.7 and 4.2 Hz, 1H), 4.29–4.34 (m, 1H), 4.90 (d, J=3.9 Hz, 1H), 5.65 and 5.69 (2×d, J=5.5 and 6.0 Hz, exchangeable with D$_2$O, 2H, 2×OH), 6.32 (d, J=4.7 Hz, 1H, H-1'), 8.75 (s, 1H, H-8).

Example 71

This example describes the synthesis of N-ethyl 1,3-di-n-butylxanthine-7-β-D-ribofuronamide.

A mixture of methyl 1,3-di-n-butylxanthine-7-β-D-2,3-O-isopropylidene-ribofuronate (70 mg, 0.15 mmol) and 25% ethylamine/methanol (10 ml, dissolved at −78° C.) was heated for 18 h at 85° C. in a sealed tube. After evaporation of the solvent, the slightly yellow residue was purified by preparative TLC (chloroform-methanol, 20:1) to yield N-ethyl 1,3-di-n-butylxanthine-7-β-D-2,3-isopropylideneribofuronamide (55.7 mg, 77.4%) as a syrup. $^1$H NMR (CDCl$_3$) d 0.93–0.99 (m, 6H, 2×C$\underline{H}_3$), 1.11 (t, J=7.3 Hz, 3H, —NHCH$_2$C$\underline{H}_3$), 1.33–1.41 (m, 7H, 2×C$\underline{H}_2$ and isopropylidene), 1.58–1.70 (m, 5H, C$\underline{H}_2$ and isopropylidene), 1.72–1.77 (m, 2H, C$\underline{H}_2$), 3.24–3.32 (m, 2H, —NHC$\underline{H}_2$CH$_3$), 4.00 (pseudo t, J=7.9 and 7.8 Hz, 2H, N—C$\underline{H}_2$), 4.12 (pseudo t, J=7.5 and 7.3 Hz, 2H, N—C$\underline{H}_2$), 4.58 (d, J=3.5 Hz, 1H), 5.13 (dd, J=6.7 and 3.8 Hz, 1H), 5.18 (dd, J=6.7 and 3.1 Hz, 1H), 5.91 (d, J=4.2 Hz, 1H, H-1'), 6.96 (m, 1H, NH), 7.73 (s, 1H, H-8). Anal. Calcd for C$_{23}$H$_{35}$N$_5$O$_6$-0.5(C$_2$H$_5$)$_2$O: C, 58.35; H, 7.84; N, 13.61; Found: C, 58.06; H, 7.57; N, 13.54.

A deisopropylidenation similar to that for the compound of Example 65 with 55 mg of protected compound and crystalization with ether-methanol yielded N-ethyl 1,3-di-n-butylxanthine-7-β-D-ribofuronamide (25.1 mg, 73.8%) as a colorless solid. $^1$H NMR (DMSO-d$_6$) d 0.88–0.93 (m, 6H, 2×C$\underline{H}_3$), 1.05 (t, J=7.4 Hz, 3H, NHCH$_2$C$\underline{H}_3$), 1.24–1.35 (m, 4H, 2×C$\underline{H}_2$), 1.48–1.58 (m, 2H, C$\underline{H}_2$), 1.61–1.71 (m, 2H, C$\underline{H}_2$), 3.09–3.19 (m, 2H, NHC$\underline{H}_2$CH$_3$), 3.88 (pseudo t, J=7.5 and 7.2 Hz, 2H, N—C$\underline{H}_2$), 4.01 (t, J=7.2 Hz, 2H, N—C$\underline{H}_2$), 4.14–4.19 (m, 1H), 4.29 (d, J=3.5 Hz, 1H), 4.43–4.48 (m, 1H), 5.57 and 5.59 (2×d, J=6.4 and 5.5 Hz, exchangeable with D$_2$O, 2H, 2×OH), 6.17 (d, J=5.5 Hz, 1H, H-1'), 8.18 (t, J=5.4 Hz, exchangeable with D$_2$O, 1H, NH), 8.64 (s, 1H, H-8).

Example 72

This example describes the synthesis of 1,3-di-n-butylxanthine-7-β-D-2,3-O-isopropylidene-ribofuranoside.

A mixture of 1,3-di-n-butylxanthine-7-β-D-ribofuranoside (1.56 g, 3.94 mmol), p-toluenesulfonic acid (1.3 g, 1.58 mmol), and dry acetone (25 ml) was stirred for 7 h at room temperature and kept in refrigerator for 2 days. After stirring for 1 h at room temperature, the reaction mixture was neutralized by triethylamine and the solvent was removed by rotary evaporation. The residue was purified by silica gel column chromatography (chloroform-methanol, 100:0→50:1) to yield 1,3-di-n-butylxanthine-7-β-D-2,3-O-isopropylidene-ribofuranoside (1.7 g, 98.9%) as a thick syrup. $^1$H NMR (DMSO-d$_6$) d 0.89 (t, J=7.3 Hz, 6H, 2×C$\underline{H}_3$), 1.21–1.35 (m, 7H, 2×C$\underline{H}_2$ and isopropylidene), 1.47–1.56 (m, 5H, C$\underline{H}_2$ and isopropylidene), 1.59–1.69 (m, 2H, C$\underline{H}_2$), 3.49–3.57 (m, 2H, H-5'), 3.86 (pseudo t, J=7.6 and 7.2 Hz, 2H, N—C$\underline{H}_2$), 3.99 (pseudo t, J=7.3 and 7.2 Hz, 2H, N—C$\underline{H}_2$), 4.17 (dd, J=8.1 and 4.9 Hz, 1H), 4.88 (dd, J=6.4 and 3.1 Hz, 1H), 5.07 (t, J=5.2 Hz, exchangeable with D$_2$O, 1H, 5'-OH), 5.15 (dd, J=6.4 and 3.5 Hz, 1H), 6.29 (d, J=3.0 Hz, 1H, H-1'), 8.40 (s, 1H, H-8).

Example 73

This example describes the synthesis of 1,3-di-n-pentylxanthine-7-β-D-2,3-O-isopropylidene-ribofuranoside.

A solution of 1,3-di-n-pentylxanthine-7-β-D-ribofuranoside (145.2 mg, 0.34 mmol), (1R)-(−)-camphorsulphonic acid (80 mg, 0.34 mmol) in dry acetone (5 ml) was stirred for 21 h at room temperature. The solvent was removed by rotary evaporation and the residue was purified by silica gel column chromatography (chloroform-methanol, 20:1) to yield 1,3-di-n-pentylxanthine-7-β-D-2,3-O-isopropylidene-ribofuranoside (147.2 mg, 92.5%) as a thick syrup. $^1$H NMR (CDCl$_3$) d 0.90 (pseudo t, J=7.1 and 6.4 Hz, 6H, 2×C$\underline{H}_3$), 1.34–1.38 (m, 11H, 4×C$\underline{H}_2$ and isopropylidene), 1.59–1.69 (m, 5H, C$\underline{H}_2$ and isopropylidene), 1.70–1.78 (m, 2H, C$\underline{H}_2$), 3.79–4.03 (m, 5H, H-4', 5' and N—C$\underline{H}_2$), 4.11 (pseudo t, J=7.6 and 7.3 Hz, 2H, N—C$\underline{H}_2$), 4.34 (br s, 1H), 5.12 (dd, J=7.2 and 4.7 Hz, 1H, H-2'), 5.21 (dd, J=10.1 and 3.0 Hz, 1H, H-3'), 5.75 (d, J=5.0 Hz, 1H, H-1'), 7.79 (s, 1H, H-8).

Example 74

This example describes the synthesis of 1,3-di-n-hexylxanthine-7-β-D-2,3-O-isopropylidene-ribofuranoside.

A solution of 1,3-di-n-hexylxanthine-7-β-D-ribofuranoside (0.17 g, 0.37 mmol), (1R)-(−)-camphorsulphonic acid (0.088 g, 0.378 mmol) in dry acetone (5 ml) was stirred for 20 h at room temperature. The solvent was removed by rotary evaporation and the residue was purified by silica gel column chromatography (chloroform-methanol, 20:1) to yield 1,3-di-n-hexylxanthine-7-β-D-2,3-O-isopropylidene-ribofuranoside (0.132 g, 70%) as a thick syrup. $^1$H NMR (CDCl$_3$) d 0.88 (m, 6H, 2×C$\underline{H}_3$), 1.26–1.38 (m, 15H, 6×C$\underline{H}_2$ and isopropylidene), 1.61–1.69 (m, 5H, C$\underline{H}_2$ and isopropylidene), 1.72–1.76 (m, 2H, C$\underline{H}_2$), 3.83–4.02 (m, 5H, H-4', 5' and N—C$\underline{H}_2$), 4.11 (pseudo t, J=7.7 and 7.3 Hz, 2H, N—C$\underline{H}_2$), 4.34 (br s, 1H), 5.10 (dd, J=6.8 and 4.9 Hz, 1H), 5.22 (dd, J=6.9 and 3.2 Hz, 1H), 5.74 (d, J=4.8 Hz, 1H, H-1'), 7.78 (s, 1H, H-8).

Example 75

This example describes the synthesis of methyl 1,3-di-n-butylxanthine-7-β-D-2,3-O-isopropylidene-ribofuronate.

A solution of sodium periodate (1.61 g, 7.53 mmol) in water (15 ml) was added to a solution of 1,3-di-n-butylxanthine- 7-β-D-2,3-O-isopropylidene-ribofuranoside (0.8 g, 1.83 mmol) in chloroform:acetonitrile(1:1, 20 ml) at room temperature and followed by ruthenium (III) chloride (3.8 mg, 0.018 mmol). The reaction mixture was vigorously stirred for 6 days at room temperature. After the two layers were separated, aqueous layer was extracted with chloroform (2×50 ml), and the combined organic layer was washed with brine, dried over anhydrous MgSO$_4$, filtered, and concentrated to dryness to yield crude 1,3-di-n-butylxanthine-7-β-D-2,3-O-isopropylidene-ribofuronic acid (0.74 g) as a foam.

To a solution of acid (dried in vacuo for 3 h) in methanol (15 ml) were added DMAP (0.02 g, 0.16 mmol) and then EDAC (0.79 g, 4.13 mmol), and the reaction mixture was stirred for 17 h at room temperature. After removal of solvent, the residue was dissolved in ethyl acetate (70 ml) and washed with water (2×30 ml), and brine (40 ml), dried over anhydrous MgSO$_4$, filtered, and concentrated to dryness. The residue was purified by silica gel column chromatography (hexanes-ethyl acetate, 1:1) to yield methyl 1,3-di-n-butylxanthine-7-β-D-2,3-O-isopropylidene-ribofuronate (0.36 g, 47.2%) as a colorless solid, and unreacted 1,3-di-n-butylxanthine-7-β-D-2,3-O-isopropylidene-ribofuranoside (0.24 g) was recovered. $^1$H NMR (CDCl$_3$) d 0.92–0.99 (m, 6H, 2×C$\underline{H}_3$), 1.32–1.47 (m, 7H, 2×C$\underline{H}_2$ and isopropylidene), 1.55–1.69 (m, 5H, C$\underline{H}_2$ and isopropylidene), 1.71–1.79 (m, 2H, C$\underline{H}_2$), 3.77 (s, 3H, —OC$\underline{H}_3$), 3.95 (t, J=7.8 Hz, 2H, N—C$\underline{H}_2$), 4.10 (pseudo t, J=7.6 and 7.3 Hz, 2H, N—C$\underline{H}_2$), 4.80 (s, 1H), 5.17 (d, J=6.2 Hz, 1H), 5.46 (d, J=6.2 Hz, 1H), 6.26 (s, 1H, H-1'), 7.88 (s, 1H, H-8).

Example 76

This example describes the synthesis of methyl 1,3-di-n-pentylxanthine-7-β-D-2,3-O-isopropylidene-ribofuronate.

A mixture of 1,3-di-n-pentylxanthine-7-β-D-2,3-O-isopropylidene-ribofuranoside (136.7 mg, 0.29 mmol), sodium periodate (258 mg, 1.21 mmol), and ruthenium (III) chloride (0.8 mg, 0.0039 mmol) in chloroform:acetonitrile:water (2:2:3, 7 ml) was vigorously stirred for 86 h at room temperature. A workup similar to that for the compound of Example 75 yielded crude 1,3-di-n-hexylxanthine-7-β-D-2,3-O-isopropylidene-ribofuronic acid (109 mg) as thick syrup.

To a solution of acid in methanol (10 ml) were added DMAP (2.8 mg, 0.023 mmol) and then EDAC (109 mg, 0.57 mmol), and the reaction mixture was stirred for 25 h at room temperature. After removal of solvent, the residue was dissolved in ethyl acetate (50 ml) and washed with water (2×20 ml), and brine (20 ml), dried over anhydrous $MgSO_4$, filtered, and concentrated to dryness. The residue was purified by silica gel column chromatography (hexanes-ethyl acetate, 1:1) to yield methyl 1,3-di-n-pentylxanthine-7-β-D-2,3-O-isopropylidene-ribofuronate (85 mg, 76%) as foam, and unreacted 1,3-di-n-pentylxanthine-7-β-D-2,3-O-isopropylidene-ribofuranoside (40 mg) was recovered. $^1$H NMR (DMSO-$d_6$) d 0.88 (m, 6H, 2×C$\underline{H}_3$), 1.26–1.46 (m, 11H, 4×C$\underline{H}_2$ and isopropylidene), 1.49–1.67 (m, 5H, C$\underline{H}_2$ and isopropylidene), 1.70–1.80 (m, 2H, C$\underline{H}_2$), 3.77 (s, 3H, —OC$\underline{H}_3$), 3.94 (t, J=7.6 Hz, 2H, N—C$\underline{H}_2$), 4.09 (t, J=7.5 Hz, 2H, N—C$\underline{H}_2$), 4.80 (s, 1H), 5.16 (d, J=6.1 Hz, 1H), 5.45 (d, J=6.5 Hz, 1H), 6.25 (s, 1H, H-1'), 7.87 (s, 1H, H-8).

Example 77

This example describes the synthesis of methyl 1,3-di-n-hexylxanthine-7-β-D-2,3-O-isopropylidene-ribofuronate.

A mixture of 1,3-di-n-hexylxanthine-7-β-D-2,3-O-isopropylidene-ribofuranoside (113 mg, 0.23 mmol), sodium periodate (201 mg, 0.94 mmol), and ruthenium (III) chloride (1.23 mg, 0.006 mmol) in chloroform:acetonitrile:water (2:2:3, 7 ml) was vigorously stirred for 25 h at room temperature. A workup similar to that for the compound of Example 75 yielded crude 1,3-di-n-hexylxanthine-7-β-D-2,3-O-isopropylidene-ribofuronic acid (115 mg) as thick syrup.

To a solution of acid in methanol (2.3 ml) were added DMAP (2.8 mg, 0.023 mmol) and then EDAC (109 mg, 0.57 mmol), and the reaction mixture was stirred for 24 h at room temperature. After removal of solvent, the residue was dissolved in chloroform (50 ml) and washed with water (2×20 ml), and brine (20 ml), dried over anhydrous $MgSO_4$, filtered, and concentrated to dryness. The residue was purified by silica gel column chromatography (hexanes-ethyl acetate, 1:1) to yield methyl 1,3-di-n-hexylxanthine-7-β-D-2,3-O-isopropylidene-ribofuronate (65.1 mg, 55%) as a colorless solid, and unreacted 1,3-di-n-hexylxanthine-7-β-D-2,3-O-isopropylidene-ribofuranoside (26.6 mg) was recovered.

$^1$H NMR (DMSO-$d_6$) d 0.88 (pseudo t, J=6.6 and 6.4 Hz, 6H, 2×C$\underline{H}_3$), 1.22–1.49 (m, 15H, 6×C$\underline{H}_2$ and isopropylidene), 1.54–1.65 (m, 5H, C$\underline{H}_2$ and isopropylidene), 1.69–1.77 (m, 2H, C$\underline{H}_2$), 3.88 (s, 3H, —OC$\underline{H}_3$), 3.94 (pseudo t, J=8.0 and 7.6 Hz, 2H, N—C$\underline{H}_2$), 4.09 (pseudo t, J=7.8 and 7.6 Hz, 2H, N—C$\underline{H}_2$), 4.80 (s, 1H), 5.17 (d, J=6.0 Hz, 1H), 5.46 (d, J=6.5 Hz, 1H), 6.26 (d, J=2.2 Hz, 1H, H-1'), 7.87 (s, 1H, H-8).

Example 78

This example describes a radioligand binding assay used to study the structure activity relationship (SAR) at the $A_3$ receptor in a manner substantially similar to that set forth in Example 57.

The CHO cells stably expressing the $A_3$ receptor were grown in F-12 medium containing 10% FBS and penicillin/streptomycin (100 U/ml and 100 μg/ml respectively) at 37° C. in a 5% $CO_2$ atmosphere, and membrane homogenates were prepared as described in van Galen et al., *Mol. Pharmacol.*, 45, 1101–1111 (1994), van Bergen et al., ACS 206th National Meeting, Chicago, Ill., Abstract MEDI217 (August 1993), Gallo-Rodriguez et al., *J. Med. Chem.*, 37, 636–646 (1994), Olah et al., *Mol. Pharmacol.*, 45, 978–982 (1994). The binding of [$^{125}$I]4-amino-3-iodobenzyladenosine-5'-N-methyluronamide ([$^{125}$I]AB-MECA) to the CHO cells membranes was performed essentially as described in Gallo-Rodriguez et al., *J. Med. Chem.*, 37, 636–646 (1994); Olah et al., supra. Assays were performed in 50/10/1 buffer in glass tubes and contained 100 μl of the membrane suspension, 50 μl of [$^{125}$I]AB-MECA (final concentration 0.3 nM) and 50 μl of inhibitor. Inhibitors were routinely dissolved in DMSO and were then diluted with buffer; final DMSO concentrations never exceeded 1%. Incubations were carried out in duplicate for 1 h at 37° C. and were terminated by rapid filtration over Whatman GF/B filters, using a Brandell cell harvester (Brandell, Gaithersburg, Md.). Tubes were washed three times with 3 ml of buffer. Radioactivity was determined in a Beckman gamma 5500B g-counter. Non-specific binding was determined in the presence of 40 μM R-PIA. $K_i$-values were calculated according to Cheng-Prusoff (Cheng et al., supra) ,assuming a $K_d$ for [$^{125}$I]AB-MECA of 1.48 nM (Fozard et al., *Br. J. Pharmacol.*, 109, 3–5 (1993).

Binding of [$^3$H]PIA to $A_1$ receptors from rat brain membranes and of [$^3$H]CGS 21680 to $A_2$ receptors from rat striatal membranes was performed as described previously (Schwabe et al., *Naunyn-Schmiedeberg's Arch. Pharmacol.*, 313, 179–187 (1980); Jarvis et al., *J. Pharmacol. Exp. Therap.*, 251, 888–893 (1989)). Adenosine deaminase (3 U/ml) was present during the preparation of brain membranes, in which an incubation at 30° C. for 30 min is carried out, and during the incubation with radioligand. At least six different concentrations spanning three orders of magnitude, adjusted appropriately for the $IC_{50}$ of each compound, were used. $IC_{50}$ values, computer-generated using a non-linear regression formula on the InPlot program (GraphPAD, San Diego Calif.), were converted to apparent $K_i$ values using $K_d$ values of 1.0 and 14 nM for [$^3$H]PIA and [$^3$H]CGS 21680 binding, respectively, and the Cheng-Prusoff equation (Cheng et al., supra).

TABLE 4

Affinities of xanthine riboside derivatives in radioligand binding assays at rat brain $A_1$, $A_2$, and $A_3$ receptors[a]

| Compound | $K_i(A_1)$[b] | $K_i(A_2)$[c] | $K_i(A_3)$[d] | $A_1/A_3$ | $A_2/A_3$ |
|---|---|---|---|---|---|
| theophylline-7-riboside | 27,000 | 2% ($10^{-4}$) | 89,400 | 0.30 | >1 |
| 8-methoxy-theophylline-7-β-D-ribofuranoside [Example 59] | 21 ± 3% ($10^{-4}$) | 4% ($10^{-4}$) | 74.0 ± 6.8 | >1 | >1 |
| 1,3-di-n-propylxanthine-7-β-D-ribofuranoside | 15,900 | 32% ($10^{-4}$) | 81,200 | 0.20 | >1 |

TABLE 4-continued

Affinities of xanthine riboside derivatives in radioligand binding assays at rat brain $A_1$, $A_2$, and $A_3$ receptors[a]

| Compound | $K_i(A_1)$[b] | $K_i(A_2)$[c] | $K_i(A_3)$[d] | $A_1/A_3$ | $A_2/A_3$ |
|---|---|---|---|---|---|
| 1,3-di-n-butylxanthine-7-β-D-ribofuranoside [Example 60] | 4190 | 19,500 | 6030 | 0.69 | 3.2 |
| 1-benzyl-3-butylxanthine-7-β-D-ribofuranoside [Example 61] | 2190 ± 390 | 8670 ± 1890 | 12,900 ± 300 | 0.17 | 0.67 |
| 3-benzyl-1-butylxanthine-7-β-D-ribofuranoside [Example 61] | 1720 ± 30 | 4510 ± 1230 | 12,400 ± 20 | 0.14 | 0.36 |
| 1,3-di-n-butyl-2-thio-xanthine-7-β-D-ribofuranoside [Example 62] | 2250 ± 470 | 4250 ± 580 | 1400 ± 160 | 1.6 | 3.0 |
| 1,3-di-n-pentylxanthine-7-β-D-ribofuranoside [Example 63] | 8790 ± 1580 | 47,300 ± 2200 | 4810 ± 1070 | 1.8 | 9.8 |
| 1,3-di-n-hexylxanthine-7-β-D-ribofuranoside [Example 64] | 9750 ± 400 | 7.8 ± 3.1% ($10^{-5}$) 69 ± 2% ($10^{-4}$) | 43,000 ± 3400 | 0.23 | — |
| methyl 1,3-di-n-butylxanthine-7-β-D-ribofuronate [Example 65] | 3720 ± 200 | 0% ($3 \times 10^{-6}$) | 3230 ± 590 | 1.2 | >1 |
| 1,3-di-n-butylxanthine-7-β-D-ribofuronamide [Example 66] | 3060 ± 150 | 54,900 ± 5300 | 15,300 ± 700 | 0.20 | 3.6 |
| N-methyl 1,3-di-n-butylxanthine-7-β-D-ribofuronamide [Example 67] | 37,300 ± 4600 | 19 ± 2% ($10^{-4}$) | 229 ± 27 | 160 | >400 |
| N-methyl 1,3-di-n-pentylxanthine-7-β-D-ribofuronamide [Example 68] | 11,200 ± 1000 | 2% ($10^{-4}$) | 2630 ± 260 | 4.3 | >>1 |
| N-methyl 1,3-di-n-hexylxanthine-7-β-D-ribofuronamde [Example 69] | 30,800 ± 4900 | 0% ($10^{-4}$) | 10,300 ± 360 | 3.0 | >10 |
| N,N-dimethyl 1,3-di-n-butylxanthine-7-β-D-ribofuronamide [Example 70] | 9100 ± 2450 | 53,500 ± 8700 | 228,000 ± 9000 | 0.040 | 0.23 |
| N-ethyl 1,3-di-n-butylxanthine-7-β-D-ribofuronamide [Example 71] | 6210 ± 1060 | 38,100 ± 3500 | 602 ± 76 | 10 | 63 |

[a]A percent value indicates the percent displacement of radioligand at the concentration (M) given in parentheses.
[b]Displacement of specific [$^3$H]PIA binding, unless noted, in rat brain membranes, expressed as $K_i$ ± S.E.M. in nM (n = 3–5).
[c]Displacement of specific [$^3$H]CGS 21680 binding, unless noted, in rat striatal membranes, expressed as $K_i$ ± S.E.M. in nM (n = 3–6).
[d]Displacement of specific [$^{125}$I]AB-MECA binding, unless noted, in membranes of CHO cells stably transfected with the rat $A_3$-cDNA, expressed as $K_i$ ± S.E.M. in nM (n = 3–5).

As is apparent from the results set forth in Table 4, theophylline-7-riboside and the corresponding 1,3-dipropyl and dibutyl analogues bind weakly to $A_3$ receptors. These results clearly define the dependence of affinity of xanthine-7-ribosides at all of the adenosine receptors on the size of the $N_3$ and $N_1$ alkyl substituents. Affinity at $A_3$ receptors was enhanced by 1,3-dialkyl substituents in the order Pent≧Bu>>Hx>Pr≈Me. The rank order of affinity at $A_1$ receptors for 1,3-dialkyl substituents was: Bu>Pent≈Hex>Pr>Me, and, similarly, the order at $A_{2a}$ receptors was: Bu>Pent>Pr. In the ribose series, the 1,3-dipentyl analogue, namely 1,3-di-n-pentylxanthine-7-β-D-ribofuranoside, had the most favorable ratio of $A_3$ receptor selectivity, although it was only slightly selective (2-fold vs. $A_1$ and 10-fold vs. $A_{2a}$).

The introduction of an aromatic group on the 1- or 3-substituent, as in the benzyl derivatives 1-benzyl-3-butylxanthine-7-β-D-ribofuranoside and 3-benzyl-1-butylxanthine-7-β-D-ribofuranoside tended to increase the potency slightly at $A_1$ and $A_{2a}$ receptors (2–4 fold) and decrease potency slightly at $A_3$ receptors (2-fold) relative to 1,3-di-n-butylxanthine-7-β-D-ribofuranoside. Thus, it appears that, in the ribose series, the presence of a benzyl group is somewhat disadvantageous for achieving selectivity for $A_3$ receptors.

The introduction of 8-substitution theophylline-7-riboside in the form of a methoxy group (8-methoxytheophylline-7-β-D-ribofuranoside) was found to be detrimental to affinity at $A_1$ receptors but not at $A_3$ receptors. Thus, although a very weak competitor of binding, 8-methoxy-theophylline-7-β-D-ribofuranoside appears to be slightly selective for $A_3$ receptors.

The presence of a 2-thio group vs. a 2-oxo group in the pair of 1,3-dibutylxanthine-7-ribosides (cf. 1,3-di-n-butylxanthine-7-β-D-ribofuranoside vs. 1,3-di-n-butyl-2-thio-xanthine-7-β-D-ribofuranoside) increased potency at all three subtypes (4-fold at $A_3$ receptors) and slightly increased $A_3$ vs. $A_1$ selectivity.

The introduction of an ester group at the 5'-position (cf. methyl 1,3-di-n-butylxanthine-7-β-D-ribofuronate vs. 1,3-di-n-butylxanthine-7-β-D-ribofuranoside) maintained the same affinity at $A_1$ receptors as the corresponding 5'-CH$_2$OH analogue and increased affinity at $A_3$ receptors by 2-fold. Thus, methyl 1,3-di-n-butylxanthine-7-β-D-ribofuronate is of equal affinity at $A_1$ and $A_3$ receptors, but is selective for $A_3$ vs. $A_{2a}$ receptors. Like the ester derivative, the 5'-primary carboxamide analogue 1,3-di-n-butylxanthine-7-β-D-ribafuronamide maintained roughly the same affinity at $A_1$ receptors vs. 1,3-di-n-butylxanthine-7-β-D-ribofuranoside. However, 1,3-di-n-butylxanthine-7-β-D-ribofuronamide displayed a decreased affinity at $A_{2a}$ and $A_3$ receptors by 2.8- and 2.5-fold, respectively, vs. 1,3-di-n-butylxanthine-7-β-D-ribofuranoside.

The 5'-uronamide modification, which was previously found to result in $A_3$ selectivity in $N^6$-benzyl adenosine derivatives, was incorporated into xanthine-7-ribosides. The affinity of 5'-uronamides at $A_3$ receptors depended on the N-alkyluronamide substituent in the order MeNH>EtNH>>NH$_2$>>Me$_2$N (cf. the 1,3-dibutylxanthine analogues of Examples 66, 67, and 69–71). 1,3-Dibutylxanthine-7-riboside-5'-N-methyl-carboxamide, with a $K_i$ value of 229 nM at $A_3$ receptors, was 160-fold selective for $A_3$ vs. $A_1$ receptors and >400-fold selective vs. $A_{2a}$ receptors. The presence of the N-methyl group vs. the primary carboxamide, 1,3-di-n-butylxanthine-7-β-D-ribofuronamide, caused a 67-fold increase in affinity at $A_3$ receptors, and at both $A_1$ receptors or $A_{2a}$ receptors affinity diminished. Multiple substitution of the 5'-carboxamide group as in the N,N-dimethyl analogue, N,N-dimethyl 1,3-di-n-butylxanthine-7-β-D-ribofuronamide, was not favorable for $A_3$ selectivity. Relative to N-methyl 1,3-di-n-butylxanthine-7-β-D-ribofuronamide, this resulted in slightly increased affinity at $A_1$ and $A_{2a}$ receptors, and affinity at $A_3$ receptors was decreased by 1000-fold. The N-ethyl analogue, N-ethyl 1,3-di-n-butylxanthine-7-β-D-ribofuronamide, was slightly less potent than N-methyl 1,3-di-n-butylxanthine-7-β-D-ribofuronamide at $A_3$ receptors, but less selective. Thus, a monomethyl substitution in the 5'-uronamide series appears to be optimal.

Thus, the effect of decreased $A_3$ potency upon increase in the size of the purine 1- and 3-alkyl groups from butyl to hexyl, noted above for the 7-riboside series, was not seen in the 5'-uronamide series. The affinity of the 5'-uronamides was dependent on the 1,3-dialkyl substitution in the order Bu>Pent>Hex.

Example 79

This example illustrates other possible substituents which can be used in conjunction with the present inventive compounds and those compounds useful in the context of the present inventive method.

The following three compounds were synthesized and then their $A_3$-affinities were determined.

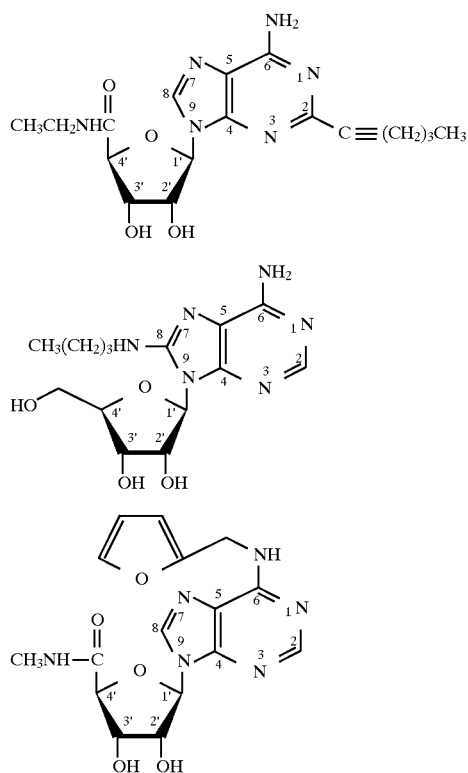

The $K_i$'s (nM) at the $A_3$ receptors for these three compounds were 25.6±3.2, 100,000, and 720±250, respectively. The heterocylic aryl substituent in the last of the three compounds, in particular, demonstrates that a wide variety of substituent groups may be utilized in conjunction with the present inventive compounds and those compounds useful in the context of the present inventive method without detracting from the high affinities of such compounds.

In addition, an isothiocyanate group in the 3-position of the $N^6$-benzyl ring provides a means for covalently linking the $A_3$ agonist to its receptor. $N^6$-(3-isothiocyanatobenzyl)adenosine-5'-N-methyluronamide was found to bind selectively to $A_3$ receptors. $K_i$ values for this isothiocyanate derivative in competition binding at rat brain $A_1$, $A_{2a}$, and $A_3$ receptors were 145, 272, and 10.0 nM, respectively. A preincubation with this derivative resulted in irreversible inhibition of radioligand binding at rat $A_3$ receptors in membranes of transfected CHO cells or RBL-2H3 mast cells, but not at rat $A_1$ or $A_{2a}$ receptors. The loss of binding sites for 0.1 nM [$^{125}$I]$N^6$-(4-aminobenzyl)adenosine-5'-N-methyluronamide, a high affinity $A_3$ receptor radioligand, in transfected CHO cell membranes was concentration-dependent with an $IC_{50}$ of 50 nM. No change was observed in the $K_d$ value of the remaining $A_3$ receptor sites. The inhibition was also insensitive to theophylline (1 mM), consistent with the pharmacology of rat $A_3$ receptors. Structurally similar adenosine analogues lacking the chemically reactive isothiocyanate group failed to irreversibly inhibit $A_3$-binding.

Moreover, primary amino derivatives served as functionalized congeners for coupling to other moieties for detection (by virtue of a radioactive or fluorescent or other spectroscopic label) or targeting purposes, without loss of affinity or $A_3$ selectivity. The attachment points for the functionalized chains were at the 2-position of the adenine ring and at the 3-position of the benzyl ring. Examples of cogeners are: 2-chloro-$N^6$-[3-(2-aminoethylcarbonylamino)-benzyl]adenosine-5'-N-methyluronamide, 2-(1-hexynyl)-$N^6$-[3-(2-aminoethylcarbonylamino)benzyl]adenosine-5'-N-methyluronamide, and 2-(6-amino-1-hexynyl)-$N^6$-(3-iodobenzyl)adenosine-5'-N-methyluronamide. Amides or thiourea groups were typically formed, using active esters, isothiocyanate, etc. derivatives of the added moiety.

Example 80

This example demonstrates the cerebral protective effect, particularly as to spontaneous seizures, resulting from the administration of an $A_3$-selective adenosine receptor agonist.

Spontaneous seizures are commonly observed in gerbils. Their presence constitutes a part of the normal, defensive behaviour in these animals. Hence, in gerbils, convulsive activity is unrelated to genetic modifications introduced artificially (e.g., laboratory bred, seizure-prone mice or rats). Spontaneous seizures are observed in 50–60% of the wild gerbil population. Seizures are easily elicited by either an unfamiliar or potentially threatening stimulus or environment.

During the studies of behavioural responses of gerbils to adenosine receptor stimulation, animals were exposed to the water maze model of spatial learning and memory. The control group (n=15) was injected with the vehicle given i.p. for 6 weeks prior to water maze tests. Twenty-four hours after the last injection, animals were exposed to the swim task. Immersion of animals in the swim tank whose water was kept at 32° C. produced an immediate, long-lasting (up to 2 min) seizure complex that was presented as myoclonic convulsions, followed by a period of rigidity and hind-limb extension. Convulsions were observed in 60% of the control group and disappeared within 4–5 days following the first immersion, i.e., the period required for animals to acclimatize to the new environment.

Contrary to the controls, chronic treatment of gerbils (n=20) with adenosine $A_3$ receptor IB-MECA (100 μg/kg i.p. daily for 6 wks) administered prior to water exposure during the swim task entirely eliminated seizing activity both during the first and subsequent water exposures. The acute administration of IB-MECA, however, was found to worsen the seizing activity.

In view of these data, it is clear that the chronic administration of IB-MECA and related adenosine $A_3$ receptor agonists is effective as an antiepileptogenic treatment in the context of both artificially induced seizures and spontaneous epileptic activity as seen in humans, and has, therefore, a significant therapeutic value.

Example 81

This example demonstrates the cerebral protective effect, particularly as to seizures induced by NMDA, pentamethylenetetrazole, and electric shock, resulting from the administration of an $A_3$-selective adenosine receptor agonist.

In gerbils, preischemic stimulation of adenosine $A_3$ receptors with a selective adenosine $A_3$ receptor agonist, particularly, $N^6$-(3-iodobenzyl) adenosine-5'-N-methylcarboxamide (IB-MECA), produces a regimen dependent effect, i.e., acute administration worsens, while chronic treatment improves, the outcome of brain ischemia of moderate intensity. Since several pathophysiological processes (e.g., activation of phospholipases $A_2$ and C, formation of $IP_3$) are typical of both cerebral ischemia and seizures, the effect of acute and chronic administration of IB-MECA on the outcome of seizures was further investigated. The effects of IB-MECA were studied in-models in which seizures were elicited using different mechanisms, i.e., neuronal hyperactivation [N-methyl-D-aspartate (NMDA)-evoked seizures], perturbation of GABA-ergic inhibition [pentamethylenetetrazole-induced convulsions (Rehavi et al., Eur. J. Pharmacol., 78, 353 (1978)], and generalized convulsions [electric shock (Mastropaolo et al., Pharmacol. Biochem. Behav., 41, 663 (1992)].

Male C57Bl/J5 mice (Jackson Laboratory, Bar Harbor, Me.) weighing 35 g were used in this study. All drugs were injected i.p. using a 25 gauge hypodermic needle. The adenosine $A_3$ receptor agonist $N^6$-3-(iodobenzyl) adenosine-5'-N-methylcarboxamide (IB-MECA) was dissolved in a 20:80 v/v solution of Alkamuls 620 (Rhône-Poulenc, Cranbury, N.J.) and injected either acutely or chronically. In the acute regimen, the drug was given at 10, 50, or 100 μg/kg. After establishing the dose response for chemically induced seizures in the acute regimen, the dose characterized by highest efficacy in all studied measures (i.e., 100 μg/kg) was selected for acute administration in studies of electroconvulsive shock. The same dose was selected for chronic administration (daily injections for 6 weeks). Saline-dissolved N-methyl-D-aspartate [NMDA (Research Biochemicals International, Natick, Mass.)] was given acutely at either 60 or 125 mg/kg, while acute injections of saline-dissolved pentamethylenetetrazole (Aldrich, Milwaukee, Wis.) were given at 75 mg/kg.

Previous experiments showed no statistical differences in the response to chemoconvulsants in animals injected either acutely or chronically with the vehicle. Therefore, in the present study, the chemoconvulsant controls were injected with the vehicle following the chronic schedule only.

All convulsant control and IB-MECA groups consisted of 10–15 animals. In the acute regimen, IB-MECA was injected 15 min prior to the administration of NMDA or pentamethylenetetrazole. In the chronic regimen, convulsants were administered 24 h after the last injection of IB-MECA. Injections of the vehicle followed the same pattern.

Graded electric shocks lasting 0.3 s were generated by a Hittman electroconvulsive shock generator (Modcraft mod. B24-III) and administered via ear clip electrodes. Starting from 70 V, shocks were increased every 2 s in 10 V steps until either a full tonic seizure was elicited or a maximum voltage of 170 V was reached. In the electric shock experiments, injections of IB-MECA were performed using acute or chronic regimen described above. Controls were injected with the vehicle following either the acute or chronic schedule of IB-MECA administration.

All experiments were performed in a quiet room illuminated with low intensity fluorescent lighting. Following injection of the convulsant or administration of electric shocks, mice were placed in individual transparent observation cages. In chemically-induced seizures, the onset, duration, and intensity of the subsequent neurological symptoms were monitored for the following 15 min. Thereafter, animals were transferred to their home cages, and their behaviour and mortality were observed for the subsequent 24 h. Since electric shock elicits an "either-or" response, only the tonic seizure-producing voltage and survival during the subsequent 24 h were observed in this part of the study.

The temperature effect of IB-MECA was measured using the Harvard (South Natick, Mass.) rectal probe in animals subjected to a light halothane anesthesia. The temperature was measured either 15 min after acute administration of 100 μg/kg IB-MECA or 24 h after the last injection of the drug when given chronically (N=5/group). There were no significant temperature differences following either acute or chronic administration of the drug.

The results of the NMDA experiments are set forth in Table 5 below, wherein the following neurological impairment scale was utilized: 1 - no change, 2 - depression, 3 - scratching/biting, 4 - locomotor hyperactivity, 5 - clonic seizures, 6 - clonic/tonic complexes. The results of the PMT and electroshock experiments are set forth in Tables 6 and 7, respectively.

TABLE 5

Percentage of animals with convulsive behavior appearing within 15 min of administration of NMDA and neurological impairment and mortality after administration of NMDA

| Compound | % Convulsing (P)[b] | Ave. Latency to Seizures (sec + S.E.M.) (P)[c] | Impairment + S.E.M. (P)[d] | % Mortality at 24 h (P)[e] |
|---|---|---|---|---|
| NMDA (60 mg/kg)[a] | 80 | 244 + 90 | 3.5 + 0.5 | 60 |
| IB-MECA (10 μg/kg) + NMDA (60 mg/kg) | 50 (NS) | 581 + 107 (<0.05) | 2.7 + 0.6 (NS) | 50 (NS) |
| IB-MECA (50 μg/kg) + NMDA (60 mg/kg) | 10 (<0.05) | 12[f] (NA) | 2.0 + 0.5 (NS) | 27 (NS) |
| acute IB-MECA (100 μg/kg) + NMDA (60 mg/kg) | 0 (NA) | NA (NA) | 1.4 + 0.4 (<0.05) | 10 (<0.05) |

TABLE 5-continued

Percentage of animals with convulsive behavior appearing within 15 min of administration of NMDA and neurological impairment and mortality after administration of NMDA

| Compound | % Con- vulsing (P)[b] | Ave. Latency to Seizures (sec + S.E.M.) (P)[c] | Impair- ment + S.E.M. (P)[d] | % Mortality at 24 h (P)[e] |
|---|---|---|---|---|
| chronic IB-MECA (100 µg/kg) + NMDA (60 mg/kg) | 30 (<0.05) | 689 + 108 (<0.05) | 1.8 + 0.4 (<0.05) | 20 (<0.05) |

[a]NMDA control group: N = 15; all other groups: N = 10
[b],[e]compared to NMDA control group; Fisher's test with Bonferroni's correction
[c],[d]compared to NMDA control group; Dunnett's test
[f]only one animal
NA = not applicable
NS = not significant

TABLE 6

Onset of convulsive behavior, degree of neurological impairment, and mortality in animals treated with PMT

| Com- pound | Onset (sec) + S.E.M. | Impairment + S.E.M. | Mortality (%) | | | | P[b] |
|---|---|---|---|---|---|---|---|
| | | | <15 min | 0.4–5 h | >5 h | Overall | |
| PMT (75 mg/kg) | 74 + 12 | 5.0 % 0.5 | 100 | 0 | 0 | 100 | |
| acute IB-MECA (100 µg/kg) + PMT (75 mg/kg) | 112 + 10[a] | 4.1 + 0.5 | 40 | 0 | 10 | 50 | <0.05 |
| chronic IB-MECA (100 µg/kg) + PMT (75 mg/kg) | 120 + 9 | 3.3 + 0.5[a] | 40 | 10 | 0 | 50 | <0.05 |

[a]P < 0.05; Student-Newman-Keuls test
[b]Fisher's exact test with Bonferroni's correction
PMT = pentamethylenetetrazole

TABLE 7

Threshold voltage and mortality of animals subjected to electroshock

| Compound | Threshold voltage + S.E.M. | % Mortality (at 24 h) |
|---|---|---|
| acute vehicle + E.S. | 91 + 4 | 80 |
| acute IB-MECA + E.S. | 106 + 10 | 70 |
| chronic vehicle + E.S. | 100 + 11 | 80 |
| chronic IB-MECA + E.S. | 118 + 13 | 30 (p < 0.05)[a] |

[a]compared to chronic vehicle + E.S.; Fisher's test
E.S. = electric shock

A. Acute Experiments

As is apparent from the results of Table 5, when compared to NMDA alone, acute administration of IB-MECA at 10 µg/kg prior to 60 mg/kg NMDA had no effect on either the incidence of seizures, or the degree of neurological impairment. However, administration of IB-MECA at 10 µg/kg caused a small but significant delay in the onset of convulsive behaviour. In the group given IB-MECA at 50 µg/kg, seizures within the initial 15 min after administration of NMDA were present in only one animal, while a long lasting locomotor depression characterized the rest of the group. Persistent myoclonic jerks were subsequently observed in two animals at ~30 to 45 min following the NMDA injection.

In the 10 µg/kg IB-MECA group, the mortality approached very closely that attained with NMDA alone, and all deaths occurred within 15 min following administration of NMDA. However, in the 50 µg/kg IB-MECA group only one animal died within that time (12 sec). The two subsequent deaths in that group (animals with myoclonic jerks) occurred at ~1 h after injection of NMDA.

At 100 µg/kg IB-MECA was protective in all studied measures. Although occasional scratching was present in some animals, clinically manifested seizures were completely absent. Neurological disturbances accompanying acute IB-MECA at 100 µg/kg followed by NMDA at 60 mg/kg were limited to a period of lethargic behaviour lasting 45–60 min after the injection of NMDA. During this period animals were fully responsive to external stimuli (sound, touch). A noxious stimulus (touch or tap with the tip of a pencil) caused a rapid translocation followed by a renewed period of locomotor quiescence. While moving, the gait of all animals appeared to be fully normal. The mortality was 10%, with the solitary death occurring 25 min after administration of NMDA.

Administration of pentamethylenetetrazole alone resulted in the death of all animals within 15 min. When IB-MECA preceded the convulsant, the onset of seizures and overall mortality were significantly reduced. There was no effect on the neurological impairment (Table 6).

Acute administration of IB-MECA resulted in an insignificant increase of threshold voltage (Table 7). Mortality remained unaffected.

B. Chronic Experiments

Chronic administration of IB-MECA resulted in the reduction of neurological impairment (Table 5). Tonic seizures were observed in 20% of animals, but their onset was significantly delayed. In the remaining animals, injection of NMDA rapidly elicited a protracted period of lethargic behaviour similar to that seen in animals injected acutely with IB-MECA at 100 µg/kg followed by 60 mg/kg NMDA. Following chronic administration of IB-MECA, the mortality was reduced to 30% (Table 5).

Chronic injection of IB-MECA prior to 75 mg/kg pentamethylenetetrazole had no significant effect on either the onset of seizures or neurological impairment (Table 6); however, the mortality was significantly reduced. The reduction did not differ from that seen following acute administration of IB-MECA.

Chronic treatment with IB-MECA produced no significant changes in threshold voltage; however, postictal mortality was significantly reduced (Table 7).

Example 82

This example demonstrates the anti-inflammatory effect resulting from the administration of an $A_3$-selective adenosine receptor agonist.

It is known that acute administration of IB-MECA results in stimulation of phospholipase C and an enhanced production of inositol 1,4,5-triphosphate. Similar stimulation characterizes ischemic and inflammatory processes in the brain, heart, and majority of other tissues. It is also known that following their initiation, these processes lead, in turn, to the activation of phospholipase $A_2$, and to subsequent arachidonic acid cascades, release of harmful prostanoid species, and production of free radicals. As a result of direct tissue impact (i.e., damage to cell membranes and organelles), and of prostanoid-mediated compromise of regional microcirculation, inflammatory processes ensue (aseptic inflammation).

The acute administration of IB-MECA impairs recovery of postischemic blood flow, whereas chronic administration of this drug improves it. Since microcirculatory compromise accompanies both inflammation and ischemia (following which inflammation has been also observed, cf. Greenfield's Neuropathology (Wiley & Sons)), chronically administered IB-MECA will act as an antiinflammatory agent affecting and reducing the intensity of both cellular (stimulation of phospholipase C and indirect effect on phospholipase $A_2$) and tissue responses (amelioration of regional microcirculatory reaction) to injury. These properties of IB-MECA and similar agents acting at adenosine $A_2$ receptors indicate their applicability as antiinflammatory therapeutics in the treatment of aseptic and, possibly, also septic tissue inflammation and trauma.

Example 83

This example demonstrates the precognitive effects resulting from the administration of an $A_3$-selective adenosine receptor agonist.

Studies of learning and memory were carried out in gerbils chronically injected with IB-MECA (100 μg/kg, daily for 2 months, n=20). These studies indicated that IB-MECA treatment decreases the time required for learning a task in the Morris water maze (a model of spatial memory) and results in significantly improved performance of the task (average time to target IB-MECA group 30 sec vs. controls injected chronically with the vehicle 40 sec, p<0.04). Open field studies of locomotion did not show any significant differences in locomotor behavior between animals injected chronically with IB-MECA and animals injected chronically with the vehicle.

Example 84

This example demonstrates the high correlation between ligand affinity for $A_3$ adenosine receptors in various species, particularly as between rats, gerbils, and humans.

The binding affinities at $A_3$ adenosine receptors in different species were compared by using the high affinity $A_3$ adenosine agonist ligand [$^{125}$I]AB-MECA (3-iodo-4-aminobenzyladenosine-5'-N-methyluronamide) in the presence of 1.0 μM of the $A_1$- and $A_{2a}$-adenosine antagonist XAC (8-[4-[[[[(2-aminoethyl)amino]carbonyl]methyl]oxy] phenyl]-1,3-dipropylxanthine). XAC was added to eliminate binding to non-$A_3$ receptors. In rat brain membranes [$^{125}$I] AB-MECA exhibited saturable, specific binding with a $K_d$ of 2.28 nM and a $B_{max}$ of 43 fmol/mg protein. The affinity of [$^{125}$I]AB-MECA at the gerbil and rabbit brain $A_3$-receptors was similar to the rat, demonstrating that the affinity of this agonist is not species dependent.

Figure 8:
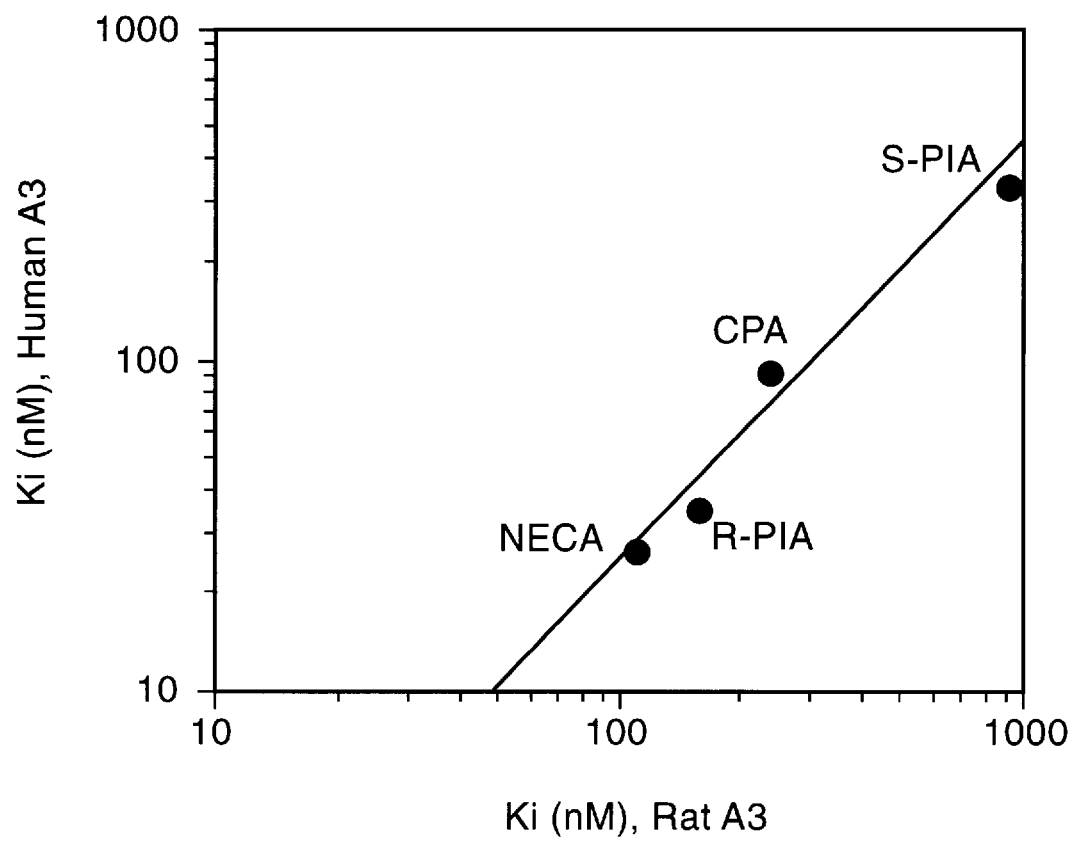
FIG. 8 is a graph of the correlation of affinity measured in binding assays at cloned rat brain $A_3$ receptors (stably transfected CHO cells, using $[^{125}I]$APNEA as radioligand) vs. cloned $A_3$ receptors from human brain (using $[^{125}I]$ABA as radioligand).

Agonist affinities were measured at cloned rat brain $A_3$ receptors stably expressed in CHO cells. $K_i$ values (expressed as nM vs. binding of [$^{125}$I]APNEA) were determined to be: S-PIA, 920±311; CPA, 240±36; R-PIA, 158±52; and NECA, 113±34. These values were compared with competition data for agonists at the human brain $A_3$ receptors, also expressed in CHO cells (Salvatore et al., Proc. Natl. Acad. Sci. USA, 90, 10365–10369 (1993)). A high degree of correlation was found as shown in FIG. 8, which demonstrates that human and rat brain $A_3$ receptors are highly similar in the relative affinity of agonists.

Thus, among adenosine agonists of varied structure (e.g., 5'-, 2-, and $N^6$-derivatives), binding at rat $A_3$ receptors is similar in relative order to binding at human $A_3$ receptors. Indeed, although the $K_i$ values in rat were several-fold higher than those in human, the correlation between human and rat receptors was found to be linear for the tested adenosine derivatives (FIG. 8, $r^2$=0.995).

All of the references cited herein, including publications, patents, and patent applications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A compound of the formula

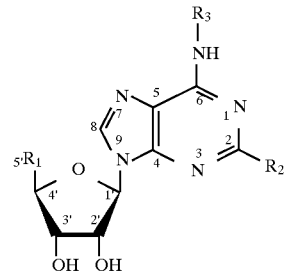

wherein $R_1$ is $R^aR^bNC(=O)$, wherein $R^a$ and $R^b$ may be the same or different and are selected from the group consisting of hydrogen, $C_1$–$C_{10}$ alkyl, $C_3$–$C_{10}$ cycloalkyl, amino, $C_1$–$C_{10}$ haloalkyl, $C_1$–$C_{10}$ aminoalkyl, and $C_1$–$C_{10}$ boc-aminoalkyl, or are joined together to form a heterocyclic ring containing two to five carbon atoms, $R_2$ is selected from the group consisting of halo, amino, $C_2$–$C_{10}$ alkenyl, $C_2$–$C_{10}$ alkynyl, thio, and $C_1$–$C_{10}$ alkylthio, and $R_3$ is selected from the group consisting of R- and S-1-phenylethyl, an unsubstituted benzyl group, and a phenylethyl or benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo, or a salt thereof.

2. The compound of claim 1, wherein $R^a$ and $R^b$ may be the same or different and are selected from the group consisting of hydrogen, $C_1$–$C_{10}$ alkyl, amino, $C_1$–$C_{10}$ haloalkyl, and $C_1$–$C_{10}$ aminoalkyl, $R_2$ is selected from the group consisting of halo, $C_2$–$C_{10}$ alkenyl, and $C_2$–$C_{10}$ alkynyl, and $R_3$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo.

3. The compound of claim 2, wherein $R_2$ is halo.

4. The compound of claim 2, wherein $R^a$ is hydrogen.

5. The compound of claim 4, wherein $R_3$ is unsubstituted benzyl.

6. The compound of claim 5, wherein $R^b$ is methyl.

7. The compound of claim 4, wherein $R_3$ is R-1-phenylethyl, S-1-phenylethyl, or a substituted benzyl.

8. The compound of claim 7, wherein $R^b$ is methyl.

9. The compound of claim 8, wherein $R_3$ is a substituted benzyl.

10. The compound of claim 9, wherein $R_3$ is a benzyl substituted in one or more positions with a substituent selected from the group consisting of halo, amino, acetamido, $C_1$–$C_{10}$ haloalkyl, and sulfo.

11. The compound of claim 10, wherein $R_3$ is a halo-substituted benzyl.

12. The compound of claim 2, wherein $R^a$ and $R^b$ may be the same or different and are selected from the group consisting of hydrogen and methyl.

13. The compound of claim 1, wherein $R^a$ and $R^b$ may be the same or different and are selected from the group consisting of hydrogen, methyl, amino, $C_1$–$C_{10}$ haloalkyl, and $C_1$–$C_{10}$ aminoalkyl, $R_2$ is selected from the group consisting of halo, $C_2$–$C_{10}$ alkenyl, $C_2$–$C_{10}$ alkynyl, thio, and $C_1$–$C_{10}$ alkylthio, and $R_3$ is selected from the group consisting of R- and S-1-phenylethyl, an unsubstituted benzyl group, and a benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo.

14. The compound of claim 13, wherein $R^a$ is hydrogen and $R_2$ is halo or $C_1$–$C_{10}$ alkylthio.

15. The compound of claim 14, wherein $R_3$ is a substituted benzyl.

16. The compound of claim 15, wherein $R^b$ is methyl.

17. The compound of claim 16, wherein said compound is selected from the group consisting of 2-chloro-$N^6$-(3-iodobenzyl)-9-[5-(methylamido)-β-D-ribofuranosyl]-adenine, $N^6$-(3-iodobenzyl)-2-methylamino-9-[5-(methylamido)-β-D-ribofuranosyl]-adenine, and $N^6$-(3-iodobenzyl)-2-methylthio-9-[5-(methylamido)-β-D-ribofuranosyl]-adenine.

18. The compound of claim 2, wherein $R_2$ is a $C_2$–$C_{10}$ alkyne of the formula R'—C≡C— where R' is a $C_1$–$C_8$ alkyl.

19. A compound selected from the group consisting of $N^6$-benzyladenosine-5'-N-alkyluronamide-$N^1$-oxide and $N^6$-benzyladenosine-5'-N-dialkyluronamide-$N^1$-oxide.

20. A pharmaceutical composition comprising a pharmaceutically acceptable carrier and a therapeutically effective amount of the compound of claim 1.

21. A pharmaceutical composition comprising a pharmaceutically acceptable carrier and a therapeutically effective amount of the compound of claim 2.

22. A pharmaceutical composition comprising a pharmaceutically acceptable carrier and a therapeutically effective amount of the compound of claim 19.

23. A compound of the formula

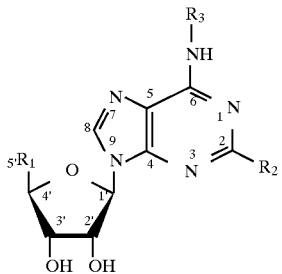

wherein $R_1$ is $R^a R^b NC(=O)$, wherein $R^a$ and $R^b$ may be the same or different and are selected from the group consisting of amino, $C_1$–$C_{10}$ haloalkyl, $C_1$–$C_{10}$ aminoalkyl, and $C_1$–$C_{10}$ boc-aminoalkyl, $R_2$ is selected from the group consisting of hydrogen, halo, amino, $C_1$–$C_{10}$ alkylamino, $C_2$–$C_{10}$ alkenyl, $C_2$–$C_{10}$ alkynyl, thio, and $C_1$–$C_{10}$ alkylthio, and $R_3$ is benzyl or R- or S-1-phenylethyl, or a benzyl or R- or S-1-phenylethyl group substituted in one or more ring positions with a substituent selected from the group consisting of $C_1$–$C_{10}$ alkyl, amino, halo, $C_1$–$C_{10}$ haloalkyl, nitro, hydroxy, acetamido, and sulfo, or a salt thereof.

24. The compound of claim 23, wherein $R^a$ and $R^b$ may be the same or different and are selected from the group consisting of amino, $C_1$–$C_{10}$ haloalkyl, and $C_1$–$C_{10}$ aminoalkyl, and $R_2$ is selected from the group consisting of hydrogen, halo, amino, $C_2$–$C_{10}$ alkenyl, and $C_2$–$C_{10}$ alkynyl.

25. The compound of claim 24, wherein $R_3$ is benzyl.

26. The compound of claim 25, wherein $R_2$ is hydrogen or halo.

27. The compound of claim 26, wherein $R_2$ is hydrogen.

28. The compound of claim 24, wherein $R_3$ is R-1-phenylethyl.

29. The compound of claim 28, wherein $R_2$ is hydrogen or halo.

30. The compound of claim 29, wherein $R_2$ is hydrogen.

31. A compound of the formula

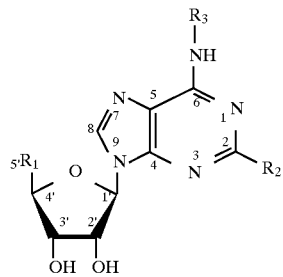

wherein $R_1$ is $R^a R^b NC(=O)$ wherein $R^a$ is hydrogen and $R^b$ is methyl, $R_2$ is hydrogen, and $R_3$ is benzyl or R- or S-1-phenylethyl, or a benzyl or R- or S-1-phenylethyl group substituted in one or more ring positions with a substituent selected from the group consisting of $C_1$–$C_{10}$ alkyl, amino, halo, $C_1$–$C_{10}$ haloalkyl, nitro, hydroxy, acetamido, and sulfo, or a salt thereof.

32. The compound of claim 31, wherein $R_3$ is a benzyl substituted in one or more positions with a substituent selected from the group consisting of amino, acetamido, $C_1$–$C_{10}$ haloalkyl, and sulfo.

33. The compound of claim 31, wherein $R_3$ is R-1-phenylethyl substituted in one or more positions with a substituent selected from the group consisting of amino, acetamido, $C_1$–$C_{10}$ haloalkyl, and sulfo.

34. The compound of claim 31, wherein said compound of $N^6$-3-iodobenzyl-5'-N-methylcarboxamidoadenosine.

35. A pharmaceutical composition comprising a pharmaceutically acceptable carrier and a therapeutically effective amount of the compound of claim 23.

36. A pharmaceutical composition comprising a pharmaceutically acceptable carrier and a therapeutically effective amount of the compound of claim 24.

37. A pharmaceutical composition comprising a pharmaceutically acceptable carrier and a therapeutically effective amount of the compound of claim 27.

38. A pharmaceutical composition comprising a pharmaceutically acceptable carrier and a therapeutically effective amount of the compound of claim 29.

39. A pharmaceutical composition comprising a pharmaceutically acceptable carrier and a therapeutically effective amount of the compound of claim 31.

40. A pharmaceutical composition comprising a pharmaceutically acceptable carrier and a therapeutically effective amount of the compound of claim 32.

41. A pharmaceutical composition comprising a pharmaceutically acceptable carrier and a therapeutically effective amount of the compound of claim 33.

42. A pharmaceutical composition comprising a pharmaceutically acceptable carrier and a therapeutically effective amount of the compound of claim 34.

43. A compound of the formula

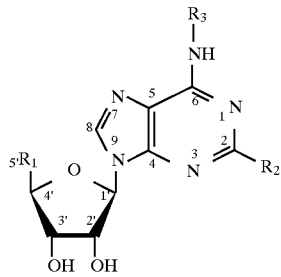

wherein $R_1$ is $HOR^c$, wherein $R^c$ is selected from the group consisting of amino, $C_1$–$C_{10}$ haloalkyl, $C_1$–$C_{10}$ aminoalkyl, $C_1$–$C_{10}$ boc-aminoalkyl, and $C_3$–$C_{10}$ cycloalkyl, $R_2$ is selected from the group consisting of hydrogen, halo, $C_1$–$C_{10}$ alkyloxy, amino, $C_1$–$C_{10}$ alkylamino, $C_2$–$C_{10}$ alkenyl, $C_2$–$C_{10}$ alkynyl, thio, and $C_1$–$C_{10}$ alkylthio, and $R_3$ is selected from the group consisting of R- and S-1-phenylethyl, an unsubstituted benzyl group, and a phenylethyl or benzyl group substituted in one or more positions with a substituent selected from the group consisting of $C_1$–$C_{10}$ alkyl, amino, halo, $C_1$–$C_{10}$ haloalkyl, nitro, hydroxy, acetamido, $C_1$–$C_{10}$ alkoxy, and sulfo.

44. A pharmaceutical composition comprising a pharmaceutically acceptable carrier and a therapeutically effective amount of the compound of claim 43.

45. A compound of the formula

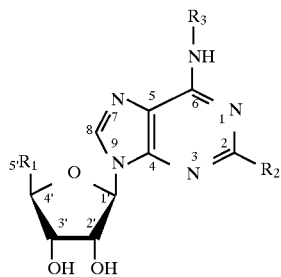

wherein $R_1$ is $HOR^c$, wherein $R^c$ is selected from the group consisting of $C_1$–$C_{10}$ alkyl, amino, $C_1$–$C_{10}$ haloalkyl, $C_1$–$C_{10}$ aminoalkyl, and $C_1$–$C_{10}$ boc-aminoalkyl, $R_2$ is selected from the group consisting of $C_2$–$C_{10}$ alkenyl, thio, and $C_1$–$C_{10}$ alkylthio, and $R_3$ is benzyl or R- or S-1-phenylethyl or a benzyl or a phenylethyl group substituted in one or more ring positions with a substituent selected from the group consisting of $C_1$–$C_{10}$ alkyl, $C_1$–$C_{10}$ haloalkyl, nitro, hydroxy, acetamido, and sulfo, or a salt thereof.

46. A pharmaceutical composition comprising a pharmaceutically acceptable carrier and a compound of claim 45.

47. A compound of the formula

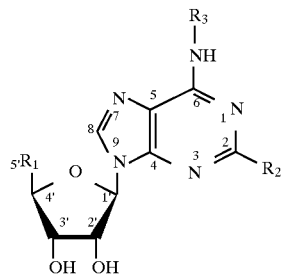

wherein $R_1$ is $HOR^c$, wherein $R^c$ is selected from the group consisting of amino, $C_1$–$C_{10}$ haloalkyl, $C_1$–$C_{10}$ aminoalkyl, and $C_1$–$C_{10}$ boc-aminoalkyl, $R_2$ is selected from the group consisting of hydrogen, halo, $C_2$–$C_{10}$ alkenyl, thio, and $C_1$–$C_{10}$ alkylthio, and $R_3$ is benzyl or R- or S-1-phenylethyl or a benzyl or a phenylethyl group substituted in one or more ring positions with a substituent selected from the group consisting of $C_1$–$C_{10}$ alkyl, $C_1$–$C_{10}$ haloalkyl, nitro, hydroxy, acetamido, and sulfo, or a salt thereof.

48. A pharmaceutical composition comprising a pharmaceutically acceptable carrier and a compound of claim 47.

49. A pharmaceutical composition comprising a pharmaceutically acceptable carrier and a compound of claim 9.

50. A pharmaceutical composition comprising a pharmaceutically acceptable carrier and a compound of claim 17.

* * * * *